(12) United States Patent
Kim et al.

(10) Patent No.: US 7,585,634 B2
(45) Date of Patent: Sep. 8, 2009

(54) METHOD OF PREDICTING RISK OF LUNG CANCER RECURRENCE, AND A COMPOSITION, KIT AND MICROARRAY FOR THE SAME

(75) Inventors: Byung-chul Kim, Suwon-si (KR); Jhin-gook Kim, Seongnam-si (KR); Nam Hur, Seoul (KR); Kyu-sang Lee, Suwon-si (KR); Dae-soon Son, Seoul (KR); Kyung-hee Park, Seoul (KR); Tae-jin Ahn, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/971,585

(22) Filed: Jan. 9, 2008

(65) Prior Publication Data

US 2008/0166729 A1 Jul. 10, 2008

(30) Foreign Application Priority Data

Jan. 9, 2007 (KR) ...................... 10-2007-0002643

(51) Int. Cl.
*C12Q 1/68* (2006.01)
*G01N 33/53* (2006.01)
*C12N 15/11* (2006.01)
*C12N 15/12* (2006.01)

(52) U.S. Cl. ............................. 435/6; 435/7.1; 536/7.1; 536/23.1; 536/24.31; 977/792

(58) Field of Classification Search ....................... None
See application file for complete search history.

(56) References Cited

U.S. PATENT DOCUMENTS

| 5,445,934 | A | 8/1995 | Fodor et al. |
| 5,744,305 | A | 4/1998 | Fodor et al. |
| 2005/0272061 | A1 | 12/2005 | Petroziello et al. |
| 2006/0252057 | A1 | 11/2006 | Raponi et al. |

OTHER PUBLICATIONS

Dawkins, The Extended Phenotype, 1982, Oxford University Press, Oxford, pp. 85-86.*
Vincent T. Devita, Jr. et al., "Cancer: Principles & Practice of Oncology", 6th Ed., chapter 31.2, pp. 925-983.

* cited by examiner

*Primary Examiner*—James Martinell
(74) *Attorney, Agent, or Firm*—Cantor Colburn LLP

(57) ABSTRACT

Provided is a method of predicting risk of lung cancer recurrence in a lung cancer patient or after a patient has lung cancer treatment, the method including: obtaining a biological sample from a lung cancer patient; measuring an expression level of at least one marker gene from the biological sample, the marker gene being selected from the group consisting of marker genes of Table 1, 2 or 3, to obtain data for the expression level of the marker gene; and determining whether the expression level of the marker gene corresponds to an expression level of a recurrence group or an expression level of a non-recurrence group.

14 Claims, No Drawings

METHOD OF PREDICTING RISK OF LUNG CANCER RECURRENCE, AND A COMPOSITION, KIT AND MICROARRAY FOR THE SAME

CROSS-REFERENCE TO RELATED PATENT APPLICATION

This application claims the benefit of Korean Patent Application No. 10-2007-0002643, filed on Jan. 9, 2007, in the Korean Intellectual Property Office, the disclosure of which is incorporated herein in its entirety by reference.

BACKGROUND OF THE INVENTION

1. Field of the Invention

The present invention relates to a method of predicting risk of lung cancer recurrence in a lung cancer patient or after a patient has lung cancer treatment, a method of preparing a report on the risk of lung cancer recurrence in a lung cancer patient or after a patient has lung cancer treatment, a report prepared by the same, and a composition, kit and microarray for diagnosing the risk of lung cancer recurrence in a lung cancer patient or after a patient has lung cancer treatment.

2. Description of the Related Art

Lung cancer is the leading cause of death due to cancer in the world. Lung cancer is categorized into two types, small cell lung cancer (SCLC) and non-small cell lung cancer (NSCLC), and about 80% of lung cancer cases are categorized as NSCLC. NSCLC is categorized into three sub-types: 40% of adenocarcinoma, 40% of squamous cell carcinoma and 20% of large cell carcinoma. Currently, a TMN staging system is widely accepted in the management of lung cancer.

In the TMN staging system, the primary tumor is subdivided into four T categories (T1-T4) depending upon the tumor size, site and local involvement. Lymph node spread is subcategorized into bronchio/pulmonary within the lung (N1), mediastinal spread on the same side of the lung as the primary tumor (N2) and mediastinal spread on the side of the lung opposite to the side having the primary tumor or supraclavicular involvement (N3). Distal or metastatic spread is either absent or present (M0 or M1). In general, lung cancer that does not metastasize is treated by being removed through a surgical operation. However, recurrence rate after a lung cancer removal operation is as high as 20 to 50% (*Cancer: Principles & Practice of Oncology,* 56th. ed. In: Devita D V, Hellman S. Rosenberg S A, eds. Philadelphia, Pa.: Lippincott Williams & Wilkins, 2001).

Conventionally, a method of diagnosing lung cancer using a marker gene specific to lung cancer is known. For example, U.S. Patent Publication No. 2006025057 discloses a method of diagnosing lung cancer using a marker specific to lung cancer. Further, U.S. Patent Publication No. 20050272061 discloses a method of diagnosing cancer in an individual, comprising measuring an L gene that is specifically and distinctively expressed in lung cancer tissues and cells, and its products.

However, there is still a need for developing a method of effectively predicting the risk of lung cancer recurrence in a lung cancer patient or a patient who has had lung cancer treatment to the extent that the method is applied to clinical practices.

SUMMARY OF THE INVENTION

The present invention provides a method of predicting risk of lung cancer recurrence in a lung cancer patient or after a patient has lung cancer treatment.

The present invention also provides a method of preparing a report on the risk of lung cancer recurrence in a lung cancer patient or after a patient has lung cancer treatment and a report prepared by the same.

The present invention also provides a composition, kit and microarray for diagnosing the risk of lung cancer recurrence in a lung cancer patient or after a patient has lung cancer treatment.

According to an aspect of the present invention, there is provided a method of predicting risk of lung cancer recurrence in a lung cancer patient or after a patient has lung cancer treatment, the method comprising:

obtaining a biological sample from a lung cancer patient;

measuring an expression level of at least one marker gene from the biological sample, the marker gene being selected from the group consisting of marker genes of Table 1, 2 or 3 to obtain data for the expression level of the marker gene; and determining whether the expression level of the marker gene corresponds to an expression level of a recurrence group or an expression level of a non-recurrence group.

The method of predicting risk of lung cancer recurrence in a lung cancer patient or after a patient has lung cancer treatment includes obtaining a biological sample from a lung cancer patient.

The obtaining a biological sample may include any operation that obtains a sample including an arbitrary cell from a lung cancer patient. For example, the biological sample may be blood, plasma, serum, urine, tissue, cell, organ, bone marrow, saliva, expectoration, cerebrospinal fluid and the like, but is not limited thereto. The biological sample may be preferably lung cancer tissue. The biological sample may be lung cancer tissue removed during a lung cancer removal operation, but is not necessarily obtained by the lung cancer removal operation. The obtainment of the lung cancer tissue may be physically conducted or optically conducted through a laser or the like.

The method of predicting a risk of lung cancer recurrence in a lung cancer patient or a patient after a lung cancer treatment includes measuring an expression level of at least one marker gene selected from the group consisting of marker genes of Table 1, 2 or 3 in the sample to obtain data for the expression level of the marker gene.

The measuring an expression level of the marker gene may be performed by measuring an expression level of at least one marker gene selected from the group consisting of marker genes of Table 1. Preferably, in this operation, expression levels of at least 2, 4, 6, 8, 10, 15, 20, 30, 70, 100, 150 or a total of 166 marker genes selected from the group consisting of marker genes of Table 1 may be measured. In this case, the lung cancer may be adenocarcinoma or squamous cell carcinoma.

When the lung cancer is adenocarcinoma, the measuring an expression level of the marker gene may be performed by measuring an expression level of at least one marker gene selected from the group consisting of marker genes of Table 2. Preferably, in this operation, expression levels of at least 2, 4, 6, 8, 10, 15, 20, 30, 70, 100, 150, 200, 250 or a total of 300 marker genes selected from the group consisting of marker genes of Table 2 may be measured.

When the lung cancer is squamous cell carcinoma, the measuring an expression level of the marker gene may be performed by measuring an expression level of at least one marker gene selected from the group consisting of marker genes of Table 3. Preferably, in this operation, an expression level of at least 2, 4, 6, 8, 10, 15, 20, 30, 70, 100, 150, or a total of 166 marker genes selected from the group consisting of marker genes of Table 3 may be measured.

The measuring an expression level of the marker gene includes measuring an arbitrary expression product expressed from the maker gene. For example, this operation may be measuring a level of mRNA or protein derived from the marker gene.

The "measurement of a level of mRNA" may be analyzed using a conventional method including RT-PCR, competitive RT-PCR, real-time RT-PCR, RNase protection assay, northern blotting, DNA microarray and the like. Preferably, the measurement of a level of mRNA may be carried out by hybridizing mRNA isolated from the biological sample or cDNA derived therefrom on a microarray on which a probe specific to at least one marker gene selected from the group consisting of marker genes of Tables 1, 2 and 3 is immobilized to measure a degree of the obtained hybridization. The degree of the hybridization may be measured using an arbitrary measurement method known to those of ordinary skill in the art, such as fluorescence measurement and electrical measurement. In this case, the probe or target nucleic acid may be labeled with a detectable appropriate marker. Herein, the cDNA may be directly amplified by RT-PCR using sense and anti-sense primer pair targeted to at least one marker gene selected from the group consisting of marker genes of Tables 1, 2 and 3 as a primer.

The "measurement of a level of protein" may be conducted using any conventional protein measuring or detecting method. For example, the measurement of a level of protein may be conducted using an analysis method that uses an antibody that specifically binds with protein expressed from at least one marker gene selected from the group consisting of marker genes of Tables 1, 2 and 3. Examples of the protein analysis method using an antibody may include western blotting, enzyme-linked immunosorbent assay (ELISA), radio-immunoassay, radioimmunodiffusion, Ouchterlony immunodiffusion, rocket immunoelectrophoresis, immunoprecipitation assay, complement fixation analysis, Fluorescence Activated Cell Sorting (FACS) and the like, but are not limited thereto. Examples of the ELISA include a direct ELISA, an indirect ELISA, a direct sandwich ELISA, an indirect sandwich ELISA and the like. The western blotting is a method in which total protein is isolated and electrophoresized to separate protein according to their size, the separated proteins are then moved into a nitrocellulose membrane to be reacted with an antibody, and a generated amount of the antigen-antibody complex is confirmed using a labeled antibody. In addition, the level of protein may be measured using enzyme, substrate, coenzyme, ligand or the like that specifically binds with the target protein.

The expression level of the marker gene may be determined by measuring an amount of an amplification product obtained by nucleic acid amplification that is carried out by a reverse transcriptase-polymerase chain reaction (RT-PCR) using RNA isolated from the sample as a template.

In addition, the method of predicting a risk of lung cancer recurrence in a lung cancer patient or a patient after a lung cancer treatment includes determining whether the expression level of the marker gene corresponds to an expression level of a recurrence group or an expression level of a non-recurrence group.

The term "recurrence group" refers to a group of patients with lung cancer recurrence within a certain period after a lung cancer treatment among lung cancer patients. Preferably, the term "recurrence group" may refer to a group of patients with lung cancer recurrence within one year after a lung cancer removal operation among lung cancer patients. However, types of lung cancer treatment and a period which is a basis of recurrence may be appropriately adjusted by those of ordinary skill in the art. In addition, the term "non-recurrence group" refers to a group of patients without lung cancer recurrence even after a certain period passes by after a lung cancer treatment among lung cancer patients. Preferably, the term "non-recurrence group" refers to a group of patients without lung cancer recurrence even after three years after a lung cancer removal operation among lung cancer patients. However, types of lung cancer treatment and a period which is a basis of non-recurrence may be appropriately adjusted by those of ordinary skill in the art.

The "expression level of recurrence group" or "expression level of non-recurrence group" corresponds to a standard expression level. Through preliminary experiment, a biological sample of a lung cancer patient, for example, lung cancer tissue is collected in advance. An expression level of at least one marker gene selected from the group consisting of marker genes of Tables 1, 2 and 3 in the lung cancer tissue is then measured. Patients after lung cancer treatment are divided into a recurrence group and a non-recurrence group in which recurrence and non-recurrence respectively occur as time passes by. Next, each of expression levels of the marker gene measured in the recurrence and non-recurrence groups is divided into an expression level of the recurrence group or the non-recurrence group.

The determining whether the expression level of the marker gene corresponds to an expression level of a recurrence group or an expression level of a non-recurrence group may be performed using a statistical forecasting model. In this case, whether the expression level of the marker gene corresponds to an expression level of a recurrence group or an expression level of a non-recurrence group is determined by whether the expression levels show a statistically meaningful difference from each other.

Whether there is a statistically meaningful difference may be determined using a statistical analysis model known to those of ordinary skill in the art. Preferably, the statistical analysis model may be a statistical forecasting model selected from the group consisting of a Linear Discrimination Analysis (LDA) model, a Quadratic Discrimination Analysis (QDA) prediction model, a Neural Network model, a Decision Tree model, a Support Vector Machine model and a Naive Bayes model, but is not limited thereto.

Examples of the determining whether the expression level of the marker gene corresponds to an expression level of a recurrence group or an expression level of a non-recurrence group include determining to correspond to a non-recurrence group if the expression level of the marker gene shows a statistically meaningful difference from the expression level of the recurrence group, and determining to correspond to a recurrence group if the expression level of the marker gene shows a statistically meaningful difference from the expression level of the non-recurrence group. In addition, examples of the determining whether the expression level of the marker gene corresponds to an expression level of a recurrence group or an expression level of a non-recurrence group include determining to correspond to a recurrence group if the expression level of the marker gene does not show a statistically meaningful difference from the expression level of the recurrence group, and determining to correspond to a non-recurrence group if the expression level of the marker gene does not show a statistically meaningful difference from the expression level of the non-recurrence group.

The statistically meaningful difference may have p values that are statistically meaningfully higher or lower than the expression level of the recurrence group or non-recurrence group. Preferably, the p value may be less than 0.05.

In the method of predicting a risk of lung cancer recurrence in a lung cancer patient or a patient after a lung cancer treatment, if the expression level of the marker gene is determined to correspond to the expression level of the recurrence group, a risk of lung cancer recurrence in a patient can be predicted to be high. In addition, if the expression level of the marker gene is determined to correspond to the expression level of the non-recurrence group, a risk of lung cancer recurrence in a patient can be predicted to be low.

In the method of predicting a risk of lung cancer recurrence in a lung cancer patient or a patient after a lung cancer treatment, specificity may be at least 50%, preferably 60%, more preferably at least 70%, far more preferably at least 80%, and most preferably 90%.

According to another aspect of the present invention, there is provided a method of preparing a report on the risk of lung cancer recurrence in a lung cancer patient or after a patient has lung cancer treatment, the method comprising preparing a report representing predicted results according to the method of predicting risk of lung cancer recurrence in a lung cancer patient or after a patient has lung cancer treatment.

The report may include probability of recurrence according to time.

According to another aspect of the present invention, there is provided a report on a risk of lung cancer recurrence in a lung cancer patient or a patient after a lung cancer treatment, which is prepared by the method of preparing a report on the risk of lung cancer recurrence in a lung cancer patient or after a patient has lung cancer treatment.

According to another aspect of the present invention, there is provided a composition for diagnosing the risk of lung cancer recurrence in a lung cancer patient or after a patient has lung cancer treatment, comprising at least one probe or probe set selected from marker genes selected from the group consisting of marker genes of Tables 1, 2 and 3.

The composition may further comprise a reagent required for hybridization reaction with the marker gene in a sample or nucleic acid products expressed therefrom. In addition, the composition may further comprise a buffer, a solvent or the like that stabilizes the probe and acts as a medium of the reaction.

The term "probe" used through the present application refers to a nucleic acid strand that is partially or completely complementary to a target nucleic acid, and refers to oligonucleotide that can bind with the target nucleic acid by a base-specific method. Preferably, the probe may be oligonucleotide that is completely complementary to the target nucleic acid. The probe can be a conventionally known arbitrary nucleic acid derivative that can complementarily bind to the target nucleic acid, such as peptide nucleic acid as well as nucleic acid.

The binding of the probe with the target nucleic acid (in general, referred to as hybridization) may be sequence-dependently carried out under various conditions. In general, the hybridization is performed in a specific ion intensity at specific pH at a temperature that is about 5° C. lower than Tm with respect to a specific sequence. The Tm refers to a state at which 50% of probe complementary to a target sequence is bound to the target sequence. Examples of the conditions of the hybridization may include a pH in the range of 7.0-8.3 and a Na$^+$ ion concentration of 0.01-1.0 M. In addition, to raise specificities of the target nucleic acid and the probe, the hybridization may be carried out under conditions that make the binding of the probe with the target nucleic acid unstable, for example, at a high temperature and in the presence of a high concentration of an unstabilizing agent (for example formamide).

The probe may be any length of polynucleotide that can sequence-specifically be bound to the target nucleic acid. For example, the length of the probe may be 7-200 nucleotides, 7-150 nucleotides, 7-100 nucleotides, 7-50 nucleotides, or a full-length strand of gene, but is not limited thereto.

The probe may be labeled with a detectable marker. The detectable marker may be a fluorescent marker such as Cy3 or Cy5, a radioactive material marker, enzyme that converts a substrate to chromogen, or the like, but is not limited thereto.

According to another aspect of the present invention, there is provided a kit for diagnosing the risk of lung cancer recurrence in a lung cancer patient or after a patient has lung cancer treatment, comprising at least one probe or probe set selected from marker genes selected from the group consisting of marker genes of Tables 1, 2 and 3.

The probe is the same as defined above. The probe may be labeled with a detectable marker. The detectable marker may be a fluorescent marker such as Cy3 or Cy5, a radioactive material marker, enzyme that converts a substrate to chromogen, or the like, but is not limited thereto.

In the kit, the probe or probe set may be immobilized on a microarray. A target nucleic acid in a sample is hybridized with the probe on the microarray, and the presence and concentration of the target nucleic acid may be determined by measuring the hybridized results. During the hybridization, the target nucleic acid may be labeled with a detectable marker.

The kit may further include a manual that describes a process of measuring a risk of lung cancer recurrence in a lung cancer patient or a patient after a lung cancer treatment.

According to another aspect of the present invention, there is provided a kit for diagnosing the risk of lung cancer recurrence in a lung cancer patient or after a patient has lung cancer treatment, comprising sense and anti-sense primer pair with respect to at least one marker gene selected from the group consisting of marker genes of Tables 1, 2 and 3.

The term "primer" used herein refers to a nucleic acid having a free 3' hydroxy group that is partially or completely complementary to a target nucleic acid and can bind with the template nucleic acid by a sequence-specific method, and refers to oligonucleotide that functions as a starting point for template strand transcription in polymerization.

The kit may further comprise a reagent required for PCR or RT-PCR using the primer described above as a primer and the target nucleic acid as a template. The reagent may include a buffer solution, a DNA polymerase (and/or reverse transcriptase), and 4 types of dNTPs.

The primer may be any length of polynucleotide that can sequence-specifically be bound to the template nucleic acid and function as a starting point for template strand transcription in polymerization. For example, the length of the primer may be 7-200 nucleotides, 7-150 nucleotides, 7-100 nucleotides, 7-50 nucleotides, or a full-length strand of a gene, but is not limited thereto.

The primer may be labeled with a detectable marker. The detectable marker may be a fluorescent marker such as Cy3 or Cy5, a radioactive material marker, enzyme that converts a substrate to chromogen, or the like, but is not limited thereto.

According to another aspect of the present invention, there is provided a microarray for diagnosing a risk of lung cancer recurrence in a lung cancer patient or a patient after a lung cancer treatment, in which at least one probe or probe set selected from marker genes selected from the group consisting of marker genes of Tables 1, 2 and 3.

The term "microarray" refers to a polynucleotide group immobilized on a substrate in a high concentration. The polynucleotide group is respectively immobilized on a certain region. Such microarray is well-known to those of ordinary skill in the art. The microarray is, for example, disclosed in U.S. Pat. Nos. 5,445,934 and 5,744,305, and contents of these patents are included in the present application by reference. The substrate may have various shapes such as plate, film and microsphere (or bead).

The probe is the same as defined above. The probe may be labeled with a detectable marker. The detectable marker may be a fluorescent marker such as Cy3 or Cy5, a radioactive material marker, enzyme that converts a substrate to chromogen, or the like, but is not limited thereto.

The gene expression pattern of the lung cancer cell after lung cancer tissue removal operation is analyzed through a hybridization with the probe on the microarray, and a marker gene that is determined to have a difference in an expression level between a patient with lung cancer recurrence within one year (recurrence group) and a patient without lung cancer recurrence even after three years (non-recurrence group) is selected. The results are shown in Table 1 below. A total number of patients was 60. Among them, the number of patients with lung cancer recurrence within one year after lung cancer tissue removal operation was 19, and the number of patients without lung cancer recurrent even after three years was 41.

TABLE 1

| NO. | Probe Set ID | Gene Name | Gene Symbol | Genbank Accession # | T-test p-value | Fold change (abs) |
|---|---|---|---|---|---|---|
| 001 | 1552486_s_at | lactamase, beta | LACTB | NM_171846 | 0.005162234 | 1.522293 |
| 002 | 1553105_s_at | desmoglein 2 | DSG2 | NM_001943 | 0.019467462 | 2.3323212 |
| 003 | 1553530_a_at | integrin, beta 1 (fibronectin receptor, beta polypeptide, antigen CD29 includes MDF2 MSK12) | ITGB1 | NM_033669 | 0.01684671 | 1.7791877 |
| 004 | 1553678_a_at | integrin, beta 1 (fibronectin receptor, beta polypeptide, antigen CD29 includes MDF2, MSK12) | ITGB1 | NM_133376 | 0.012459265 | 1.7374801 |
| 005 | 1554087_at | hypothetical protein FLJ32549 | FLJ32549 | BC036246 | 0.002290308 | 1.5143739 |
| 006 | 1554761_s_at | hypothetical protein FLJ20397 | FLJ20397 | BC010850 | 0.001210456 | 1.6267678 |
| 007 | 1555326_a_at | ADAM metallopeptidase domain 9 (meltrin gamma) | ADAM9 | AF495383 | 0.012324799 | 2.1980886 |
| 008 | 1555564_a_at | I factor (complement) | IF | BC020718 | 0.007528743 | 2.5875902 |
| 009 | 1555705_a_at | chemokine-like factor superfamily 3 | CKLFSF3 | AY168714 | 0.004961676 | 1.8587251 |
| 010 | 1557987_at | PI-3-kinase-related kinase SMG-1-like locus | LOC641298 | BC042832 | 0.010989661 | 1.7944587 |
| 011 | 1558678_s_at | metastasis associated lung adenocarcinoma transcript 1 (non-coding RNA) | MALAT1 | BE708432 | 0.00670648 | 1.6990829 |
| 012 | 160020_at | matrix metallopeptidase 14 (membrane-inserted) | MMP14 | Z48481 | 0.005463324 | 1.5193439 |
| 013 | 200604_s_at | protein kinase, cAMP-dependent, regulatory, type I, alpha (tissue specific extinguisher 1) | PRKAR1A | M18468 | 0.017312625 | 1.5803499 |
| 014 | 200615_s_at | adaptor-related protein complex 2, beta 1 subunit | AP2B1 | AL567295 | 0.007407852 | 1.6839108 |
| 015 | 200864_s_at | RAB11A, member RAS oncogene family | RAB11A | NM_004663 | 0.000163535 | 1.5653288 |
| 016 | 200922_at | KDEL (Lys-Asp-Glu-Leu) endoplasmic reticulum protein retention receptor 1 | KDELR1 | NM_006801 | 0.004791257 | 1.638207 |
| 017 | 201020_at | tyrosine 3-monooxygenase/tryptophan 5-monooxygenase activation protein, eta polypeptide | YWHAH | NM_003405 | 0.009279575 | 1.5148095 |
| 018 | 201179_s_at | guanine nucleotide binding protein (G protein), alpha inhibiting activity polypeptide 3 | GNAI3 | J03005 | 0.014834337 | 1.5069977 |
| 019 | 201309_x_at | chromosome 5 open reading frame 13 | C5orf13 | U36189 | 0.011555359 | 2.1326842 |
| 020 | 201363_s_at | influenza virus NS1A binding protein | IVNS1ABP | AB020657 | 0.00119686 | 1.5838884 |
| 021 | 201505_at | laminin, beta 1 | LAMB1 | NM_002291 | 0.000568398 | 1.8073287 |
| 022 | 201506_at | transforming growth factor, beta-induced, 68 kDa | TGFBI | NM_000358 | 0.008768089 | 1.9059453 |
| 023 | 201548_s_at | Jumonji, AT rich interactive domain 1B (RBP2-like) | JARID1B | W02593 | 0.010550437 | 1.5276276 |
| 024 | 201559_s_at | chloride intracellular channel 4 | CLIC4 | AF109196 | 0.002245945 | 2.1570368 |
| 025 | 201564_s_at | fascin homolog 1, actin-bundling protein (Strongylocentrotus purpuratus) | FSCN1 | NM_003088 | 0.007795681 | 2.1724482 |
| 026 | 201578_at | podocalyxin-like | PODXL | NM_005397 | 0.00303411 | 1.8943018 |
| 027 | 201617_x_at | caldesmon 1 | CALD1 | NM_004342 | 0.01926877 | 1.8294148 |
| 028 | 201646_at | scavenger receptor class B, member 2 | SCARB2 | AA885297 | 0.006063032 | 1.6768507 |
| 029 | 201647_s_at | scavenger receptor class B, member 2 | SCARB2 | NM_005506 | 0.015885489 | 1.6841809 |
| 030 | 201695_s_at | nucleoside phosphorylase | NP | NM_000270 | 0.018524641 | 1.6833633 |
| 031 | 201722_s_at | UDP-N-acetyl-alpha-D-galactosamine:polypeptide N-acetylgalactosaminyltransferase 1 (GalNAc-T1) | GALNT1 | AV692127 | 0.009770202 | 1.5369248 |
| 032 | 201918_at | Solute carrier family 25, member 36 | SLC25A36 | AI927944 | 0.00259865 | 1.6228764 |
| 033 | 201942_s_at | carboxypeptidase D (melanoma growth stimulating activity, alpha) | CPD | D85390 | 0.017363481 | 1.7431495 |
| 034 | 202267_at | laminin, gamma 2 | LAMC2 | NM_005562 | 0.004330024 | 2.8191426 |
| 035 | 202543_s_at | glia maturation factor, beta | GMFB | BC005359 | 0.008048828 | 1.5254242 |
| 036 | 202604_x_at | ADAM metallopeptidase domain 10 | ADAM10 | NM_001110 | 0.002003783 | 1.767903 |
| 037 | 202627_s_at | serpin peptidase inhibitor, clade E (nexin, plasminogen activator inhibitor type 1), member 1 | SERPINE1 | AL574210 | 0.00091248 | 3.0523725 |
| 038 | 202628_s_at | serpin peptidase inhibitor, clade E (nexin, plasminogen activator inhibitor type 1), member 1 | SERPINE1 | NM_000602 | 0.00504642 | 2.6835847 |
| 039 | 202817_s_at | synovial sarcoma translocation, chromosome 18 | SS18 | NM_005637 | 0.005462693 | 1.5148987 |
| 040 | 202859_x_at | interleukin 8 | IL8 | NM_000584 | 0.014948112 | 2.1844351 |
| 041 | 202936_s_at | SRY (sex determining region Y)-box 9 (campomelic dysplasia, autosomal sex-reversal) | SOX9 | NM_000346 | 0.019816045 | 2.2876046 |
| 042 | 202949_s_at | four and a half LIM domains 2 | FHL2 | NM_001450 | 0.006776552 | 2.2249734 |
| 043 | 202998_s_at | lysyl oxidase-like 2 | LOXL2 | NM_002318 | 0.006687925 | 2.0231075 |
| 044 | 203066_at | B cell RAG associated protein | GALNAC4S-6ST | NM_014863 | 0.00419499 | 1.5032523 |

TABLE 1-continued

| NO. | Probe Set ID | Gene Name | Gene Symbol | Genbank Accession # | T-test p-value | Fold change (abs) |
|---|---|---|---|---|---|---|
| 045 | 203072_at | myosin IE | MYO1E | NM_004998 | 0.000449373 | 1.5877136 |
| 046 | 203293_s_at | lectin, mannose-binding, 1 | LMAN1 | NM_005570 | 0.002661762 | 1.9762497 |
| 047 | 203294_s_at | lectin, mannose-binding, 1 | LMAN1 | U09716 | 0.000473367 | 1.9764429 |
| 048 | 203414_at | monocyte to macrophage differentiation-associated | MMD | NM_012329 | 0.001585437 | 1.6128623 |
| 049 | 203553_s_at | mitogen-activated protein kinase kinase kinase kinase 5 | MAP4K5 | NM_006575 | 0.010453912 | 1.5251595 |
| 050 | 203924_at | glutathione S-transferase A1 | GSTA1 | NM_000846 | 0.004046575 | 4.2017674 |
| 051 | 203988_s_at | fucosyltransferase 8 (alpha (1,6) fucosyltransferase) | FUT8 | NM_004480 | 0.01139016 | 1.6090198 |
| 052 | 204426_at | transmembrane emp24 domain trafficking protein 2 | TMED2 | NM_006815 | 0.015985437 | 1.6165011 |
| 053 | 204470_at | chemokine (C-X-C motif) ligand 1 | CXCL1 | NM_001511 | 0.001788037 | 3.218731 |
| 054 | 204702_s_at | nuclear factor (erythroid-derived 2)-like 3 | NFE2L3 | NM_004289 | 0.015985157 | 1.7023398 |
| 055 | 204790_at | SMAD, mothers against DPP homolog 7 (Drosophila) | SMAD7 | NM_005904 | 0.013379821 | 1.7179344 |
| 056 | 204944_at | protein tyrosine phosphatase, receptor type, G | PTPRG | NM_002841 | 0.004963213 | 1.769544 |
| 057 | 204989_s_at | integrin, beta 4 | ITGB4 | BF305661 | 0.012746719 | 2.1320713 |
| 058 | 205120_s_at | sarcoglycan, beta (43 kDa dystrophin-associated glycoprotein) | SGCB | U29586 | 0.013908542 | 1.7317705 |
| 059 | 205180_s_at | ADAM metallopeptidase domain 8 | ADAM8 | NM_001109 | 0.000473816 | 2.054043 |
| 060 | 205479_s_at | plasminogen activator, urokinase | PLAU | NM_002658 | 0.003415823 | 2.4370956 |
| 061 | 206025_s_at | tumor necrosis factor, alpha-induced protein 6 | TNFAIP6 | AW188195 | 0.013965369 | 2.1515768 |
| 062 | 206113_s_at | RAB5A, member RAS oncogene family | RAB5A | NM_004162 | 0.010821017 | 1.571063 |
| 063 | 206116_s_at | tropomyosin 1 (alpha) | TPM1 | NM_000366 | 0.000283653 | 2.0841253 |
| 064 | 206245_s_at | Influenza virus NS1A binding protein | IVNS1ABP | NM_006469 | 0.003607815 | 1.5105128 |
| 065 | 206323_x_at | oligophrenin 1 | OPHN1 | NM_002547 | 0.018292218 | 1.5056778 |
| 066 | 208510_s_at | peroxisome proliferative activated receptor, gamma | PPARG | NM_015869 | 0.002361554 | 1.882336 |
| 067 | 208613_s_at | filamin B, beta (actin binding protein 278) | FLNB | AV712733 | 0.001033398 | 1.7958127 |
| 068 | 208637_x_at | actinin, alpha 1 | ACTN1 | BC003576 | 0.000448714 | 1.631627 |
| 069 | 208653_s_at | CD164 antigen, sialomucin | CD164 | AF263279 | 0.017487219 | 1.5380286 |
| 070 | 208853_s_at | calnexin | CANX | L18887 | 0.011792572 | 1.5100785 |
| 071 | 209131_s_at | synaptosomal-associated protein, 23 kDa | SNAP23 | U55936 | 0.001730693 | 1.8878508 |
| 072 | 209209_s_at | pleckstrin homology domain containing, family C (with FERM domain) member 1 | PLEKHC1 | AW469573 | 0.009551367 | 1.9820172 |
| 073 | 209314_s_at | HBS1-like (S. cerevisiae) | HBS1L | AK024258 | 0.00507411 | 1.6641864 |
| 074 | 209316_s_at | HBS1-like (S. cerevisiae) | HBS1L | BC001465 | 0.006051209 | 1.6464524 |
| 075 | 209409_at | growth factor receptor-bound protein 10 | GRB10 | DB6962 | 0.01098607 | 1.7481923 |
| 076 | 209410_s_at | growth factor receptor-bound protein 10 | GRB10 | AF000017 | 0.013879589 | 1.701537 |
| 077 | 209537_s_at | exostoses (multiple)-like 2 | EXTL2 | AF000416 | 0.003979554 | 1.5687809 |
| 078 | 210845_s_at | plasminogen activator, urokinase receptor | PLAUR | U08839 | 0.007479298 | 1.7924315 |
| 079 | 210892_s_at | general transcription factor II, i | GTF2I | BC004472 | 0.003141172 | 1.619537 |
| 080 | 210933_s_at | fascin homolog 1, actin-bundling protein (Strongylocentrotus purpuratus) | FSCN1 | BC004908 | 0.00342191 | 1.906748 |
| 081 | 210987_x_at | tropomyosin 1 (alpha) | TPM1 | M19267 | 0.004614187 | 1.6935222 |
| 082 | 211299_s_at | flotillin 2 | FLOT2 | BC003683 | 0.015057402 | 1.5387125 |
| 083 | 211506_s_at | interleukin 8 | IL8 | AF043337 | 0.005428782 | 2.867063 |
| 084 | 211559_s_at | cyclin G2 | CCNG2 | L49506 | 0.010491861 | 1.8367761 |
| 085 | 211599_x_at | met proto-oncogene (hepatocyte growth factor receptor) | MET | U19348 | 0.019789577 | 1.9247686 |
| 086 | 211651_s_at | laminin, beta 1 | LAMB1 | M20206 | 0.000418344 | 1.997547 |
| 087 | 211668_s_at | plasminogen activator, urokinase | PLAU | K03226 | 0.00240352 | 2.8568754 |
| 088 | 211864_s_at | fer-1-like 3, myoferlin (C. elegans) | FER1L3 | AF207990 | 0.011889962 | 1.7860718 |
| 089 | 211924_s_at | plasminogen activator, urokinase receptor | PLAUR | AY029180 | 0.011789334 | 1.8189595 |
| 090 | 211981_at | collagen, type IV, alpha 1 | COL4A1 | NM_001845 | 0.007531395 | 1.8490748 |
| 091 | 212012_at | peroxidasin homolog (Drosophila) | PXDN | BF342851 | 0.016265145 | 1.8463359 |
| 092 | 212660_at | PHD finger protein 15 | PHF15 | AI735639 | 0.007391165 | 1.5595657 |
| 093 | 212720_at | poly(A) polymerase alpha | PAPOLA | AI670847 | 0.016607396 | 1.5904158 |
| 094 | 212907_at | Solute carrier family 30 (zinc transporter), member 1 | SLC30A1 | AI972416 | 0.002460855 | 1.63999 |
| 095 | 213288_at | O-acyltransferase (membrane bound) domain containing 2 | OACT2 | AI761250 | 0.010427832 | 1.6232696 |
| 096 | 213457_at | malignant fibrous histiocytoma amplified sequence 1 | MFHAS1 | BF739959 | 0.003050241 | 1.8505166 |
| 097 | 213624_at | sphingomyelin phosphodiesterase, acid-like 3A | SMPDL3A | AA873600 | 0.005912889 | 1.8562527 |
| 098 | 213742_at | splicing factor, arginine/serine-rich 11 | SFRS11 | AW241752 | 0.006011819 | 1.9170463 |
| 099 | 214121_x_at | PDZ and LIM domain 7 (enigma) | PDLIM7 | AA086229 | 5.50514E−05 | 1.5048952 |
| 100 | 214196_s_at | tripeptidyl peptidase I | TPP1 | AA602532 | 0.015398935 | 1.5939685 |
| 101 | 214544_s_at | synaptosomal-associated protein, 23 kDa | SNAP23 | NM_003825 | 0.003539713 | 1.8040004 |
| 102 | 214581_x_at | tumor necrosis factor receptor superfamily, member 21 | TNFRSF21 | BE568134 | 0.002274355 | 2.2189345 |
| 103 | 214701_s_at | fibronectin 1 | FN1 | AJ276395 | 0.001182322 | 2.071262 |
| 104 | 214866_at | plasminogen activator, urokinase receptor | PLAUR | X74039 | 0.003173471 | 1.7340106 |
| 105 | 214895_s_at | ADAM metallopeptidase domain 10 | ADAM10 | AU135154 | 0.004170008 | 1.9890832 |
| 106 | 215501_s_at | dual specificity phosphatase 10 | DUSP10 | AK022513 | 0.018290011 | 1.5388945 |
| 107 | 216035_x_at | transcription factor 7-like 2 (T-cell specific, HMG-box) | TCF7L2 | AV721430 | 0.000657631 | 1.7091621 |
| 108 | 216511_s_at | transcription factor 7-like 2 (T-cell specific, HMG-box) | TCF7L2 | AJ270770 | 0.004103699 | 1.5264177 |
| 109 | 216915_s_at | protein tyrosine phosphatase, non-receptor type 12 | PTPN12 | S69182 | 0.005493577 | 1.6935816 |
| 110 | 216971_s_at | plectin 1, intermediate filament binding protein 500 kDa | PLEC1 | Z54367 | 0.01826363 | 1.7186335 |
| 111 | 217188_s_at | chromosome 14 open reading frame 1 | C14orf1 | AC007182 | 0.011925477 | 1.6185476 |
| 112 | 217448_s_at | chromosome 14 open reading frame 92 | C14orf92 | AL117508 | 0.007782524 | 1.5433311 |
| 113 | 217492_s_at | similar to Epidermal Langerhans cell protein LCP1 phosphatase and tensin homolog (mutated in multiple advanced cancers 1) | LOC285412 PTEN | AF023139 | 0.007220107 | 1.5624946 |
| 114 | 218000_s_at | pleckstrin homology-like domain, family A, member 1 | PHLDA1 | NM_007350 | 0.016502094 | 1.6960312 |
| 115 | 218077_s_at | zinc finger, DHHC-type containing 3 | ZDHHC3 | BE542551 | 0.01684034 | 1.5417765 |
| 116 | 218078_s_at | zinc finger, DHHC-type containing 3 | ZDHHC3 | NM_016598 | 0.010970607 | 1.5836283 |

TABLE 1-continued

| NO. | Probe Set ID | Gene Name | Gene Symbol | Genbank Accession # | T-test p-value | Fold change (abs) |
|---|---|---|---|---|---|---|
| 117 | 218435_at | DnaJ (Hsp40) homolog, subfamily C, member 15 | DNAJC15 | NM_013238 | 0.019865552 | 1.7292447 |
| 118 | 218644_at | pleckstrin 2 | PLEK2 | NM_016445 | 0.000675608 | 2.7071812 |
| 119 | 218748_s_at | SEC10-like 1 (*S. cerevisiae*) | SEC10L1 | NM_006544 | 0.012352341 | 1.7368068 |
| 120 | 218815_s_at | transmembrane protein 51 | TMEM51 | NM_018022 | 0.000753902 | 1.6477742 |
| 121 | 218826_at | solute carrier family 35, member F2 | SLC35F2 | NM_017515 | 0.009280122 | 1.6340361 |
| 122 | 218854_at | squamous cell carcinoma antigen recognized by T cells 2 | SART2 | NM_013352 | 0.014419112 | 1.6285655 |
| 123 | 218856_at | tumor necrosis factor receptor superfamily, member 21 | TNFRSF21 | NM_016629 | 0.01292243 | 1.617686 |
| 124 | 218885_s_at | UDP-N-acetyl-alpha-D-galactosamine:polypeptide N-acetylgalactosaminyltransferase 12 (GalNAc-T12) | GALNT12 | NM_024642 | 0.014052196 | 1.6402073 |
| 125 | 219410_at | transmembrane protein 45A | TMEM45A | NM_018004 | 0.018847797 | 2.0938365 |
| 126 | 219603_s_at | zinc finger protein 226 | ZNF226 | NM_015919 | 0.005593323 | 1.5408667 |
| 127 | 220199_s_at | chromosome 1 open reading frame 80 | C1orf80 | NM_022831 | 0.016323 | 1.5315142 |
| 128 | 220617_s_at | zinc finger protein 532 | ZNF532 | NM_018181 | 0.001976648 | 1.5441327 |
| 129 | 221268_s_at | sphingosine-1-phosphate phosphatase 1 | SGPP1 | NM_030791 | 0.008873873 | 1.9432548 |
| 130 | 221881_s_at | chloride intracellular channel 4 | CLIC4 | AI638420 | 0.004401053 | 1.7742935 |
| 131 | 222399_s_at | SM-11044 binding protein | SMBP | BG104571 | 0.00011337 | 1.5270268 |
| 132 | 222449_at | tranamembrane, prostate androgen induced RNA | TMEPAI | AL035541 | 0.005303006 | 2.2757804 |
| 133 | 222528_s_at | solute carrier family 25, member 37 | SLC25A37 | BG251467 | 0.014745607 | 1.738053 |
| 134 | 222540_s_at | hepatitis B virus x associated protein | HBXAP | BG286920 | 0.005694628 | 1.5068418 |
| 135 | 222692_s_at | fibronectin type III domain containing 3B | FNDC3B | BF444916 | 0.001075083 | 1.5835624 |
| 136 | 222693_at | fibronectin type III domain containing 3B | FNDC3B | BF444916 | 0.000622161 | 1.7766397 |
| 137 | 222773_s_at | UDP-N-acetyl-alpha-D-galactosamine:polypeptide N-acetylgalactosaminyltransferase 12 (GalNAc-T12) | GALNT12 | AA554045 | 0.003090952 | 1.8790901 |
| 138 | 223577_x_at | PRO1073 protein | PRO1073 | AA827878 | 0.003659447 | 1.6790042 |
| 139 | 223940_x_at | metastasis associated lung adenocarcinoma transcript 1 (non-coding RNA) | MALAT1 | AF132202 | 0.016841894 | 1.9524238 |
| 140 | 224558_s_at | metastasis associated lung adenocarcinoma transcript 1 (non-coding RNA) | MALAT1 | AI446756 | 0.012874936 | 1.6367766 |
| 141 | 224674_at | tweety homolog 3 (*Drosophila*) | TTYH3 | AI934753 | 0.002428954 | 1.6452742 |
| 142 | 224733_at | chemokine-like factor superfamily 3 | CKLFSF3 | AL574900 | 0.013543638 | 1.5199631 |
| 143 | 224802_at | Nedd4 family interacting protein 2 | NDFIP2 | AA019338 | 0.013437813 | 1.5261155 |
| 144 | 225021_at | zinc finger protein 532 | ZNF532 | AA861416 | 0.002285053 | 1.6213596 |
| 145 | 225140_at | Kruppel-like factor 3 (basic) | KLF3 | BF438116 | 0.016804362 | 1.5368354 |
| 146 | 225168_at | FERM domain containing 4A | FRMD4A | T78406 | 0.006987929 | 1.5712297 |
| 147 | 225424_at | glycerol-3-phosphate acyltransferase, mitochondrial | GPAM | AB046780 | 0.000390623 | 1.7006425 |
| 148 | 225503_at | dehydrogenase/reductase (SDR family) X-linked | DHRSX | AL547782 | 0.005000754 | 1.770981 |
| 149 | 225567_at | Hypothetical LOC388114 | LOC388114 | BE207755 | 0.003047524 | 1.6990312 |
| 150 | 225609_at | glutathione reductase | GSR | AI888037 | 0.004693668 | 1.8490914 |
| 151 | 225842_at | Pleckstrin homology-like domain, family A, member 1 | PHLDA1 | AK026181 | 0.014052763 | 1.8735564 |
| 152 | 226084_at | microtubule-associated protein 1B | MAP1B | AA554833 | 0.016480966 | 1.9064581 |
| 153 | 226352_at | Junction-mediating and regulatory protein | JMY | BF447037 | 0.001219355 | 1.5196482 |
| 154 | 226726_at | O-acyltransferase (membrane bound) domain containing 2 | OACT2 | W63676 | 0.005363467 | 1.8277074 |
| 155 | 226780_s_at | hypothetical protein HSPC268 | HSPC268 | BF540829 | 0.001859941 | 1.5185972 |
| 156 | 227257_s_at | chromosome 10 open reading frame 46 | C10orf46 | AW973842 | 0.000646104 | 1.6094143 |
| 157 | 227628_at | similar to RIKEN cDNA 2310016C16 | LOC493869 | AL571557 | 0.006222301 | 2.0978951 |
| 158 | 227808_at | DnaJ (Hsp40) homolog, subfamily C, member 15 | DNAJC15 | AI091398 | 0.01153802 | 1.7936606 |
| 159 | 230206_at | Dedicator of cytokinesis 5 | DOCK5 | AI692645 | 0.005127667 | 1.6694399 |
| 160 | 231735_s_at | PRO1073 protein | PRO1073 | NM_014086 | 0.004784999 | 1.72546 |
| 161 | 231823_s_at | KIAA1295 | KIAA1295 | BG054798 | 0.002478401 | 1.5713933 |
| 162 | 235587_at | hypothetical protein LOC202781 | LOC202781 | BG400596 | 0.018314553 | 1.5202585 |
| 163 | 235879_at | Muscleblind-like (*Drosophila*) | MBNL1 | AI697540 | 0.002645486 | 2.0540323 |
| 164 | 238558_at | Muscleblind-like (*Drosophila*) | MBNL1 | AI445833 | 0.004576562 | 1.805269 |
| 165 | 238563_at | Abl-interactor 1 | ABI1 | AV762916 | 0.012934915 | 1.6069295 |
| 166 | 238701_x_at | FLJ45803 protein | FLJ45803 | BE176566 | 0.01719282 | 1.5133282 |

The gene expression pattern of the lung cancer cell classified into adenocarcinoma after lung cancer tissue removal operation is analyzed through a hybridization with the probe on the microarray, and a marker gene that is determined to have a difference in an expression level between a patient with lung cancer recurrence within one year (recurrence group) and a patient without lung cancer recurrence even after three years (non-recurrence group) is selected. The results are shown in Table 2 below. A total number of adenocarcinoma patients was 23. Among them, the number of patients with lung cancer recurrence within one year after lung cancer tissue removal operation was 8, and the number of patients without lung cancer recurrent even after three years was 15.

The gene expression pattern of the lung cancer cell classified into squamous cell carcinoma after lung cancer tissue removal operation is analyzed through a hybridization with the probe on the microarray, and a marker gene that is determined to have a difference in an expression level between a patient with lung cancer recurrence within one year (recurrence group) and a patient without lung cancer recurrence even after three years (non-recurrence group) is selected. The results are shown in Table 3 below. A total number of squamous cell carcinoma patients was 37. Among them, the number of patients with lung cancer recurrence within one year after lung cancer tissue removal operation was 11, and the number of patients without lung cancer recurrent even after three years was 26.

TABLE 2

| NO | Probe Set ID | Gene Name | Gene Symbol | Genbank Accession # | T-test p-value | Fold change (abs) |
|---|---|---|---|---|---|---|
| 001 | 1553105_s_at | desmoglein 2 | DSG2 | NM_001943 | 0.01 | 5.339528 |
| 002 | 1553589_a_at | PDZK1 interacting protein 1 | PDZK1IP1 | NM_005764 | 0.02 | 3.608417 |
| 003 | 1553768_a_at | discoidln, CUB and LCCL domain containing 1 | DCBLD1 | NM_173674 | 0.01 | 1.9046342 |
| 004 | 1553928_at | ELMO domain containing 2 | ELMOD2 | NM_153702 | 0.02 | 1.7168769 |
| 005 | 1554327_a_at | calcium activated nucleotidase 1 | CANT1 | AF328554 | 0.01 | 1.6306834 |
| 006 | 1558685_a_at | hypothetical protein BC009467 | LOC158980 | BC009467 | 0.03 | 1.6841992 |
| 007 | 1559399_s_at | zinc finger, CCHC domain containing 10 | ZCCHC10 | BC015988 | 0.02 | 1.5219704 |
| 008 | 1568578_s_at | FGFR1 oncogene partner | FGFR1OP | BC037785 | 0.01 | 2.4856193 |
| 009 | 160020_at | matrix metallopeptidase 14 (membrane-inserted) | MMP14 | Z48481 | 0.03 | 1.8354192 |
| 010 | 200730_s_at | protein tyrosine phosphatase type IVA, member 1 | PTP4A1 | BF576710 | 0.03 | 2.6575127 |
| 011 | 200733_s_at | protein tyrosine phosphatase type IVA, member 1 | PTP4A1 | U48296 | 0.02 | 1.5593889 |
| 012 | 200864_s_at | RAB11A, member RAS oncogene family | RAB11A | NM_004663 | 0.02 | 1.6270655 |
| 013 | 200890_s_at | signal sequence receptor, alpha (translocon-associated protein alpha) | SSR1 | AW006345 | 0.01 | 1.8127153 |
| 014 | 200931_s_at | vinculin | VCL | NM_014000 | 0.01 | 1.7692009 |
| 015 | 201011_at | ribophorin I | RPN1 | NM_002950 | 0.01 | 1.6075972 |
| 016 | 201106_at | glutathione peroxidase 4 (phospholipid hydroperoxidase) | GPX4 | NM_002085 | 0.02 | 1.6833277 |
| 017 | 201143_s_at | eukaryotic translation initiation factot 2. subunit 1 alpha, 35 kDa | EIF2S1 | BC002513 | 0.02 | 2.298374 |
| 018 | 201207_at | tumor necrosis factor, alpha-induced protein 1 (endothelial) | TNFAIP1 | NM_021137 | 0.01 | 1.6828994 |
| 019 | 201250_s_at | solute carrier family 2 (facilitated glucose transporter), member 1 | SLC2A1 | NM_006516 | 0.02 | 4.009399 |
| 020 | 201392_s_at | insulin-like growth factor 2 receptor | IGF2R | BG031974 | 0.02 | 1.6488191 |
| 021 | 201393_s_at | insulin-like growth factor 2 receptor | IGF2R | NM_000876 | 0.02 | 1.5784883 |
| 022 | 201456_s_at | BUB3 budding uninhibited by benzimidazoles 3 homolog (yeast) | BUB3 | AU160695 | 0.01 | 1.7238452 |
| 023 | 201458_s_at | BUB3 budding uninhibited by benzimidazoles 3 homolog (yeast) | BUB3 | NM_004725 | 0.01 | 1.5530633 |
| 024 | 201525_at | apolipoprotein D | APOD | NM_001647 | 0.03 | 4.186704 |
| 025 | 201564_s_at | fascin homolog 1, actin-bundling protein (Strongylocentrotus purpuratus) | FSCN1 | NM_003088 | 0.01 | 3.2328043 |
| 026 | 201631_s_at | immediate early response 3 | IER3 | NM_003897 | 0.01 | 3.0016828 |
| 027 | 201656_at | integrin, alpha 6 | ITGA6 | NM_000210 | 0.02 | 2.3616688 |
| 028 | 201700_at | cyclin D3 | CCND3 | NM_001760 | 0.02 | 1.6460308 |
| 029 | 202047_s_at | chromobox homolog 6 | CBX6 | AI458128 | 0.01 | 1.9611783 |
| 030 | 202048_s_at | chromobox homolog 6 | CBX6 | NM_014292 | 0.02 | 1.6010046 |
| 031 | 202086_at | myxovirus (influenza virus) resistance 1, interferon-inducible protein p78 (mouse) | MX1 | NM_002462 | 0.02 | 2.4754105 |
| 032 | 202130_at | RIO kinase 3 (yeast) | RIOK3 | AA725102 | 0.01 | 1.6167943 |
| 033 | 202131_s_at | RIO kinase 3 (yeast) | RIOK3 | NM_003831 | 0.02 | 1.7833867 |
| 034 | 202233_s_at | ubiquinol-cytochrome c reductase hinge protein | UQCRH | NM_006004 | 0.01 | 1.5353662 |
| 035 | 202267_at | laminin, gamma 2 | LAMC2 | NM_005562 | 0.01 | 3.9229517 |
| 036 | 202293_at | stromal antigen 1 | STAG1 | AW168948 | 0.01 | 1.7993419 |
| 037 | 202604_x_at | ADAM metallopeptidase domain 10 | ADAM10 | NM_001110 | 0.02 | 2.0231702 |
| 038 | 202696_at | oxidative-stress responsive 1 | OXSR1 | NM_005109 | 0.01 | 1.5418515 |
| 039 | 202816_s_at | synovial sarcoma translocation, chromosome 18 | SS18 | AW292882 | 0.01 | 2.0899003 |
| 040 | 202856_s_at | solute carrier family 16 (monocarboxylic acid transporters), member 3 | SLC16A3 | NM_004207 | 0.01 | 2.8914852 |
| 041 | 202869_at | 2',5'-oligoadenylate synthetase 1, 40/46 kDa | OAS1 | NM_016816 | 0.02 | 3.431309 |
| 042 | 202887_s_at | DNA-damage-inducible transcript 4 | DDIT4 | NM_019058 | 0.02 | 2.74081 |
| 043 | 202904_s_at | LSM5 homolog, U6 small nuclear RNA associated (S. cerevisiae) | LSM5 | NM_012322 | 0.03 | 1.8907431 |
| 044 | 202934_at | hexokinase 2 | HK2 | AI761561 | 0.01 | 2.1517375 |
| 045 | 203072_at | myosin IE | MYO1E | NM_004998 | 0.01 | 2.039332 |
| 046 | 203177_x_at | transcription factor A, mitochondrial | TFAM | NM_003201 | 0.01 | 1.8601428 |
| 047 | 203256_at | cadherin 3, type 1, P-cadherin (placental) | CDH3 | NM_001793 | 0.01 | 2.6757588 |
| 048 | 203287_at | ladinin 1 | LAD1 | NM_005558 | 0.03 | 1.9237865 |
| 049 | 203311_s_at | ADP-ribosylation factor 6 | ARF6 | M57763 | 0.02 | 1.9452083 |
| 050 | 203313_s_at | TGFB-induced factor (TALE family homeobox) | TGIF | NM_003244 | 0.02 | 1.5528815 |
| 051 | 203344_s_at | retinoblastoma binding protein 8 | RBBP8 | NM_002894 | 0.01 | 1.7286093 |
| 052 | 203395_s_at | hairy and enhancer of split 1, (Drosophila) | HES1 | NM_005524 | 0.02 | 1.6101321 |
| 053 | 203430_at | heme binding protein 2 | HEBP2 | NM_014320 | 0.02 | 1.822933 |
| 054 | 203476_at | trophoblast glycoprotein | TPBG | NM_006670 | 0.03 | 2.0313597 |
| 055 | 203499_at | EPH receptor A2 | EPHA2 | NM_004431 | 0.02 | 2.4758015 |
| 056 | 203501_at | plasma glutamate carboxypeptidase | PGCP | NM_006102 | 0.02 | 1.742001 |
| 057 | 203535_at | S100 calcium binding protein A9 (calgranulin B) | S100A9 | NM_002965 | 0.02 | 5.647521 |
| 058 | 203554_x_at | pituitary tumor-transforming 1 | PTTG1 | NM_004219 | 0.02 | 2.1384234 |
| 059 | 203642_s_at | COBL-like 1 | COBLL1 | NM_014900 | 0.02 | 1.7199888 |
| 060 | 203690_at | tubulin, gamma complex associated protein 3 | TUBGCP3 | NM_006322 | 0.01 | 1.6228286 |
| 061 | 203906_at | IQ motif and Sec7 domain 1 | IQSEC1 | AI652645 | 0.01 | 1.7168043 |
| 062 | 203964_at | N-myc (and STAT) interactor | NMI | NM_004688 | 0.01 | 1.8720082 |
| 063 | 203988_s_at | fucosyltransferase 8 (alpha (1,6) fucosyltransferase) | FUT8 | NM_004480 | 0.01 | 2.0948534 |
| 064 | 204136_at | collagen, type VII, alpha 1 (epidermolysis bullosa, dystrophic, dominant and recessive) | COL7A1 | NM_000094 | 0.01 | 2.2071517 |

TABLE 2-continued

| NO | Probe Set ID | Gene Name | Gene Symbol | Genbank Accession # | T-test p-value | Fold change (abs) |
|---|---|---|---|---|---|---|
| 065 | 204401_at | potassium intermediate/small conductance calcium-activated channel, subfamily N, member 4 | KCNN4 | NM_002250 | 0.01 | 3.260382 |
| 066 | 204415_at | interferon, alpha-inducible protein (clone IFI-6-16) | G1P3 | NM_022873 | 0.02 | 4.0747566 |
| 067 | 204470_at | chemokine (C-X-C motif) ligand 1 (melanoma growth stimulating activity, alpha) | CXCL1 | NM_001511 | 0.01 | 6.7313213 |
| 068 | 204580_at | matrix metallopeptidase 12 (macrophage elastase) | MMP12 | NM_002426 | 0.02 | 7.360193 |
| 069 | 204587_at | solute carrier family 25 (mitochondrial carrier, brain), member 14 | SLC25A14 | NM_003951 | 0.02 | 1.5086871 |
| 070 | 204616_at | ubiquitin carboxyl-terminal esterase L3 (ubiquitin thiolesterase) | UCHL3 | NM_006002 | 0.03 | 1.8766123 |
| 071 | 204635_at | ribosomal protein S6 kinase, 90 kDa, polypeptide 5 | RPS6KA5 | NM_004755 | 0.01 | 1.853935 |
| 072 | 204747_at | interferon-induced protein with tetratricopeptide repeats 3 | IFIT3 | NM_001549 | 0.02 | 2.588765 |
| 073 | 204809_at | ClpX caseinolytic peptidase X homolog (E. coli) | CLPX | NM_006660 | 0.02 | 1.5264844 |
| 074 | 204857_at | MAD1 mitotic arrest deficient-like 1 (yeast) | MAD1L1 | NM_003550 | 0.03 | 1.6594671 |
| 075 | 204875_s_at | GDP-mannose 4,6-dehydratase | GMDS | NM_001500 | 0.02 | 2.5758607 |
| 076 | 204990_s_at | integrin, beta 4 | ITGB4 | NM_000213 | 0.01 | 3.176456 |
| 077 | 205004_at | NF-kappaB repressing factor | NKRF | NM_017544 | 0.02 | 1.5878501 |
| 078 | 205117_at | transforming growth factor, alpha | TGFA | NM_003236 | 0.01 | 2.1914852 |
| 079 | 205120_s_at | sarcoglycan, beta (43 kDa dystrophin-associated glycoprotein) | SGCB | U29586 | 0.02 | 2.5721073 |
| 080 | 205157_s_at | keratin 17 | KRT17 | NM_000422 | 0.01 | 5.252511 |
| 081 | 205180_s_at | ADAM metallopeptidase domain 8 | ADAM8 | NM_001109 | 0.01 | 2.1361954 |
| 082 | 205202_at | protein-L-isoaspartate (D-aspartate) O-methyltransferase | PCMT1 | NM_005389 | 0.01 | 1.5924072 |
| 083 | 205339_at | TAL1 (SCL) interrupting locus | SIL | NM_003035 | 0.02 | 2.043193 |
| 084 | 205455_at | macrophage stimulating 1 receptor (c-met-related tyrosine kinase) | MST1R | NM_002447 | 0.02 | 2.835629 |
| 085 | 205479_s_at | plasminogen activator, urokinase | PLAU | NM_002658 | 0.01 | 3.8200433 |
| 086 | 205518_s_at | cytidine monophosphate-N-acetylneuraminic acid hydroxy (CMP-N-acetylneuraminate monooxygenase) | CMAH | NM_003570 | 0.01 | 2.596108 |
| 087 | 205945_at | interleukin 6 receptor | IL6R | NM_000565 | 0.03 | 1.8261979 |
| 088 | 206055_s_at | small nuclear ribonucleoprotein polypeptide A' | SNRPA1 | NM_003090 | 0.01 | 1.5232844 |
| 089 | 206323_x_at | oligophrenin 1 | OPHN1 | NM_002547 | 0.01 | 2.3268037 |
| 090 | 206414_s_at | development and differentiation enhancing factor 2 | DDEF2 | NM_003887 | 0.01 | 2.089077 |
| 091 | 207079_s_at | mediator of RNA polymerase II transcription, subunit 6 homolog (yeast) | MED6 | NM_005466 | 0.03 | 1.8905708 |
| 092 | 207850_at | chemokine (C-X-C motif) ligand 3 | CXCL3 | NM_002090 | 0.02 | 4.294934 |
| 093 | 208091_s_at | EGFR-coamplified and overexpressed protein | ECOP | NM_030796 | 0.02 | 2.2340379 |
| 094 | 208613_s_at | filamin B, beta (actin binding protein 278) | FLNB | AV712733 | 0.02 | 2.3647172 |
| 095 | 208636_at | Actinin, alpha 1 | ACTN1 | AI082078 | 0.01 | 1.8102713 |
| 096 | 208637_x_at | actinin, alpha 1 | ACTN1 | BC003576 | 0.01 | 2.062581 |
| 097 | 208819_at | RAB8A, member RAS oncogene family | RAB8A | BC002977 | 0.01 | 1.6729795 |
| 098 | 208840_s_at | Ras-GTPase activating protein SH3 domain-binding protein 2 | G3BP2 | AU149503 | 0.02 | 1.8072606 |
| 099 | 208875_s_at | p21 (CDKN1A)-activated kinase 2 | PAK2 | BF796470 | 0.01 | 2.1095228 |
| 100 | 208876_s_at | p21 (CDKN1A)-activated kinase 2 | PAK2 | AI076186 | 0.02 | 1.6706929 |
| 101 | 208878_s_at | p21 (CDKN1A)-activated kinase 2 | PAK2 | AF092132 | 0.01 | 1.5662557 |
| 102 | 209022_at | stromal antigen 2 | STAG2 | AK026678 | 0.01 | 1.5019888 |
| 103 | 209025_s_at | synaptotagmin binding, cytoplasmic RNA interacting protein | SYNCRIP | AF037448 | 0.01 | 1.748127 |
| 104 | 209314_s_at | HBS1-like (S. cerevisiae) | HBS1L | AK024258 | 0.01 | 2.2400491 |
| 105 | 209417_s_at | interferon-induced protein 35 | IFI35 | BC001356 | 0.02 | 1.9908478 |
| 106 | 209476_at | thioredoxin domain containing | TXNDC | AL080080 | 0.02 | 1.5641398 |
| 107 | 209487_at | RNA binding protein with multiple splicing | RBPMS | D84109 | 0.02 | 1.5929683 |
| 108 | 209537_at | exostoses (multiple)-like 2 | EXTL2 | AF000416 | 0.03 | 2.019564 |
| 109 | 209627_s_at | oxysterol binding protein-like 3 | OSBPL3 | AY008372 | 0.03 | 1.9842228 |
| 110 | 209791_at | peptidyl arginine deiminase, type II | PADI2 | AL049569 | 0.02 | 1.5902214 |
| 111 | 210092_at | mago-nashi homolog, proliferation-associated (Drosophila) | MAGOH | AF067173 | 0.03 | 1.7290384 |
| 112 | 210093_s_at | mago-nashi homolog, proliferation-associated (Drosophila) | MAGOH | AF067173 | 0.01 | 1.5214177 |
| 113 | 210104_at | mediator of RNA polymerase II transcription, subunit 6 homolog (yeast) | MED6 | AF074723 | 0.01 | 1.7416326 |
| 114 | 210273_at | BH-protocadherin (brain-heart) | PCDH7 | AB006757 | 0.03 | 1.5068512 |
| 115 | 210933_s_at | fascin homolog 1, actin-bundling protein (Strongylocentrotus purpuratus) | FSCN1 | BC004908 | 0.01 | 2.660472 |
| 116 | 211160_x_at | actinin, alpha 1 | ACTN1 | M95178 | 0.01 | 1.6758434 |
| 117 | 211668_s_at | plasminogen activator, urokinase | PLAU | K03226 | 0.03 | 4.548989 |
| 118 | 211737_x_at | pleiotrophin (heparin binding growth factor 8, neurite growth-promoting factor 1) | PTN | BC005916 | 0.02 | 2.2613049 |
| 119 | 212203_x_at | interferon induced transmembrane protein 3 (1-8U) | IFITM3 | BF338947 | 0.01 | 1.5134683 |
| 120 | 212221_x_at | iduronate 2-sulfatase (Hunter syndrome) | IDS | AV703259 | 0.01 | 1.8884305 |
| 121 | 212236_x_at | keratin 17 | KRT17 | Z19574 | 0.01 | 3.7909358 |
| 122 | 212268_at | serpin peptidase inhibitor, clade B (ovalbumin), member 1 | SERPINB1 | NM_030666 | 0.02 | 1.9949495 |
| 123 | 212312_at | BCL2-like 1 | BCL2L1 | AL117381 | 0.02 | 1.5705433 |
| 124 | 212322_at | sphingosine-1-phosphate lyase 1 | SGPL1 | BE999972 | 0.01 | 1.6549215 |
| 125 | 212330_at | transcription factor Dp-1 | TFDP1 | R60866 | 0.02 | 2.1620867 |
| 126 | 212531_at | lipacalin 2 (oncogene 24p3) | LCN2 | NM_005564 | 0.02 | 6.2857018 |
| 127 | 212657_s_at | interleukin 1 receptor antagonist | IL1RN | U65590 | 0.01 | 3.7755005 |
| 128 | 212858_at | progestin and adipoQ receptor family member IV | PAQR4 | AL520675 | 0.01 | 2.2580597 |
| 129 | 212992_at | chromosome 14 open reading frame 78 | C14orf78 | AI935123 | 0.01 | 5.9573503 |
| 130 | 213088_s_at | DnaJ (Hsp40) homolog, subfamily C, member 9 | DNAJC9 | BE551340 | 0.02 | 1.784215 |
| 131 | 213288_at | O-acyltransferase (membrane bound) domain containing 2 | OACT2 | AI761250 | 0.02 | 2.1144574 |

TABLE 2-continued

| NO | Probe Set ID | Gene Name | Gene Symbol | Genbank Accession # | T-test p-value | Fold change (abs) |
|---|---|---|---|---|---|---|
| 132 | 214121_x_at | PDZ and LIM domain 7 (enigma) | PDLIM7 | AA086229 | 0.01 | 1.7699668 |
| 133 | 214453_s_at | interferon-induced protein 44 | IFI44 | NM_006417 | 0.03 | 2.8858101 |
| 134 | 214697_s_at | ROD1 regulator of differentiation 1 (S. pombe) | ROD1 | AW190873 | 0.01 | 2.048636 |
| 135 | 214974_x_at | chemokine (C-X-C motif) ligand 5 | CXCL5 | AK026546 | 0.02 | 6.4936213 |
| 136 | 215223_s_at | superoxide dismutase 2, mitochondrial | SOD2 | W46388 | 0.01 | 3.1782749 |
| 137 | 215230_x_at | eukaryotic translation initiation factor 3, subunit 8, 110 kDa | EIF3S8 | AA679705 | 0.02 | 1.6019442 |
| 138 | 215411_s_at | TRAF3 interacting protein 2 | TRAF3IP2 | AL008730 | 0.03 | 1.72815 |
| 139 | 216153_x_at | reversion-inducing-cysteine-rich protein with kazal motifs | RECK | AK022897 | 0.01 | 1.9417262 |
| 140 | 216841_s_at | superoxide dismutase 2, mitochondrial | SOD2 | X15132 | 0.01 | 2.8182118 |
| 141 | 216905_s_at | suppression of tumorigenicity 14 (colon carcinoma, matriptase, epithin) | ST14 | U20428 | 0.02 | 1.8127093 |
| 142 | 216977_x_at | small nuclear ribonucleoprotein polypeptide A' | SNRPA1 | AJ130972 | 0.01 | 1.5991035 |
| 143 | 217834_s_at | synaptotagmin binding, cytoplasmic RNA interacting protein | SYNCRIP | NM_006372 | 0.03 | 1.7178055 |
| 144 | 217867_x_at | beta-site APP-cleaving enzyme 2 | BACE2 | NM_012105 | 0.02 | 2.5611665 |
| 145 | 217901_at | Desmoglein 2 | DSG2 | BF031829 | 0.01 | 3.4549432 |
| 146 | 218012_at | TSPY-like 2 | TSPYL2 | NM_022117 | 0.01 | 1.6316599 |
| 147 | 218288_s_at | hypothetical protein MDS025 | MDS025 | NM_021825 | 0.01 | 1.7013886 |
| 148 | 218294_s_at | nucleoporin 50 kDa | NUP50 | AF267865 | 0.01 | 1.5833666 |
| 149 | 218400_at | 2'-5'-oligoadenylate synthetase 3, 100 kDa | OAS3 | NM_006187 | 0.01 | 3.0217175 |
| 150 | 218451_at | CUB domain containing protein 1 | CDCP1 | NM_022842 | 0.01 | 3.0102131 |
| 151 | 218460_at | hypothetical protein FLJ20397 | FLJ20397 | NM_017802 | 0.01 | 1.6881874 |
| 152 | 218498_s_at | ERO1-like (S. cerevisiae) | ERO1L | NM_014584 | 0.01 | 2.5205412 |
| 153 | 218573_at | melanoma antigen family H, 1 | MAGEH1 | NM_014061 | 0.01 | 1.6212198 |
| 154 | 218585_s_at | denticleless homolog (Drosophila) | DTL | NM_016448 | 0.03 | 2.4223747 |
| 155 | 218644_at | pleckstrin 2 | PLEK2 | NM_016445 | 0.01 | 4.898943 |
| 156 | 218796_at | chromosome 20 open reading frame 42 | C20orf42 | NM_017671 | 0.03 | 3.3694396 |
| 157 | 218826_at | solute carrier family 35, member F2 | SLC35F2 | NM_017515 | 0.03 | 2.0183008 |
| 158 | 218943_s_at | DEAD (Asp-Glu-Ala-Asp) box polypeptide 58 | DDX58 | NM_014314 | 0.02 | 2.4575703 |
| 159 | 218950_at | centaurin, delta 3 | CENTD3 | NM_022841 | 0.02 | 1.5173771 |
| 160 | 219146_at | chromosome 17 open reading frame 42 | C17orf42 | NM_024683 | 0.01 | 1.5234692 |
| 161 | 219296_at | zinc finger, DHHC-type containing 13 | ZDHHC13 | NM_019028 | 0.03 | 1.5033884 |
| 162 | 219303_at | chromosome 13 open reading frame 7 | C13orf7 | NM_024546 | 0.03 | 1.5534021 |
| 163 | 219332_at | MICAL-like 2 | MICAL-L2 | NM_024723 | 0.02 | 1.8410143 |
| 164 | 219399_at | lin-7 homolog C (C. elegans) | LIN7C | NM_018362 | 0.03 | 1.5852816 |
| 165 | 219421_at | osmosis responsive factor | OSRF | NM_012382 | 0.01 | 1.531867 |
| 166 | 219439_at | core 1 synthase, glycoprotein-N-acetylgalactosamine 3-beta-galactosyltransferase, 1 | C1GALT1 | NM_020156 | 0.02 | 2.2143774 |
| 167 | 219517_at | elongation factor RNA polymerase II-like 3 | ELL3 | NM_025165 | 0.02 | 1.6594616 |
| 168 | 219549_s_at | reticulon 3 | RTN3 | NM_006054 | 0.02 | 1.6491096 |
| 169 | 219603_s_at | zinc finger protein 226 | ZNF226 | NM_015919 | 0.01 | 1.8911394 |
| 170 | 219630_s_at | PDZK1 interacting protein 1 | PDZK1IP1 | NM_005764 | 0.02 | 3.5720232 |
| 171 | 219691_at | sterile alpha motif domain containing 9 | SAMD9 | NM_017654 | 0.02 | 2.2009485 |
| 172 | 219787_s_at | epithelial cell transforming sequence 2 oncogene | ECT2 | NM_018098 | 0.02 | 3.414079 |
| 173 | 219799_s_at | dehydrogenase/reductase (SDR family) member 9 | DHRS9 | NM_005771 | 0.02 | 1.7866958 |
| 174 | 219959_at | molybdenum cofactor sulfurase | MOCOS | NM_017947 | 0.01 | 3.192601 |
| 175 | 220232_at | stearoyl-CoA desaturase 5 | SCD5 | NM_024906 | 0.02 | 3.2719014 |
| 176 | 220368_s_at | KIAA2010 | KIAA2010 | NM_017936 | 0.02 | 1.6052217 |
| 177 | 220725_x_at | Dynein, axonemal, heavy polypeptide 3 | DNAH3 | NM_025095 | 0.01 | 1.8525391 |
| 178 | 221477_s_at | hypothetical protein MGC5618 | MGC5618 | BF575213 | 0.01 | 2.2014346 |
| 179 | 221482_s_at | cyclic AMP phosphoprotein, 19 kD | ARPP-19 | BC003418 | 0.02 | 1.711658 |
| 180 | 221732_at | calcium activated nucleotidase 1 | CANT1 | AK026161 | 0.02 | 1.6711121 |
| 181 | 221752_at | Slingshot homolog 1 (Drosophila) | SSH1 | AL041728 | 0.02 | 1.678051 |
| 182 | 221922_at | G-protein signalling modulator 2 (AGS3-like, C. elegans) | GPSM2 | AW195581 | 0.01 | 2.2638144 |
| 183 | 222392_x_at | PERP, TP53 apoptosis effector | PERP | AJ251280 | 0.02 | 1.8814404 |
| 184 | 222399_s_at | SM-11044 binding protein | SMBP | BG104571 | 0.02 | 1.6986449 |
| 185 | 222424_s_at | nuclear casein kinase and cyclin-dependent kinase substrate 1 | NUCKS1 | BC000805 | 0.01 | 1.6469624 |
| 186 | 222446_s_at | beta-site APP-cleaving enzyme 2 | BACE2 | AF178532 | 0.01 | 1.9711965 |
| 187 | 222492_at | pyridoxal (pyridoxine, vitamin B6) kinase | PDXK | AW262867 | 0.01 | 1.5873553 |
| 188 | 222502_s_at | ubiquitin-fold modifier 1 | UFM1 | BC005193 | 0.01 | 1.7238611 |
| 189 | 222523_at | SUMO1/sentrin/SMT3 specific peptidase 2 | SENP2 | BE622841 | 0.03 | 1.7830018 |
| 190 | 222528_s_at | solute carrier family 25, member 37 | SLC25A37 | BG251467 | 0.02 | 2.6761055 |
| 191 | 222561_at | LanC lantibiotic synthetase component C-like 2 (bacterial) | LANCL2 | AJ278245 | 0.03 | 2.2797666 |
| 192 | 222587_s_at | UDP-N-acetyl-alpha-D-galactosamine:polypeptide N-acetylgalactosaminyltransferase 7(GalNAc-T7) | GALNT7 | BF699855 | 0.03 | 1.7439753 |
| 193 | 222689_at | phytoceramidase, alkaline | PHCA | N51263 | 0.01 | 1.7877864 |
| 194 | 222692_s_at | fibronectin type III domain containing 3B | FNDC3B | BF444916 | 0.01 | 1.9685304 |
| 195 | 222693_at | fibronectin type III domain containing 3B | FNDC3B | BF444916 | 0.02 | 2.1501522 |
| 196 | 222793_at | DEAD (Asp-Glu-Ala-Asp) box polypeptide 58 | DDX58 | AK023661 | 0.01 | 2.2502613 |
| 197 | 223219_s_at | CCR4-NOT transcription complex, subunit 10 | CNOT10 | BC002931 | 0.01 | 1.5173706 |
| 198 | 223278_at | gap junction protein, beta 2, 26 kDa (connexin 26) | GJB2 | M86849 | 0.01 | 5.1083236 |
| 199 | 223374_s_at | UDP-Gal:betaGlcNAc beta 1,3-galactosyltransferase, polypeptide 3 | B3GALT3 | AF154848 | 0.02 | 2.124231 |
| 200 | 223421_at | cysteine/histidine-rich 1 | CYHR1 | BC005073 | 0.01 | 1.7838429 |
| 201 | 223467_at | RAS, dexamethasone-induced 1 | RASD1 | AF069506 | 0.01 | 3.1274104 |
| 202 | 223626_x_at | family with sequence similarity 14, member A | FAM14A | AF208232 | 0.01 | 1.5701514 |
| 203 | 223631_s_at | chromosome 19 open reading frame 33 | C19orf33 | AF213678 | 0.02 | 3.90325 |

TABLE 2-continued

| NO | Probe Set ID | Gene Name | Gene Symbol | Genbank Accession # | T-test p-value | Fold change (abs) |
|---|---|---|---|---|---|---|
| 204 | 224159_x_at | tripartite motif-containing 4 | TRIM4 | AF220023 | 0.01 | 2.2881489 |
| 205 | 224493_x_at | chromosome 18 open reading frame 45 | C18orf45 | BC006280 | 0.02 | 1.571958 |
| 206 | 224494_x_at | dehydrogenase/reductase (SDR family) member 10 | DHRS10 | BC006283 | 0.02 | 1.9102337 |
| 207 | 224564_s_at | reticulon 3 | RTN3 | BE544689 | 0.01 | 1.583082 |
| 208 | 224595_at | solute carrier family 44, member 1 | SLC44A1 | AK022549 | 0.02 | 1.601491 |
| 209 | 224596_at | solute carrier family 44, member 1 | SLC44A1 | AI634866 | 0.01 | 1.5728544 |
| 210 | 224598_at | mannosyl (alpha-1,3-)-glycoprotein beta-1,4-N-acetylglucosaminyltransferase, isoenzyme B | MGAT4B | BF570193 | 0.03 | 1.5535489 |
| 211 | 224674_at | tweety homolog 3 (*Drosophila*) | TTYH3 | AI934753 | 0.02 | 2.123153 |
| 212 | 224675_at | mesoderm development candidate 2 | MESDC2 | AK026606 | 0.01 | 1.6605617 |
| 213 | 224679_at | mesoderm development candidate 2 | MESDC2 | BE963495 | 0.01 | 1.65804 |
| 214 | 224681_at | guanine nucleotide binding protein (G protein) alpha 12 | GNA12 | BG028884 | 0.01 | 1.6103705 |
| 215 | 224799_at | Nedd4 family interacting protein 2 | NDFIP2 | AW290956 | 0.02 | 1.9774225 |
| 216 | 224802_at | Nedd4 family interacting protein 2 | NDFIP2 | AA019338 | 0.02 | 1.6960912 |
| 217 | 224827_at | Dendritic cell-derived ubiquitin-like protein | DC-UbP | AK022894 | 0.01 | 1.5073498 |
| 218 | 224902_at | pyruvate dehydrogenase phosphatase regulatory subunit | PDPR | BE644918 | 0.02 | 1.6357323 |
| 219 | 224950_at | prostaglandin F2 receptor negative regulator | PTGFRN | BF476250 | 0.03 | 1.9777663 |
| 220 | 225071_at | chromosome 6 open reading frame 68 | C6orf68 | BG168247 | 0.03 | 1.6909997 |
| 221 | 225272_at | spermidine/spermine N1-acetyltransferase 2 | SAT2 | AA128261 | 0.01 | 1.6911607 |
| 222 | 225331_at | chromosome 3 open reading frame 6 | C3orf6 | BF941088 | 0.02 | 2.126105 |
| 223 | 225342_at | adenylate kinase 3-like 1 | AK3L1 | AK026966 | 0.01 | 7.1160383 |
| 224 | 225366_at | phosphoglucomutase 2 | PGM2 | AI652855 | 0.03 | 1.527827 |
| 225 | 225375_at | chromosome 17 open reading frame 32 | C17orf32 | AW975808 | 0.02 | 1.8780395 |
| 226 | 225380_at | hypothetical protein BC007901 | LOC91461 | BF528878 | 0.02 | 2.6365216 |
| 227 | 225383_at | zinc finger protein 275 | ZNF275 | BF793625 | 0.01 | 1.639558 |
| 228 | 225547_at | HBII-276 host gene | HBII-276HG | BG169443 | 0.01 | 1.6269366 |
| 229 | 225550_at | | | AV700816 | 0.01 | 1.6167612 |
| 230 | 225571_at | leukemia inhibitory factor receptor | LIFR | AA701657 | 0.03 | 3.5799398 |
| 231 | 225575_at | leukemia inhibitory factor receptor | LIFR | AI680541 | 0.01 | 3.1433964 |
| 232 | 225578_at | similar to RIKEN cDNA 2410129H14 | LOC440145 | AI885466 | 0.01 | 1.8692675 |
| 233 | 225750_at | ERO1-like (*S. cerevisiae*) | ERO1L | BE966748 | 0.02 | 2.0413787 |
| 234 | 225842_at | Pleckstrin homology-like domain, family A, member 1 | PHLDA1 | AK026181 | 0.02 | 2.5619717 |
| 235 | 225847_at | arylacetamide deacetylase-like 1 | AADACL1 | AB037784 | 0.02 | 1.6796919 |
| 236 | 226060_at | RFT1 homolog (*S. cerevisiae*) | RFT1 | BF475369 | 0.01 | 1.5211235 |
| 237 | 226112_at | sarcoglycan, beta (43 kDa dystrophin-associated glycoprotein) | SGCB | AI678717 | 0.01 | 1.5416645 |
| 238 | 226278_at | hypothetical protein DKFZp313A2432 | DKFZp313A2432 | AI150224 | 0.02 | 1.6910942 |
| 239 | 226335_at | ribosomal protein S6 kinase, 90 kDa, polypeptide 3 | RPS6KA3 | BG498334 | 0.01 | 1.8176109 |
| 240 | 226352_at | Junction-mediating and regulatory protein | JMY | BF447037 | 0.01 | 2.4128768 |
| 241 | 226488_at | RCC1 domain containing 1 | RCCD1 | AW007826 | 0.03 | 1.777583 |
| 242 | 226568_at | hypothetical protein LOC284611 | LOC284611 | AI478747 | 0.01 | 2.1426997 |
| 243 | 226609_at | discoidin, CUB and LCCL domain containing 1 | DCBLD1 | N22751 | 0.01 | 2.0089936 |
| 244 | 226702_at | hypothetical protein LOC129607 | LOC129607 | AI742057 | 0.01 | 2.5539525 |
| 245 | 226722_at | family with sequence similarity 20, member C | FAM20C | BE874872 | 0.01 | 2.2937167 |
| 246 | 226726_at | O-acyltransferase (membrane bound) domain containing 2 | OACT2 | W63676 | 0.01 | 2.8518102 |
| 247 | 226778_at | Chromosome 8 open reading frame 42 | C8orf42 | AI632224 | 0.02 | 1.9250498 |
| 248 | 226780_s_at | hypothetical protein HSPC268 | HSPC268 | BF540829 | 0.01 | 1.8384567 |
| 249 | 226781_at | hypothetical protein HSPC268 | HSPC268 | BF540829 | 0.01 | 1.7917764 |
| 250 | 226784_at | TWIST neighbor | TWISTNB | AA121481 | 0.01 | 1.750498 |
| 251 | 226832_at | Hypothetical LOC389188 | LOC389188 | BF978778 | 0.01 | 1.538109 |
| 252 | 226863_at | Full-length cDNA clone CS0DJ001YJ05 of T cells (Jurkat cell line) Cot 10-normalized of *Homo sapiens* (human) | | AI674565 | 0.01 | 3.1555974 |
| 253 | 226926_at | dermokine | ZD52F10 | AA706316 | 0.02 | 3.190141 |
| 254 | 227141_at | chromosome 1 open reading frame 171 | C1orf171 | AW205739 | 0.02 | 1.6063374 |
| 255 | 227148_at | pleckstrin homology domain containing, family H (with MyTH4 domain) member 2 | PLEKHH2 | AI913749 | 0.03 | 2.1525955 |
| 256 | 227172_at | hypothetical protein BC000282 | LOC89894 | BC000282 | 0.02 | 1.9858925 |
| 257 | 227249_at | | | AI857685 | 0.01 | 1.9229563 |
| 258 | 227314_at | Integrin, alpha 2 (CD49B, alpha 2 subunit of VLA-2 receptor) | ITGA2 | N95414 | 0.03 | 3.3500278 |
| 259 | 227393_at | transmembrane protein 16J | TMEM16J | AW084755 | 0.01 | 1.6880668 |
| 260 | 227466_at | hypothetical protein LOC285550 | LOC285550 | BF108695 | 0.02 | 1.5282669 |
| 261 | 227771_at | leukemia inhibitory factor receptor | LIFR | AW592684 | 0.01 | 2.7902896 |
| 262 | 227808_at | DnaJ (Hsp40) homolog, subfamily C, member 15 | DNAJC15 | AI091398 | 0.03 | 1.8649827 |
| 263 | 227998_at | S100 calcium binding protein A16 | S100A16 | AA045184 | 0.02 | 2.2575665 |
| 264 | 228152_s_at | hypothetical protein FLJ31033 | FLJ31033 | AK023743 | 0.02 | 2.2769616 |
| 265 | 228275_at | CDNA FLJ32438 fis, clone SKMUS2001402 | | AI200555 | 0.02 | 1.813842 |
| 266 | 228531_at | sterile alpha motif domain containing 9 | SAMD9 | AA741307 | 0.02 | 2.303081 |
| 267 | 228562_at | Zinc finger and BTB domain containing 10 | ZBTB10 | N29918 | 0.01 | 2.046323 |
| 268 | 228600_x_at | hypothetical protein MGC72075 | MGC72075 | BE220330 | 0.02 | 1.6221175 |
| 269 | 228640_at | BH-protocadherin (brain-heart) | PCDH7 | BE644809 | 0.03 | 3.3346767 |
| 270 | 228713_s_at | dehydrogenase/reductase (SDR family) member 10 | DHRS10 | AI742586 | 0.02 | 1.9451209 |
| 271 | 228854_at | Transcribed locus | | AI492388 | 0.03 | 4.4617124 |
| 272 | 228972_at | | | AI028602 | 0.02 | 1.6522069 |
| 273 | 229573_at | Transcribed locus | | AI659456 | 0.01 | 1.5438964 |
| 274 | 229582_at | chromosome 18 open reading frame 37 | C18orf37 | AI758919 | 0.01 | 1.6219943 |

TABLE 2-continued

| NO | Probe Set ID | Gene Name | Gene Symbol | Genbank Accession # | T-test p-value | Fold change (abs) |
|---|---|---|---|---|---|---|
| 275 | 229997_at | vang-like 1 (van gogh, *Drosophila*) | VANGL1 | AA789332 | 0.02 | 1.6355668 |
| 276 | 230206_at | Dedicator of cytokinesis 5 | DOCK5 | AI692645 | 0.01 | 1.7685658 |
| 277 | 230329_s_at | nudix (nucleoside diphosphate linked moiety X)-type motif 6 | NUDT6 | AI580268 | 0.02 | 1.5125636 |
| 278 | 230655_at | *Homo sapiens*, clone IMAGE: 5418468, mRNA | | AW025928 | 0.01 | 2.44095 |
| 279 | 230972_at | ankyrin repeat domain 9 | ANKRD9 | AW194999 | 0.01 | 1.875526 |
| 280 | 231828_at | *Homo sapiens*, clone IMAGE: 5218355, mRNA | | AL117474 | 0.02 | 2.1623232 |
| 281 | 231832_at | UDP-N-acetyl-alpha-D-galactosamine:polypeptide N-acetylgalactosaminyltransferase 4 (GalNAc-T4) | GALNT4 | AI890347 | 0.01 | 1.8446548 |
| 282 | 234675_x_at | CDNA: FLJ23566 fis, clone LNG10880 | | AK027219 | 0.01 | 2.4514613 |
| 283 | 234725_s_at | sema domain, immunoglobulin domain (Ig), transmembrane domain (TM) and short cytoplasmic domain, (semaphorin) 4B | SEMA4B | AK026133 | 0.01 | 1.9406958 |
| 284 | 235015_at | Zinc finger, DHHC-type containing 9 | ZDHHC9 | AL529434 | 0.01 | 2.4835925 |
| 285 | 235019_at | carboxypeptidase M | CPM | BE878495 | 0.02 | 3.833762 |
| 286 | 235096_at | Leo1, Paf1/RNA polymerase II complex component, homolog (*S. cerevisiae*) | LEO1 | AA074729 | 0.01 | 1.5779704 |
| 287 | 235648_at | zinc finger protein 567 | ZNF567 | AA742659 | 0.02 | 1.6336213 |
| 288 | 235911_at | hypothetical gene supported by BC034933; BC068085 | LOC440995 | AI885815 | 0.01 | 4.651685 |
| 289 | 238063_at | hypothetical protein FLJ32028 | FLJ32028 | AA806283 | 0.01 | 2.002421 |
| 290 | 238523_at | chromosome 16 open reading frame 44 | C16orf44 | BF941204 | 0.03 | 1.5099897 |
| 291 | 238701_x_at | FLJ45803 protein | FLJ45803 | BE176566 | 0.01 | 2.3077648 |
| 292 | 238778_at | membrane protein, palmitoylated 7 (MAGUK p55 subfamily member 7) | MPP7 | AI244661 | 0.02 | 3.0538154 |
| 293 | 239896_at | Similar to RAB guanine nucleotide exchange factor (GEF) 1 | LOC402671 | AW190479 | 0.01 | 1.6268736 |
| 294 | 241994_at | Xanthine dehydrogenase | XDH | BG260086 | 0.02 | 3.2672102 |
| 295 | 241996_at | | | AI669591 | 0.01 | 1.7369617 |
| 296 | 244495_x_at | chromosome 18 open reading frame 45 | C18orf45 | AL521157 | 0.01 | 1.8056976 |
| 297 | 36553_at | acetylserotonin O-methyltransferase-like | ASMTL | AA669799 | 0.02 | 1.6164968 |
| 298 | 36829_at | period homolog 1 (*Drosophila*) | PER1 | AF022991 | 0.01 | 1.9640467 |
| 299 | 55081_at | MICAL-like 1 | MICAL-L1 | W46406 | 0.02 | 1.5616423 |
| 300 | 60474_at | chromosome 20 open reading frame 42 | C20orf42 | AA469071 | 0.01 | 3.1548133 |

TABLE 3

| NO. | Probe Set ID | Gene Name | Gene Symbol | Genbank Accession # | T-test p-value | Fold change (abs) |
|---|---|---|---|---|---|---|
| 001 | 117_at | heat shock 70 kDa protein 6 (HSP70B$$) | HSPAB | X51757 | 0.03 | 1.7216957 |
| 002 | 1552486_s_at | lactamase, beta | LACTB | NM_171846 | 0.02 | 1.5217854 |
| 003 | 1553530_a_at | integrin, beta 1 (fibronectin receptor, beta polypeptide, antigen CD29 includes MDF2, MSK12) | ITGB1 | NM_033669 | 0.01 | 2.0436814 |
| 004 | 1553694_a_at | phosphoinositide-3-kinase, class 2, alpha polypeptide | PIK3C2A | NM_002645 | 0.03 | 1.6315013 |
| 005 | 1553715_s_at | hypothetical protein MGC15416 | MGC15416 | NM_032371 | 0.02 | 1.5123988 |
| 006 | 1554747_a_at | septin 2 | 02-Sep | BC033559 | 0.01 | 1.560747 |
| 007 | 1555326_a_at | ADAM metallopeptidase domain 9 (meltrin gamma) | ADAM9 | AF495383 | 0.03 | 2.140922 |
| 008 | 1555060_a_at | KIAA1702 protein | KIAA1702 | AK027074 | 0.01 | 1.5686767 |
| 009 | 1557987_at | PI-3-kinase-related kinase SMG-1 - like locus | LOC641298 | BC042832 | 0.01 | 2.2149343 |
| 010 | 1558678_s_at | metastasis associated lung adenocarcinoma transcript 1 (non-coding RNA) | MALAT1 | BE708432 | 0.01 | 2.2265985 |
| 011 | 1560622_at | TPA regulated locus | TPARL | AK000203 | 0.03 | 1.5656745 |
| 012 | 1564053_a_at | YTH domain family, member 3 | YTHDF3 | AK093081 | 0.02 | 1.8976958 |
| 013 | 1569106_s_at | hypothetical protein FLJ10707 | FLJ10707 | BI087313 | 0.02 | 1.5838199 |
| 014 | 200604_s_at | protein kinase, cAMP-dependent, regulatory, type I, alpha (tissue specific extinguisher 1) | PRKAR1A | M18468 | 0.02 | 1.5480618 |
| 015 | 200864_s_at | RAB11A, member RAS oncogene family | RAB11A | NM_004663 | 0.01 | 1.5156919 |
| 016 | 200927_s_at | RAB14, member RAS oncogene family | RAB14 | AA919115 | 0.01 | 1.607915 |
| 017 | 201152_s_at | muscleblind-like (*Drosophila*) | MBNL1 | N31913 | 0.01 | 1.5028459 |
| 018 | 201194_at | selenoprotein W, 1 | SEPW1 | NM_003009 | 0.01 | 1.8139104 |
| 019 | 201362_at | influenza virus NS1A binding protein | IVNS1ABP | AF205218 | 0.02 | 1.5876002 |
| 020 | 201363_s_at | influenza virus NS1A binding protein | IVNS1ABP | AB020657 | 0.01 | 1.6949687 |
| 021 | 201376_s_at | heterogeneous nuclear ribonucleoprotein F | HNRPF | AI591354 | 0.01 | 1.5007194 |
| 022 | 201386_s_at | DEAH (Asp-Glu-Ala-His) box polypeptide 15 | DHX15 | AF279891 | 0.01 | 1.7872009 |
| 023 | 201399_s_at | translocation associated membrane protein 1 | TRAM1 | NM_014294 | 0.01 | 1.6199075 |
| 024 | 201505_at | laminin, beta 1 | LAMB1 | NM_002291 | 0.01 | 2.091507 |
| 025 | 201548_s_at | Jumonji, AT rich interactive domain 1B (RBP2-like) | JARID1B | W02593 | 0.02 | 1.5838325 |
| 026 | 201549_x_at | Jumonji, AT rich interactive domain 1B (RBP2-like) | JARID1B | NM_006618 | 0.02 | 1.6096623 |
| 027 | 201559_s_at | chloride intracellular channel 4 | CLIC4 | AF109196 | 0.02 | 2.2302318 |
| 028 | 201578_at | podocalyxin-like | PODXL | NM_005397 | 0.01 | 2.138917 |
| 029 | 201617_x_at | caldesmon 1 | CALD1 | NM_004342 | 0.01 | 2.0084002 |
| 030 | 201619_at | peroxiredoxin 3 | PRDX3 | NM_006793 | 0.01 | 1.5513384 |
| 031 | 201646_at | scavenger receptor class B, member 2 | SCARB2 | AA885297 | 0.02 | 1.6010221 |
| 032 | 201647_s_at | scavenger receptor class B, member 2 | SCARB2 | NM_005506 | 0.03 | 1.5906466 |
| 033 | 201661_s_at | acyl-CoA synthetase long-chain family member 3 | ACSL3 | NM_004457 | 0.01 | 1.6001148 |

TABLE 3-continued

| NO. | Probe Set ID | Gene Name | Gene Symbol | Genbank Accession # | T-test p-value | Fold change (abs) |
|---|---|---|---|---|---|---|
| 034 | 201678_s_at | DC12 protein | DC12 | NM_020187 | 0.03 | 1.5643462 |
| 035 | 201787_at | fibulin 1 | FBLN1 | NM_001996 | 0.03 | 1.910708 |
| 036 | 201798_s_at | fer-1-like 3, myoferlin (*C. elegans*) | FER1L3 | NM_013451 | 0.02 | 1.6354269 |
| 037 | 201918_at | Solute carrier family 25, member 36 | SLC25A36 | AI927944 | 0.03 | 1.6411883 |
| 038 | 201942_s_at | carboxypeptidase D | CPD | D85390 | 0.02 | 1.6134206 |
| 039 | 202007_at | nidogen 1 | NID1 | BF940043 | 0.03 | 1.784865 |
| 040 | 202143_s_at | COP9 constitutive photomorphogenic homolog subunit 8 (*Arabidopsis*) | COPS8 | NM_006710 | 0.02 | 1.5126611 |
| 041 | 202374_s_at | RAB3 GTPase activating protein subunit 2 (non-catalytic) | RAB3GAP2 | NM_012414 | 0.02 | 1.5766535 |
| 042 | 202429_s_at | protein phosphatase 3 (formerly 2B), catalytic subunit, alpha isoform (calcineurin A alpha) | PPP3CA | AL353950 | 0.01 | 1.7161785 |
| 043 | 202444_s_at | SPFH domain family, member 1 | SPFH1 | NM_006459 | 0.01 | 1.8896967 |
| 044 | 202457_s_at | protein phosphatase 3 (formerly 2B), catalytic subunit, alpha isoform (calcineurin A alpha) | PPP3CA | AA911231 | 0.01 | 1.552117 |
| 045 | 202536_at | chromatin modifying protein 2B | CHMP2B | AK002165 | 0.01 | 1.5160311 |
| 046 | 202593_s_at | membrane interacting protein of RGS16 | MIR16 | NM_016641 | 0.02 | 1.5102472 |
| 047 | 202627_s_at | serpin peptidase inhibitor, clade E (nexin, plasminogen activator inhibitor type 1), member 1 | SERPINE1 | AL574210 | 0.02 | 3.9358664 |
| 048 | 202628_s_at | serpin peptidase inhibitor, clade E (nexin, plasminogen activator inhibitor type 1), member 1 | SERPINE1 | NM_000602 | 0.02 | 3.6850758 |
| 049 | 202770_s_at | cyclin G2 | CCNG2 | NM_004354 | 0.03 | 1.5435082 |
| 050 | 202923_s_at | glutamate-cysteine ligase, catalytic subunit | GCLC | NM_001498 | 0.02 | 2.9063768 |
| 051 | 202946_s_at | BTB (POZ) domain containing 3 | BTBD3 | NM_014962 | 0.01 | 1.6240557 |
| 052 | 202955_s_at | ADP-ribosylation factor guanine nucleotide-exchange factor 1 (brefeldin A-inhibited) | ARFGEF1 | AF084520 | 0.02 | 1.5484247 |
| 053 | 203066_at | B cell RAG associated protein | GALNAC4S-6ST | NM_014863 | 0.03 | 1.5839539 |
| 054 | 203085_s_at | transforming growth factor, beta 1 (Camurati-Engelmann disease) | TGFB1 | BC000125 | 0.03 | 2.1608279 |
| 055 | 203293_s_at | lectin, mannose-binding, 1 | LMAN1 | NM_005570 | 0.02 | 1.9789635 |
| 056 | 203294_s_at | lectin, mannose-binding, 1 | LMAN1 | U09716 | 0.02 | 2.082541 |
| 057 | 203404_at | armadillo repeat containing. X-linked 2 | ARMCX2 | NM_014782 | 0.02 | 2.0663633 |
| 058 | 203748_x_at | RNA binding motif, single stranded interacting protein 1 | RBMS1 | NM_016839 | 0.01 | 1.6428717 |
| 059 | 204053_x_at | phosphatase and tensin homolog (mutated in multiple advanced cancers 1) | PTEN | U96180 | 0.02 | 1.7072555 |
| 060 | 204066_s_at | centaurin, gamma 2 | CENTG2 | NM_014914 | 0.03 | 1.6650882 |
| 061 | 204605_at | cell growth regulator with ring finger domain 1 | CGRRF1 | NM_006568 | 0.02 | 1.5059351 |
| 062 | 204790_at | SMAD, mothers against DPP homolog 7 (*Drosophila*) | SMAD7 | NM_005904 | 0.03 | 1.7849346 |
| 063 | 205180_s_at | ADAM metallopeptidase domain 8 | ADAM8 | NM_001109 | 0.03 | 1.8976016 |
| 064 | 205436_s_at | H2A histone family, member X | H2AFX | NM_002105 | 0.01 | 1.542324 |
| 065 | 205527_s_at | gem (nuclear organelle) associated protein 4 | GEMIN4 | NM_015487 | 0.01 | 1.5615736 |
| 066 | 206042_x_at | small nuclear ribonucleoprotein polypeptide N SNRPN upstream reading frame | SNRPN | NM_022804 | 0.02 | 1.6762362 |
| 067 | 206113_s_at | RAB5A, member RAS oncogene family | RAB5A | NM_004162 | 0.02 | 1.7590842 |
| 068 | 206116_s_at | tropomyosin 1 (alpha) | TPM1 | NM_000366 | 0.01 | 2.168161 |
| 069 | 206245_s_at | influenza virus NS1A binding protein | IVNS1ABP | NM_006469 | 0.01 | 1.5090567 |
| 070 | 207266_x_at | RNA binding motif, single stranded interacting protein 1 | RBMS1 | NM_016837 | 0.01 | 1.6106415 |
| 071 | 207431_s_at | degenerative spermatocyte homolog 1, lipid desaturase (*Drosophila*) | DEGS1 | NM_003676 | 0.01 | 1.542273 |
| 072 | 207821_s_at | PTK2 protein tyrosine kinase 2 | PTK2 | NM_005607 | 0.01 | 1.6032615 |
| 073 | 208097_s_at | thioredoxin domain containing | TXNDC | NM_030755 | 0.02 | 1.7288516 |
| 074 | 208643_s_at | X-ray repair complementing defective repair in Chinese hamster cells 5 (double-strand-break rejoining; Ku autoantigen, 80 kDa) | XRCC5 | J04977 | 0.02 | 1.5489099 |
| 075 | 208859_s_at | alpha thalassemia/mental retardation syndrome X-linked (RAD54 homolog, *S. cerevisiae*) | ATRX | AI650257 | 0.02 | 1.6250781 |
| 076 | 209131_s_at | synaptosomal-associated protein, 23 kDa | SNAP23 | U55936 | 0.01 | 1.8967965 |
| 077 | 209209_s_at | pleckstrin homology domain containing, family C (with FERM domain) member 1 | PLEKHC1 | AW469573 | 0.02 | 2.2543647 |
| 078 | 209409_at | growth factor receptor-bound protein 10 | GRB10 | D86962 | 0.02 | 1.7913702 |
| 079 | 209647_s_at | suppressor of cytokine signaling 5 | SOCS5 | AW664421 | 0.01 | 1.5314134 |
| 080 | 209868_s_at | RNA binding motif, single stranded interacting protein 1 | RBMS1 | D28482 | 0.01 | 1.757919 |
| 081 | 210154_at | malic enzyme 2, NAD(+)-dependent, mitochondrial | ME2 | M55905 | 0.03 | 1.658911 |
| 082 | 210337_s_at | ATP citrate lyase | ACLY | U18197 | 0.03 | 1.6132175 |
| 083 | 210809_s_at | periostin, osteoblast specific factor | POSTN | D13665 | 0.03 | 1.9660459 |
| 084 | 211202_s_at | Jumonji, AT rich interactive domain 1B (RBP2-like) | JARID1B | AF087481 | 0.03 | 1.6053953 |
| 085 | 211559_s_at | cyclin G2 | CCNG2 | L49506 | 0.03 | 2.0475583 |
| 086 | 211651_s_at | laminin, beta 1 | LAMB1 | M20206 | 0.01 | 2.44758 |
| 087 | 211864_s_at | fer-1-like 3, myoferlin (*C. elegans*) | FER1L3 | AF207990 | 0.02 | 1.9618642 |
| 088 | 211981_at | collagen, type IV, alpha 1 | COL4A1 | NM_001845 | 0.03 | 2.0343637 |
| 089 | 211985_s_at | calmodulin 1 (phosphorylase kinase, delta) | CALM1 | AI653786 | 0.03 | 1.5034102 |
| 090 | 211992_at | WNK lysine deficient protein kinase 1 | WNK1 | AI445745 | 0.02 | 1.5539628 |
| 091 | 212298_at | neuropilin 1 | NRP1 | BE620457 | 0.02 | 1.7827071 |
| 092 | 212660_at | PHD finger protein 15 | PHF15 | AI735639 | 0.02 | 1.7572457 |
| 093 | 212720_at | poly(A) polymerase alpha | PAPOLA | AI670847 | 0.02 | 1.6408824 |
| 094 | 212907_at | Solute carrier family 30 (zinc transporter), member 1 | SLC30A1 | AI972416 | 0.01 | 1.739024 |
| 095 | 213012_at | neural precursor cell expressed, developmentally down-regulated 4 | NEDD4 | D42055 | 0.02 | 1.6585234 |
| 096 | 213061_s_at | N-terminal asparagine amidase | NTAN1 | AA643304 | 0.02 | 1.5069518 |
| 097 | 213901_x_at | RNA binding motif protein 9 | RBM9 | AW149379 | 0.02 | 1.5630468 |
| 098 | 214196_s_at | tripeptidyl peptidase I | TPP1 | AA602532 | 0.02 | 1.8428509 |

TABLE 3-continued

| NO. | Probe Set ID | Gene Name | Gene Symbol | Genbank Accession # | T-test p-value | Fold change (abs) |
|---|---|---|---|---|---|---|
| 099 | 214544_s_at | synaptosomal-associated protein, 23 kDa | SNAP23 | NM_003825 | 0.02 | 1.8551272 |
| 100 | 214581_x_at | tumor necrosis factor receptor superfamily, member 21 | TNFRSF21 | BE568134 | 0.01 | 1.9035177 |
| 101 | 214701_s_at | fibronectin 1 | FN1 | AJ276395 | 0.01 | 2.180369 |
| 124 | 222540_s_at | hepatitis B virus x associated protein | HBXAP | BG286920 | 0.01 | 1.678279 |
| 125 | 222693_at | fibronectin type III domain containing 3B | FNDC3B | BF444916 | 0.02 | 1.5484349 |
| 126 | 223010_s_at | OCIA domain containing 1 | OCIAD1 | AA454649 | 0.01 | 1.638761 |
| 127 | 223110_at | KIAA1429 | KIAA1429 | BC003701 | 0.02 | 1.555597 |
| 128 | 223276_at | putative small membrane protein NID67 | NID67 | AF313413 | 0.02 | 1.8129323 |
| 129 | 223577_x_at | PRO1073 protein | PRO1073 | AA827878 | 0.02 | 2.037919 |
| 130 | 223940_x_at | metastasis associated lung adenocarcinoma transcript 1 (non-coding RNA) | MALAT1 | AF132202 | 0.01 | 2.7140348 |
| 131 | 224567_x_at | metastasis associated lung adenocarcinoma transcript 1 (non-coding RNA) | MALAT1 | BG534952 | 0.02 | 2.436764 |
| 132 | 224726_at | mindbomb homolog 1 (*Drosophila*) | MIB1 | W80418 | 0.03 | 1.5452155 |
| 133 | 224819_at | transcription elongation factor A (SII)-like 8 | TCEAL8 | AI743979 | 0.01 | 1.5945034 |
| 134 | 224859_at | CD276 antigen | CD276 | AL360136 | 0.03 | 1.5041374 |
| 135 | 225021_at | zinc finger protein 532 | ZNF532 | AA861416 | 0.02 | 1.6210703 |
| 136 | 225032_at | fibronectin type III domain containing 3B | FNDC3B | AI141784 | 0.01 | 1.5388452 |
| 137 | 225168_at | FERM domain containing 4A | FRMD4A | T78406 | 0.01 | 1.8072422 |
| 138 | 225239_at | | | AI355441 | 0.02 | 2.2125103 |
| 139 | 225285_at | branched chain aminotransferase 1, cytosolic | BCAT1 | AK025615 | 0.02 | 2.027126 |
| 140 | 225424_at | glycerol-3-phosphate acyltransferase, mitochondrial | GPAM | AB046780 | 0.02 | 1.740033 |
| 141 | 225567_at | Hypothetical LOC388114 | LOC388114 | BE207755 | 0.01 | 1.888815 |
| 142 | 225609_at | glutathione reductase | GSR | AI888037 | 0.02 | 2.144665 |
| 143 | 225974_at | transmembrane protein 64 | TMEM64 | BF732480 | 0.02 | 1.5707608 |
| 144 | 226280_at | BCL2/adenovirus E1B 19 kDa interacting protein 2 | BNIP2 | AA133277 | 0.02 | 1.5715192 |
| 145 | 226558_at | Full-length cDNA clone CS0DI062YC15 of Placenta Cot 25-normalized of *Homo sapiens* (human) | | BE856637 | 0.02 | 1.6961281 |
| 146 | 226675_s_at | metastasis associated, lung adenocarcinoma transcript 1 (non-coding RNA) | MALAT1 | W80468 | 0.01 | 2.2176015 |
| 147 | 226850_at | sulfatase modifying factor 1 | SUMF1 | AA683501 | 0.02 | 1.582926 |
| 148 | 227062_at | trophoblast-derived noncoding RNA | TncRNA | AU155361 | 0.01 | 3.1964853 |
| 149 | 227072_at | rotatin | RTTN | BG167480 | 0.02 | 1.6342819 |
| 150 | 227080_at | zinc finger protein 697 | ZNF697 | AW003092 | 0.01 | 2.047982 |
| 151 | 227257_s_at | chromosome 10 open reading frame 46 | C10orf46 | AW973842 | 0.02 | 1.8308182 |
| 152 | 227456_s_at | chromosome 6 open reading frame 136 | C6orf136 | BF224092 | 0.02 | 1.5313978 |
| 153 | 229586_at | chromodomain helicase DNA binding protein 9 | CHD9 | AW300405 | 0.01 | 1.6146306 |
| 154 | 229606_at | Protein phosphatase 3 (formerly 2B), catalytic subunit, alpha isoform (calcineurin A alpha) | PPP3CA | AI827550 | 0.02 | 1.5514666 |
| 155 | 229982_at | hypothetical protein FLJ21924 | FLJ21924 | AW195525 | 0.03 | 1.5703845 |
| 156 | 231735_s_at | PRO1073 protein | PRO1073 | NM_014086 | 0.02 | 2.0209107 |
| 157 | 231823_s_at | KIAA1295 | KIAA1295 | BG054798 | 0.03 | 1.527874 |
| 158 | 234989_at | trophoblast-derived noncoding RNA | TncRNA | AV699657 | 0.02 | 2.0119648 |
| 159 | 235138_at | Pumilio homolog 2 (*Drosophila*) | PUM2 | AA565051 | 0.01 | 1.7716993 |
| 160 | 235879_at | Muscleblind-like (*Drosophila*) | MBNL1 | AI697540 | 0.01 | 2.2558458 |
| 161 | 236841_at | CXYorf1-related protein | FLJ25222 | BE464132 | 0.01 | 1.7994804 |
| 162 | 238549_at | core-binding factor, runt domain, alpha subunit 2; translocated to, 2 | CBFA2T2 | AI420611 | 0.01 | 1.928193 |
| 163 | 239742_at | Tubby like protein 4 | TULP4 | H15278 | 0.03 | 1.5802637 |
| 164 | 242121_at | | | AW973232 | 0.03 | 1.7029374 |
| 165 | 243768_at | SUMO1/sentrin specific peptidase 6 | SENP6 | AA026388 | 0.01 | 2.2681193 |
| 166 | 244804_at | Sequestosome 1 | SQSTM1 | AW293441 | 0.01 | 1.5338039 |

In Tables 1, 2 and 3, gene name denotes a name of a gene, gene symbol denotes a symbol representing a gene, and Genbank Accession # denotes a number accessing Genbank which is a database that the public can access. T-test p value is obtained by statistically analyzing the degree of difference between an average expression level in a patient with lung cancer recurrence and an average expression level in a patient without lung cancer recurrence after lung cancer tissue removal operation.

Here, an expression level was calculated by Affymetrix GeneChip Operating Software (GCOS) Version 1.3 after a hybridization analysis using a microarray on which a probe is immobilized. Fold change (abs) indicates a ratio between an average expression level in a patient with lung cancer recurrence and an average expression level in a patient without lung cancer recurrence after lung cancer tissue removal operation in a hybridization analysis using a microarray on which a probe is immobilized.

As shown in Tables 1, 2 and 3, expression values of at least one marker gene selected from the group consisting of marker genes of Genbank Accession No. shown in Tables 1, 2 and 3 showed statistically meaningful differences such that both T-test p values of the patient with lung cancer recurrence and the patient without lung cancer recurrence were less than 0.05. Therefore, at least one marker gene selected from the group consisting of marker genes of Genbank Accession No. shown in Tables 1, 2 and 3 can be used as a marker gene that can predict whether lung cancer is recurred afterwards with respect to the patients with a lung cancer removal operation. In addition, at least one marker gene selected from the group consisting of marker genes of Genbank Accession No. shown in Tables 1, 2 and 3 had showed that all the ratios of an expression average of the patients with lung cancer recurrence to an expression average of the patients without lung cancer recurrence was at least 1.5:1. Accordingly, it was confirmed that the expression of the marker gene was significantly increased in the patients with lung cancer recurrence.

DETAILED DESCRIPTION OF THE INVENTION

Hereinafter, the present invention will be described more specifically with reference to the following Examples. The following Examples are for illustrative purposes and are not intended to limit the scope of the invention.

EXAMPLE

Example 1

Selection of Marker Gene Related to Lung Cancer Recurrence

Primary lung cancer tissue having a tumor size of less than 3 cm and without lymph node metastase (that is, $N_0M_0T_1$ stage) was collected. Total RNA was then immediately isolated from the collected lung cancer tissue. All the collected tumor tissue was lightly dyed with hematoxylin in order to improve visualization prior to RNA extraction. Each finely cut sample comprised at least 90% of tumor cells.

To avoid a necrotic region, one or two pieces of tumor tissue having a size of 5 mm×5 mm from the edge of tumor mass was immediately stored at −80□.

The finely cut tumor tissue was added to 1 ml of a Trizol reagent (Life Technologies, Rockville, Md.), and immediately homogenized by vortexing. Total RNA was isolated according to Trizol reagent protocol. The quality of the isolated total RNA was analyzed by electrophoresis using 1% agarose gel comprising 0.6 M formamide and ethidium bromide. An amount of total RNA was analyzed using a Nanodrop spectrometer (Nanodrop Technologies, Rockland, Del.).

The quality and amount of the isolated total RNA were confirmed to be excellent, and a reverse transcription reaction was performed using the RNA as a template and oligo dT as a primer to obtain cDNA. The obtained cDNA was used as a template that synthesizes cRNA through an in vitro transcription reaction. At this time, cRNA synthesized by adding UTP modified with biotin to a reaction solution was labeled with biotin. Next, the synthesized biotin-labeled cRNA was reacted with a hydroxyl radical to be fragmentized with a size of 50-200 bp. 10 µg of the fragmentized cRNA sample was injected onto an Affymetrix GeneChip array (human 133 plus ver 2) and hybridized at 45□ for 16 hours. The hybridization mixture was then removed and the microarrays were washed, stained with phycoerythrin-labeled Streptavidin, washed, incubated with biotinylated anti-streptavidin, and then restained with phycoerythrin-labeled Streptavidin to amplify the signals. Arrays were scanned using the GeneChip Scanner 3000 7G scanner (Affymetrix), controlled by Affymetrix GeneChip Operating System (GCOS) software. The Affymetrix Microarray Suite version 5 (MAS5) algorithm were utilized to analyze the hybridization intensity data from the microarrays and calculate a set of matrixes that describe probe set performance.

The obtained data was analyzed using an ArrayAssist™ (Stratagene, Inc., San Diego, USA) program. Data preprocessing was performed using a GCRMA (log 2 transformation) method that is a normalization method of multi-microarray level, in which fluorescence intensity values with respect to total microarrays used in analysis were substituted with log 2, and a fluorescence intensity average with respect to the total microarrays was adjusted taking into consideration of a GC amount of a nucleic acid sequence. Comparison between groups was performed under conditions of unpaired t-test, permutation=100, corrected p-value, Number of False Discovery Rate (NO/FDR). Data filtering was performed by selecting only data that satisfied an expression level (recurrence and non-recurrence, group average)>5 and fold change≧1.5. A count for each probeset_id was defined as the number of probe sets that showed a gene expression difference that satisfies the filtering standard in ADC, SQC, or in the recurrence group and non-recurrence group regardless of cell types.

As a result of analysis, the number of markers selected as positive expression with respect to adenocarcinoma (ADC) and squamous cell carcinoma (SQC) are shown in Table 4 below.

TABLE 4

|  | total lung cancer tissue | adenocarcinoma | squamous cell carcinoma |
|---|---|---|---|
| number of probe | 166 | 300 | 166 |

Data related to expression of each gene that was obtained by the measurement of fluorescence intensity was obtained. To confirm correlation between the collected data related to expression of gene and lung cancer recurrence, patients with a lung cancer removal operation were monitored for five years to confirm lung cancer recurrence or non-recurrence. In the case of patients with lung cancer recurrence within one year after a lung cancer removal operation, they were grouped into a lung cancer recurrence group. In the case of patients without lung cancer recurrence even after three years after a lung cancer removal operation, they were grouped into a non-recurrence group. Data with respect to the obtained recurrence group and non-recurrence group among patients with a lung cancer removal operation was obtained.

Next, correlation between an expression pattern of each gene which was analyzed during the lung cancer removal operation, and the recurrence and non-recurrence groups that were subsequently obtained by monitoring the patients with a lung cancer removal operation was analyzed. The results are shown in Tables 1, 2 and 3.

Table 1 represents the results in which the gene expression pattern of the lung cancer cell after lung cancer tissue removal operation is analyzed through hybridization with a probe on a microarray, and a marker gene is selected, the marker gene being determined to have a difference in an expression level between a patient with lung cancer recurrence within one year and a patient without lung cancer recurrence even after three years. The total number of patients was 60. Among them, the number of patients with lung cancer recurrence within one year after lung cancer tissue removal operation was 19, and the number of patients without lung cancer recurrent even after three years was 41.

Table 2 represents the results in which the gene expression pattern of the lung cancer cell which was classified into adenocarcinoma after lung cancer tissue removal operation is analyzed through hybridization with a probe on a microarray, and a marker gene is selected, the marker gene being determined to have a difference in an expression level between a patient with lung cancer recurrence within one year and a patient without lung cancer recurrence even after three years. A total number of adenocarcinoma patients was 23. Among them, the number of patients with lung cancer recurrence within one year after lung cancer tissue removal operation was 8, and the number of patients without lung cancer recurrent even after three years was 15.

Table 3 represents the results in which the gene expression pattern of the lung cancer cell which was classified into squamous cell carcinoma after lung cancer tissue removal operation is analyzed through hybridization with a probe on a microarray, and a marker gene is selected, the marker gene being determined to have a difference in an expression level between a patient with lung cancer recurrence within one year and a patient without lung cancer recurrence even after three years. The total number of squamous cell carcinoma patients was 37. Among them, the number of patients with lung cancer recurrence within one year after lung cancer tissue removal operation was 11, and the number of patients without lung cancer recurrent even after three years was 26.

As shown in Tables 1, 2 and 3, expression values of at least one marker gene selected from the group consisting of marker genes of Genbank Accession No. shown in Tables 1, 2 and 3 showed statistically meaningful differences such that both T-test p values of the patient with lung cancer recurrence and the patient without lung cancer recurrence were less than 0.05. Therefore, at least one marker gene selected from the group consisting of marker genes of Genbank Accession No. shown in Tables 1, 2 and 3 can be used as a marker gene that can predict whether lung cancer is likely to recur with respect to the patients that have had a lung cancer removal operation. In addition, at least one marker gene selected from the group consisting of marker genes of Genbank Accession No. shown in Tables 1, 2 and 3 showed that all the ratios of an expression average of the patients with lung cancer recurrence to an expression average of the patients without lung cancer recurrence were at least 1.5:1. Accordingly, it was confirmed that the expression of the marker gene was significantly increased in the patients with lung cancer recurrence.

The relationships between lung cancer recurrence in patients after lung cancer removal operation and conditions of the patients such as age, sex, smoking, cell type, pstage, and tumor size were analyzed, and the results are shown in Tables 5, 6 and 7.

TABLE 5

| variation | statistical analysis method | result |
|---|---|---|
| sex | chi-square test | no difference: p value = 0.552 |
| age | 2-sample t-test | no difference: p value = 0.559 |
| smoking | chi-square test | no difference: p value = 0.813 |
| cell type | chi-square test | no difference: p value = 0.682 |
| pstage | Fisher's exact test | no difference: p value = 0.305 |
| tumor size | 2-sample t-test | difference: p value = 0.039 |
| metastasis | — | no metastasis |

Table 5 shows results of analyzing 60 patients without classifying them according to cell types of lung cancer. Among 60 patients, the number of patients with lung cancer recurrence was 19, and the number of patients without lung cancer recurrence was 41. As shown in Table 5, the clinical indexes from the all patients looked no statistically meaningful difference in the recurrence group and the non-recurrence group. That is, the analyzed result can be regarded as a gene list that represents statistically meaningful difference in expression only with respect to the recurrence.

TABLE 6

| variation | statistical analysis method | result |
|---|---|---|
| sex | Fisher's exact test | no difference: p value = 1.000 |
| age | 2-sample t-test | no difference: p value = 0.618 |
| smoking | chi-square test | no difference: p value = 0.6570 |
| cell type | — | adenocarcinoma (ADC) |
| pstage | Fisher's exact test | no difference: p value = 0.085 |
| tumor size | 2-sample t-test | no difference: p value = 0.051 |
| metastasis | — | no metastasis |

Table 6 shows results of analyzing 23 patients having adenocarcinoma when they are classified according to cell types of lung cancer. Among 23 patients, the number of patients with lung cancer recurrence was 8, and the number of patients without lung cancer recurrence was 15. As shown in Table 6, clinical information except the recurrence and tumor size which may induce confounding in other analysis may not have any statistically meaningful difference in the recurrence group and the non-recurrence group. That is, the analyzed result can be regarded as a gene list that represents statistically meaningful difference in expression only with respect to the recurrence.

TABLE 7

| variation | statistical analysis method | result |
|---|---|---|
| sex | — | man |
| age | 2-sample t-test | no difference: p value = 0.328 |
| smoking | chi-square test | no difference: p value = 1.000 |
| cell type | — | squamous cell carcinoma (SQC) |
| pstage | Fisher's exact test | no difference: p value = 1.000 |
| tumor size | 2-sample t-test | no difference: p value = 0.417 |
| metastasis | — | no metastasis |

Table 7 shows results of analyzing 37 patients having squamous cell carcinoma when they are classified according to cell types of lung cancer. Among 23 patients, the number of patients with lung cancer recurrence was 11, and the number of patients without lung cancer recurrence was 26. As shown in Table 7, clinical information except the recurrence and tumor size which may induce confounding in other analysis may not have any statistically meaningful difference in the recurrence group and the non-recurrence group. That is, the analyzed result can be regarded as a gene list that represents statistically meaningful difference in expression only with respect to the recurrence.

Example 2

Prediction of Risk of Lung Cancer Recurrence Using Statistical Model

Based on the expression level of marker genes collected from the patients with lung cancer recurrence and non-recurrence which were obtained in Example 1, it was confirmed whether a risk of lung cancer recurrence could be predicted using a statistical analysis model.

In the analysis, a portion of each of data obtained with respect to total lung cancer tissue, adenocarcinoma and squamous cell carcinoma was used as a learning set to establish a basis on the prediction accuracy of the statistical model, the other portion of the data was used to identify whether the establish prediction accuracy is actually accurate using the leaning set Data of learning sets and test sets with respect to the total lung cancer tissue, adenocarcinoma and squamous cell carcinoma are shown in Tables 8, 9 and 10.

TABLE 8

| total lung cancer tissue | non-recurrence | recurrence | total |
|---|---|---|---|
| learning set | 28 | 15 | 43 |
| test set | 13 | 4 | 17 |
| total | 41 | 19 | 60 |

TABLE 9

| adenocarcinoma | non-recurrence | recurrence | total |
|---|---|---|---|
| learning set | 9 | 6 | 15 |
| test set | 6 | 2 | 8 |
| total | 16 | 8 | 23 |

TABLE 10

| squamous cell carcinoma | non-recurrence | recurrence | total |
|---|---|---|---|
| learning set | 17 | 7 | 24 |
| test set | 9 | 4 | 13 |
| total | 26 | 11 | 37 |

Results of predicting the test set with respect to the lung cancer tissue, adenocarcinoma and squamous cell carcinoma using a QDA prediction model are shown in Tables 11, 12 and 13 below. As shown in Tables 11, 12 and 13, the overall accuracy was at least 76.4%.

TABLE 11

Predicted results of the total lung cancer tissue using a QDA prediction model

| | | predicted class | | |
|---|---|---|---|---|
| | classification | non-recurrence | recurrence | total |
| true class | non-recurrence | 10 | 1 | 11 |
| | recurrence | 3 | 3 | 6 |
| | overall accuracy | | | 76.4% |

The overall accuracy in Table 11 is a percentage of predicted class which corresponds to true class per total sample. That is, the overall accuracy is $(17-4) \times 100/17 = 76.4\%$. The total is calculated in the same manner described above.

TABLE 12

Predicted results of adenocarcinoma tissue using a QDA prediction model

| | | predicted class | | |
|---|---|---|---|---|
| | classification | non-recurrence | recurrence | total |
| true class | non-recurrence | 6 | 0 | 6 |
| | recurrence | 0 | 2 | 2 |
| | overall accuracy | | | 100% |

TABLE 13

Predicted results of squamous cell carcinoma tissue using a QDA prediction model

| | | predicted class | | |
|---|---|---|---|---|
| | classification | non-recurrence | recurrence | total |
| true class | non-recurrence | 9 | 2 | 11 |
| | recurrence | 0 | 2 | 2 |
| | overall accuracy | | | 84.6% |

Results of predicting the test set with respect to the lung cancer tissue, adenocarcinoma and squamous cell carcinoma using a Linear Discrimination Analysis (LDA) prediction model are shown in Tables 14, 15 and 16 below. As shown in Tables 14, 15 and 16, the overall accuracy was at least 76.4%.

TABLE 14

Predicted results of the total lung cancer tissue using a LDA prediction model

| | | predicted class | | |
|---|---|---|---|---|
| | classification | non-recurrence | recurrence | total |
| true class | non-recurrence | 10 | 1 | 11 |
| | recurrence | 3 | 3 | 6 |
| | overall accuracy | | | 76.4% |

TABLE 15

Predicted results of adenocarcinoma tissue using a LDA prediction model

| | | predicted class | | |
|---|---|---|---|---|
| | classification | non-recurrence | recurrence | total |
| true class | non-recurrence | 6 | 0 | 6 |
| | recurrence | 0 | 2 | 2 |
| | overall accuracy | | | 100% |

TABLE 16

Predicted results of squamous cell carcinoma tissue using a LDA prediction model

| | | predicted class | | |
|---|---|---|---|---|
| | classification | non-recurrence | recurrence | total |
| true class | non-recurrence | 9 | 1 | 10 |
| | recurrence | 0 | 3 | 3 |
| | overall accuracy | | | 92.3% |

Results of predicting the test set with respect to the lung cancer tissue, adenocarcinoma and squamous cell carcinoma using a Neural network prediction model are shown in Tables 17, 18 and 19 below. As shown in Tables 17, 18 and 19, the overall accuracy was at least 59.46%.

TABLE 17

Predicted results of the total lung cancer tissue using a Neural network prediction model

| | | predicted class | | |
|---|---|---|---|---|
| | classification | non-recurrence | recurrence | total |
| true class | non-recurrence | 40 | 1 | 41 |
| | recurrence | 18 | 1 | 19 |
| | overall accuracy | | | 68.33% |

TABLE 18

Predicted results of adenocarcinoma tissue using a Neural network prediction model

| | | predicted class | | |
|---|---|---|---|---|
| | classification | non-recurrence | recurrence | total |
| true class | non-recurrence | 14 | 1 | 15 |
| | recurrence | 1 | 7 | 8 |
| | overall accuracy | | | 91.3% |

TABLE 19

Predicted results of squamous cell carcinoma tissue using a Neural network prediction model

| | | predicted class | | |
|---|---|---|---|---|
| | classification | non-recurrence | recurrence | total |
| true class | non-recurrence | 20 | 6 | 26 |
| | recurrence | 9 | 2 | 11 |
| | overall accuracy | | | 59.46% |

Results of predicting the test set with respect to the lung cancer tissue, adenocarcinoma and squamous cell carcinoma using a Decision tree prediction model are shown in Tables 20, 21 and 22 below. As shown in Tables 20, 21 and 22, the overall accuracy was at least 61.67%.

TABLE 20

Predicted results of the total lung cancer tissue using a Decision tree prediction model

| | | predicted class | | |
|---|---|---|---|---|
| | classification | non-recurrence | recurrence | total |
| true class | non-recurrence | 35 | 6 | 41 |
| | recurrence | 17 | 2 | 19 |
| | overall accuracy | | | 61.67% |

TABLE 21

Predicted results of adenocarcinoma tissue using a Decision tree prediction model

| | | predicted class | | |
|---|---|---|---|---|
| | classification | non-recurrence | recurrence | total |
| true class | non-recurrence | 15 | 0 | 15 |
| | recurrence | 8 | 0 | 8 |
| | overall accuracy | | | 65.22% |

TABLE 22

Predicted results of squamous cell carcinoma tissue using a Decision tree prediction model

| | | predicted class | | |
|---|---|---|---|---|
| | classification | non-recurrence | recurrence | total |
| true class | non-recurrence | 25 | 1 | 26 |
| | recurrence | 2 | 9 | 11 |
| | overall accuracy | | | 91.89% |

Results of predicting the test set with respect to the lung cancer tissue, adenocarcinoma and squamous cell carcinoma using a Support vector machine prediction model are shown in Tables 23, 24 and 25 below. As shown in Tables 23, 24 and 25, the overall accuracy was at least 65%.

TABLE 23

Predicted results of the total lung cancer tissue using a Support vector machine prediction model

| | | predicted class | | |
|---|---|---|---|---|
| | classification | non-recurrence | recurrence | total |
| true class | non-recurrence | 37 | 4 | 41 |
| | recurrence | 17 | 2 | 19 |
| | overall accuracy | | | 65% |

TABLE 24

Predicted results of adenocarcinoma tissue using a Support vector machine prediction model

| | | predicted class | | |
|---|---|---|---|---|
| | classification | non-recurrence | recurrence | total |
| true class | non-recurrence | 15 | 0 | 15 |
| | recurrence | 1 | 7 | 8 |
| | overall accuracy | | | 95.65% |

TABLE 25

Predicted results of squamous cell carcinoma tissue using a Support vector machine prediction model

| | | predicted class | | |
|---|---|---|---|---|
| | classification | non-recurrence | recurrence | total |
| true class | non-recurrence | 24 | 2 | 26 |
| | recurrence | 1 | 10 | 11 |
| | overall accuracy | | | 91.89% |

Results of predicting the test set with respect to the lung cancer tissue, adenocarcinoma and squamous cell carcinoma using a Naive Bayes prediction model are shown in Tables 26, 27 and 28 below. As shown in Tables 26, 27 and 28, the overall accuracy was at least 58.33%.

TABLE 26

Predicted results of the total lung cancer tissue using a Naive Bayes prediction model

| | | predicted class | | |
|---|---|---|---|---|
| classification | | non-recurrence | recurrence | total |
| true class | non-recurrence | 26 | 15 | 41 |
| | recurrence | 10 | 9 | 19 |
| | overall accuracy | | | 58.33% |

TABLE 27

Predicted results of adenocarcinoma tissue using a Naive Bayes prediction model

| | | predicted class | | |
|---|---|---|---|---|
| classification | | non-recurrence | recurrence | total |
| true class | non-recurrence | 15 | 0 | 15 |
| | recurrence | 1 | 7 | 8 |
| | overall accuracy | | | 95.65% |

TABLE 28

Predicted results of squamous cell carcinoma tissue using a Naive Bayes prediction model

| | | predicted class | | |
|---|---|---|---|---|
| classification | | non-recurrence | recurrence | total |
| true class | non-recurrence | 24 | 2 | 26 |
| | recurrence | 1 | 10 | 11 |
| | overall accuracy | | | 91.89% |

The prediction models utilized in Examples of the present invention could have been easily understood by one of ordinary skill in the art (SAS Language: Reference, Version 6, First Edition by the SAS Institute.).

According to the method of predicting risk of lung cancer recurrence in a lung cancer patient or after a patient has lung cancer treatment according to the present invention, the risk of lung cancer recurrence in a lung cancer patient after a lung cancer removal operation can be predicted with high accuracy.

According to the method of preparing a report on the risk of lung cancer recurrence in a lung cancer patient or after a patient has lung cancer treatment according to the present invention, the report can be prepared to include results predicting the risk of lung cancer recurrence in a lung cancer patient after a lung cancer removal operation with high accuracy.

The report on the risk of lung cancer recurrence in a lung cancer patient or after the patient has lung cancer treatment according to the present invention includes highly accurate results predicting the risk of lung cancer recurrence in a lung cancer patient after a lung cancer removal operation.

According to the composition, kit and microarray for diagnosing the risk of lung cancer recurrence in a lung cancer patient or after a patient has lung cancer treatment according to the present invention, diagnosis efficiency of risk of lung cancer recurrence of a lung cancer patient after a lung cancer treatment can be increased.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of predicting risk of lung cancer recurrence in a lung cancer patient or after a patient has lung cancer treatment, the method comprising:

obtaining a lung cancer tissue sample from a lung cancer patient;

measuring an expression level in the lung cancer tissue sample of each target nucleic acid in a set of target nucleic acids consisting of target nucleic acids in Table 1;

determining whether the expression levels of the set of target nucleic acids in the lung cancer tissue sample correspond to expression levels of the set of target nucleic acids in a group of patients with lung cancer recurrence within one year after a lung cancer removal operation ("recurrence group") or to expression levels of the set of target nucleic acids in a group of patients without lung cancer recurrence within three years after a lung cancer removal operation ("non-recurrence group"); and predicting the risk of lung cancer recurrence in the patient is high when the expression levels of the set of target nucleic acids in the lung cancer tissue sample correspond to the expression levels of the recurrence group, or predicting the risk of lung cancer recurrence in the patient is low when the expression levels of the set of target nucleic acids in the lung cancer tissue sample correspond to the expression levels of the nonrecurrence group, wherein Table 1 is shown below

| No. | Probe Set ID | Gene Name | Gene Symbol |
|---|---|---|---|
| 001 | 1552486_s_at | lactamase, beta | LACTB |
| 002 | 1553105_s_at | desmoglein 2 | DSG2 |
| 003 | 1553530_a_at | integrin, beta 1 (fibronectin receptor, beta polypeptide, antigen CD29 includes MDF2 MSK12) | ITGB1 |
| 004 | 1553678_a_at | integrin, beta 1 (fibronectin receptor, beta polypeptide, antigen CD29 includes MDF2, MSK12) | ITGB1 |
| 005 | 1554067_at | hypothetical protein FLJ32549 | FLJ32549 |
| 006 | 1554761_a_at | hypothetical protein FLJ20397 | FLJ20397 |
| 007 | 1555326_a_at | ADAM metallopeptidase domain 9 (meltrin gamma) | ADAM9 |
| 008 | 1555564_a_at | I factor (complement) | IF |
| 009 | 1555705_a_at | chemokine-like factor superfamily 3 | CKLFSF3 |
| 010 | 1557987_at | PI-3-kinase-related kinase SMG-1-like locus | LOC641298 |
| 011 | 1558678_s_at | metastasis associated lung adenocarcinoma transcript 1 (non-coding RNA) | MALAT1 |
| 012 | 160020_at | matrix metallopeptidase 14 (membrane-inserted) | MMP14 |
| 013 | 200604_s_at | protein kinase, cAMP-dependent, regulatory, type I, alpha (tissue specific extinguisher 1) | PRKAR1A |
| 014 | 200615_s_at | adaptor-related protein complex 2, beta 1 subunit | AP2B1 |
| 015 | 200864_s_at | RAB11A, member RAS oncogene family | RAB11A |

| | | | |
|---|---|---|---|
| 016 | 200922_at | KDEL (Lys-Asp-Glu-Leu) endoplasmic reticulum protein retention receptor 1 | KDELR1 |
| 017 | 201020_at | tyrosine 3-monooxygenase/ tryptophan 5-monooxygenase activation protein, eta polypeptide | YWHAH |
| 018 | 201179_s_at | guanine nucleotide binding protein (G protein), alpha inhibiting activity polypeptide 3 | GNAI3 |
| 019 | 201309_x_at | chromosome 5 open reading frame 13 | C5orf13 |
| 020 | 201363_s_at | influenza virus NS1A binding protein | IVNS1ABP |
| 021 | 201505_at | laminin, beta 1 | LAMB1 |
| 022 | 201506_at | transforming growth factor, beta-induced, 68 kDa | TGFBI |
| 023 | 201548_s_at | Jumonji, AT rich interactive domain 1B (RBP2-like) | JARID1B |
| 024 | 201559_s_at | chloride intracellular channel 4 | CLIC4 |
| 025 | 201564_s_at | fascin homolog 1, actin-bundling protein (Strongylocentrotus purpuratus) | FSCN1 |
| 026 | 201578_at | podocalyxin-like | PODXL |
| 027 | 201617_x_at | caldesmon 1 | CALD1 |
| 028 | 201646_at | scavenger receptor class B, member 2 | SCARB2 |
| 029 | 201647_s_at | scavenger receptor class B, member 2 | SCARB2 |
| 030 | 201695_s_at | nucleoside phosphorylase | NP |
| 031 | 201722_s_at | UDP-N-acetyl-alpha-D-galactosamine:polypeptide N-acetylgalactosaminyltransferase 1 (GalNAc-T1) | GALNT1 |
| 032 | 201918_at | Solute carrier family 25, member 36 | SLC25A36 |
| 033 | 201942_s_at | carboxypeptidase D | CPD |
| 034 | 202267_at | laminin, gamma 2 | LAMC2 |
| 035 | 202543_s_at | glia maturation factor, beta | GMFB |
| 036 | 202604_x_at | ADAM metallopeptidase domain 10 | ADAM10 |
| 037 | 202627_s_at | serpin peptidase inhibitor, clade E (nexin, plasminogen activator inhibitor type 1), member 1 | SERPINE1 |
| 038 | 202628_s_at | serpin peptidase inhibitor, clade E (nexin, plasminogen activator inhibitor type 1), member 1 | SERPINE1 |
| 039 | 202817_s_at | synovial sarcoma transloca-tion, chromosome 18 | SS18 |
| 040 | 202859_x_at | interleukin 8 | IL8 |
| 041 | 202936_s_at | SRY (sex determining region Y)-box 9 (campomelic dysplasia, autosomal sex-reversal) | SOX9 |
| 042 | 202949_s_at | four and a half LIM domains 2 | FHL2 |
| 043 | 202998_s_at | lysyl oxidase-like 2 | LOXL2 |
| 044 | 203066_at | B cell RAG associated protein | GALNAC4S-6ST |
| 045 | 203072_at | myosin IE | MYO1E |
| 046 | 203293_s_at | lectin, mannose-binding, 1 | LMAN1 |
| 047 | 203294_s_at | lectin, mannose-binding, 1 | LMAN1 |
| 048 | 203414_at | monocyte to macrophage differentiation-associated | MMD |
| 049 | 203553_s_at | mitogen-activated protein kinase kinase kinase kinase 5 | MAP4K5 |
| 050 | 203924_at | glutathione S-transferase A1 | GSTA1 |
| 051 | 203988_s_at | fucosyltransferase 8 (alpha (1,6) fucosyltransferase) | FUT8 |
| 052 | 204426_at | transmembrane emp24 domain trafficking protein 2 | TMED2 |
| 053 | 204470_at | chemokine (C-X-C motif) ligand 1 (melanoma growth stimulating activity, alpha) | CXCL1 |
| 054 | 204702_s_at | nuclear factor (erythroid-derived 2)-like 3 | NFE2L3 |
| 055 | 204790_at | SMAD, mothers against DPP homolog 7 (Drosophila) | SMAD7 |
| 056 | 204944_at | protein tyrosine phosphatase, receptor type, G | PTPRG |
| 057 | 204989_s_at | integrin, beta 4 | ITGB4 |
| 058 | 205120_s_at | sarcoglycan, beta (43 kDa dystrophin-associated glycoprotein) | SGCB |
| 059 | 205180_s_at | ADAM metallopeptidase domain 8 | ADAM8 |
| 060 | 205479_s_at | plasminogen activator, urokinase | PLAU |
| 061 | 206025_s_at | tumor necrosis factor, alpha-induced protein 6 | TNFAIP6 |
| 062 | 206113_s_at | RAB5A, member RAS oncogene family | RAB5A |
| 063 | 206116_s_at | tropomyosin 1 (alpha) | TPM1 |
| 064 | 206245_s_at | Influenza virus NS1A binding protein | IVNS1ABP |
| 065 | 206323_x_at | oligophrenin 1 | OPHN1 |
| 066 | 208510_s_at | peroxisome proliferative activated receptor, gamma | PPARG |
| 067 | 208613_s_at | filamin B, beta (actin binding protein 278) | FLNB |
| 068 | 208637_x_at | actinin, alpha 1 | ACTN1 |
| 069 | 208653_s_at | CD164 antigen, sialomucin | CD164 |
| 070 | 208853_s_at | calnexin | CANX |
| 071 | 209131_s_at | synaptosomal-associated protein, 23 kDa | SNAP23 |
| 072 | 209209_s_at | pleckstrin homology domain containing, family C (with FERM domain) member 1 | PLEKHC1 |
| 073 | 209314_s_at | HBS1-like (S. cerevisiae) | HBS1L |
| 074 | 209316_s_at | HBS1-like (S. cerevisiae) | HBS1L |
| 075 | 209409_at | growth factor receptor-bound protein 10 | GRB10 |
| 076 | 209410_s_at | growth factor receptor-bound protein 10 | GRB10 |
| 077 | 209537_at | exostoses (multiple)-like 2 | EXTL2 |
| 078 | 210845_s_at | plasminogen activator, urokinase receptor | PLAUR |
| 079 | 210892_s_at | general transcription factor II, i | GTF2I |
| 080 | 210933_s_at | fascin homolog 1, actin-bundling protein (Strongylocentrotus purpuratus) | FSCN1 |
| 081 | 210987_x_at | tropomyosin 1 (alpha) | TPM1 |
| 082 | 211299_s_at | flotillin 2 | FLOT2 |
| 083 | 211506_s_at | interleukin 8 | IL8 |
| 084 | 211559_s_at | cyclin G2 | CCNG2 |
| 085 | 211599_x_at | met proto-oncogene (hepatocyte growth factor receptor) | MET |
| 086 | 211651_s_at | laminin, beta 1 | LAMB1 |
| 087 | 211668_s_at | plasminogen activator, urokinase | PLAU |
| 088 | 211864_s_at | fer-1-like 3, myoferlin (C. elegans) | FER1L3 |
| 089 | 211924_s_at | plasminogen activator, urokinase receptor | PLAUR |
| 090 | 211981_at | collagen, type IV, alpha 1 | COL4A1 |
| 091 | 212012_at | peroxidasin homolog (Drosophila) | PXDN |
| 092 | 212660_at | PHD finger protein 15 | PHF15 |
| 093 | 212720_at | poly(A) polymerase alpha | PAPOLA |
| 094 | 212907_at | Solute carrier family 30 (zinc transporter), member 1 | SLC30A1 |
| 095 | 213288_at | O-acyltransferase (membrane bound) domain containing 2 | OACT2 |
| 096 | 213457_at | malignant fibrous histio-cytoma amplified sequence 1 | MFHAS1 |
| 097 | 213624_at | sphingomyelin phosphodiesterase, acid-like 3A | SMPDL3A |

| No. | | | |
|---|---|---|---|
| 098 | 213742_at | splicing factor, arginine/serine-rich 11 | SFRS11 |
| 099 | 214121_x_at | PDZ and LIM domain 7 (enigma) | PDLIM7 |
| 100 | 214196_s_at | tripeptidyl peptidase I | TPP1 |
| 101 | 214544_s_at | synaptosomal-associated protein, 23 kDa | SNAP23 |
| 102 | 214581_x_at | tumor necrosis factor receptor superfamily, member 21 | TNFRSF21 |
| 103 | 214701_s_at | fibronectin 1 | FN1 |
| 104 | 214866_at | plasminogen activator, urokinase receptor | PLAUR |
| 105 | 214895_s_at | ADAM metallopeptidase domain 10 | ADAM10 |
| 106 | 215501_s_at | dual specificity phosphatase 10 | DUSP10 |
| 107 | 216035_x_at | transcription factor 7-like 2 (T-cell specific, HMG-box) | TCF7L2 |
| 108 | 216511_s_at | transcription factor 7-like 2 (T-cell specific, HMG-box) | TCF7L2 |
| 109 | 216915_s_at | protein tyrosine phosphatase, non-receptor type 12 | PTPN12 |
| 110 | 216971_s_at | plectin 1, intermediate filament binding protein 500 kDa | PLEC1 |
| 111 | 217188_s_at | chromosome 14 open reading frame 1 | C14orf1 |
| 112 | 217448_s_at | chromosome 14 open reading frame 92 similar to Epidermal Langerhans cell protein LCP1 | C14orf92 LOC285412 |
| 113 | 217492_s_at | phosphatase and tensin homolog (mutated in multiple advanced cancers 1) | PTEN |
| 114 | 218000_s_at | pleckstrin homology-like domain, family A, member 1 | PHLDA1 |
| 115 | 218077_s_at | zinc finger, DHHC-type containing 3 | ZDHHC3 |
| 116 | 218078_s_at | zinc finger, DHHC-type containing 3 | ZDHHC3 |
| 117 | 218435_at | DnaJ (Hsp40) homolog, subfamily C, member 15 | DNAJC15 |
| 118 | 218644_at | pleckstrin 2 | PLEK2 |
| 119 | 218748_s_at | SEC10-like 1 (S. cerevisiae) | SEC10L1 |
| 120 | 218815_s_at | transmembrane protein 51 | TMEM51 |
| 121 | 218826_at | solute carrier family 35, member F2 | SLC35F2 |
| 122 | 218854_at | squamous cell carcinoma antigen recognized by T cells 2 | SART2 |
| 123 | 218856_at | tumor necrosis factor receptor superfamily, member 21 | TNFRSF21 |
| 124 | 218885_s_at | UDP-N-acetyl-alpha-D-galactosamine:polypeptide N-acetylgalactosaminyl-transferase 12 (GalNAc-T12) | GALNT12 |
| 125 | 219410_at | transmembrane protein 45A | TMEM45A |
| 126 | 219603_s_at | zinc finger protein 226 | ZNF226 |
| 127 | 220199_s_at | chromosome 1 open reading frame 80 | C1orf80 |
| 128 | 220617_s_at | zinc finger protein 532 | ZNF532 |
| 129 | 221268_s_at | sphingosine-1-phosphate phosphatase 1 | SGPP1 |
| 130 | 221881_s_at | chloride intracellular channel 4 | CLIC4 |
| 131 | 222399_s_at | SM-11044 binding protein | SMBP |
| 132 | 222449_at | tranamembrane, prostate androgen induced RNA | TMEPAI |
| 133 | 222528_s_at | solute carrier family 25, member 37 | SLC25A37 |
| 134 | 222540_s_at | hepatitis B virus x associated protein | HBXAP |
| 135 | 222692_s_at | fibronectin type III domain containing 3B | FNDC3B |
| 136 | 222693_at | fibronectin type III domain containing 3B | FNDC3B |
| 137 | 222773_s_at | UDP-N-acetyl-alpha-D-galactosamine:polypeptide N-acetylgalactosaminyl-transferase 12 (GalNAc-T12) | GALNT12 |
| 138 | 223577_x_at | PRO1073 protein | PRO1073 |
| 139 | 223940_x_at | metastasis associated lung adenocarcinoma transcript 1 (non-coding RNA) | MALAT1 |
| 140 | 224558_s_at | metastasis associated lung adenocarcinoma transcript 1 (non-coding RNA) | MALAT1 |
| 141 | 224674_at | tweety homolog 3 (Drosophila) | TTYH3 |
| 142 | 224733_at | chemokine-like factor superfamily 3 | CKLFSF3 |
| 143 | 224802_at | Nedd4 family interacting protein 2 | NDFIP2 |
| 144 | 225021_at | zinc finger protein 532 | ZNF532 |
| 145 | 225140_at | Kruppel-like factor 3 (basic) | KLF3 |
| 146 | 225168_at | FERM domain containing 4A | FRMD4A |
| 147 | 225424_at | glycerol-3-phosphate acyltransferase, mitochondrial | GPAM |
| 148 | 225503_at | dehydrogenase/reductase (SDR family) X-linked | DHRSX |
| 149 | 225567_at | Hypothetical LOC388114 | LOC388114 |
| 150 | 225609_at | glutathione reductase | GSR |
| 151 | 225842_at | Pleckstrin homology-like domain, family A, member 1 | PHLDA1 |
| 152 | 226084_at | microtubule-associated protein 1B | MAP1B |
| 153 | 226352_at | Junction-mediating and regulatory protein | JMY |
| 154 | 226726_at | O-acyltransferase (membrane bound) domain containing 2 | OACT2 |
| 155 | 226780_s_at | hypothetical protein HSPC268 | HSPC268 |
| 156 | 227257_s_at | chromosome 10 open reading frame 46 | C10orf46 |
| 157 | 227628_at | similar to RIKEN cDNA 2310016C16 | LOC493869 |
| 158 | 227808_at | DnaJ (Hsp40) homolog, subfamily C, member 15 | DNAJC15 |
| 159 | 230206_at | Dedicator of cytokinesis 5 | DOCK5 |
| 160 | 231735_s_at | PRO1073 protein | PRO1073 |
| 161 | 231823_s_at | KIAA1295 | KIAA1295 |
| 162 | 235587_at | hypothetical protein LOC202781 | LOC202781 |
| 163 | 235879_at | Muscleblind-like (Drosophila) | MBNL1 |
| 164 | 238558_at | Muscleblind-like (Drosophila) | MBNL1 |
| 165 | 238563_at | Abl-interactor 1 | ABI1 |
| 166 | 238701_x_at | FLJ45803 protein | FLJ45803 |

| No. | Genbank Accession # | T-test p-value | Fold change (abs) |
|---|---|---|---|
| 001 | NM_171846 | 0.005162234 | 1.522293 |
| 002 | NM_001943 | 0.019467462 | 2.3323212 |
| 003 | NM_033669 | 0.01684671 | 1.7791877 |
| 004 | NM_133376 | 0.012459265 | 1.7374801 |
| 005 | BC036246 | 0.002290308 | 1.5143739 |
| 006 | BC010850 | 0.001210456 | 1.6267678 |
| 007 | AF495383 | 0.012324799 | 2.1980886 |
| 008 | BC020718 | 0.007528743 | 2.5875902 |
| 009 | AY166714 | 0.004961676 | 1.8687251 |
| 010 | BC042832 | 0.010989661 | 1.7944587 |
| 011 | BE708432 | 0.00670648 | 1.6990829 |
| 012 | Z48481 | 0.005463324 | 1.5193439 |
| 013 | M18468 | 0.017312625 | 1.5803499 |
| 014 | AL567295 | 0.007407852 | 1.6839108 |
| 015 | NM_004663 | 0.000163535 | 1.5653288 |
| 016 | NM_006801 | 0.004791257 | 1.638207 |
| 017 | NM_003405 | 0.009279575 | 1.5148095 |
| 018 | J03005 | 0.014834337 | 1.5069977 |
| 019 | U36189 | 0.011555359 | 2.1326842 |
| 020 | AB020657 | 0.00119686 | 1.5838884 |
| 021 | NM_002291 | 0.000568398 | 1.8073287 |
| 022 | NM_000358 | 0.008768089 | 1.9059453 |
| 023 | W02593 | 0.010550437 | 1.5276276 |
| 024 | AF109196 | 0.002245945 | 2.1570368 |
| 025 | NM_003088 | 0.007795681 | 2.1724482 |
| 026 | NM_005397 | 0.00303411 | 1.8943018 |

-continued

| | | | |
|---|---|---|---|
| 027 | NM_004342 | 0.01926877 | 1.8294148 |
| 028 | AA885297 | 0.006063032 | 1.6768507 |
| 029 | NM_005506 | 0.015885489 | 1.6841809 |
| 030 | NM_000270 | 0.018524641 | 1.6833633 |
| 031 | AV692127 | 0.009770202 | 1.5369248 |
| 032 | AI927944 | 0.00259865 | 1.6228764 |
| 033 | D85390 | 0.017363481 | 1.7431495 |
| 034 | NM_005562 | 0.004330024 | 2.8191426 |
| 035 | BC005359 | 0.008048828 | 1.5254242 |
| 036 | NM_001110 | 0.002003783 | 1.767903 |
| 037 | AL574210 | 0.00091248 | 3.0523725 |
| 038 | NM_000602 | 0.00504642 | 2.6835847 |
| 039 | NM_005637 | 0.005462693 | 1.5148987 |
| 040 | NM_000584 | 0.014948112 | 2.1844351 |
| 041 | NM_000346 | 0.019816045 | 2.2876046 |
| 042 | NM_001450 | 0.006776552 | 2.2249734 |
| 043 | NM_002318 | 0.006687925 | 2.0231075 |
| 044 | NM_014863 | 0.00419499 | 1.5032523 |
| 045 | NM_004998 | 0.000449373 | 1.5877136 |
| 046 | NM_005570 | 0.002661762 | 1.9762497 |
| 047 | U09716 | 0.000473367 | 1.9764429 |
| 048 | NM_012329 | 0.001585437 | 1.6128623 |
| 049 | NM_006575 | 0.010453912 | 1.5251595 |
| 050 | NM_000846 | 0.004046575 | 4.2017674 |
| 051 | NM_004480 | 0.01139016 | 1.6090198 |
| 052 | NM_006815 | 0.015985437 | 1.6165011 |
| 053 | NM_001511 | 0.001788037 | 3.218731 |
| 054 | NM_004289 | 0.015985157 | 1.7023398 |
| 055 | NM_005904 | 0.013379821 | 1.7179344 |
| 056 | NM_002841 | 0.004963213 | 1.769544 |
| 057 | BF305661 | 0.012746719 | 2.1320713 |
| 058 | U29586 | 0.013908542 | 1.7317705 |
| 059 | NM_001109 | 0.000473816 | 2.054043 |
| 060 | NM_002658 | 0.003415823 | 2.4370956 |
| 061 | AW188198 | 0.013965369 | 2.1515768 |
| 062 | NM_004162 | 0.010821017 | 1.571063 |
| 063 | NM_000366 | 0.000283653 | 2.0841253 |
| 064 | NM_006469 | 0.003607815 | 1.5105128 |
| 065 | NM_002547 | 0.018292218 | 1.5056778 |
| 066 | NM_015869 | 0.002361554 | 1.882336 |
| 067 | AV712733 | 0.001033398 | 1.7958147 |
| 068 | BC003576 | 0.000448714 | 1.631627 |
| 069 | AF263279 | 0.017487219 | 1.5380286 |
| 070 | L18887 | 0.011792572 | 1.5100785 |
| 071 | U55936 | 0.001730693 | 1.8878508 |
| 072 | AW469573 | 0.009551367 | 1.9820172 |
| 073 | AK024258 | 0.00507411 | 1.6641864 |
| 074 | BC001465 | 0.006051209 | 1.6464524 |
| 075 | D86962 | 0.01098607 | 1.7481923 |
| 076 | AF000017 | 0.013879589 | 1.701537 |
| 077 | AF000416 | 0.003979554 | 1.5687809 |
| 078 | U08839 | 0.007479298 | 1.7924315 |
| 079 | BC004472 | 0.003141172 | 1.619537 |
| 080 | BC004908 | 0.00342191 | 1.906748 |
| 081 | M19267 | 0.004614187 | 1.6935222 |
| 082 | BC003683 | 0.015057402 | 1.5387125 |
| 083 | AF043337 | 0.005428782 | 2.867063 |
| 084 | L49506 | 0.010491861 | 1.8367761 |
| 085 | U19348 | 0.019789577 | 1.9247686 |
| 086 | M20206 | 0.000418344 | 1.997547 |
| 087 | K03226 | 0.00240352 | 2.8568754 |
| 088 | AF207990 | 0.011889962 | 1.7860718 |
| 089 | AY029180 | 0.011789334 | 1.8189595 |
| 090 | NM_001845 | 0.007531395 | 1.8490748 |
| 091 | BF342851 | 0.016265145 | 1.8463359 |
| 092 | AI735639 | 0.007391165 | 1.5595657 |
| 093 | AI670847 | 0.016607396 | 1.5904158 |
| 094 | AI972416 | 0.002460855 | 1.63999 |
| 095 | AI761250 | 0.010427832 | 1.6232696 |
| 096 | BF739959 | 0.003050241 | 1.8505166 |
| 097 | AA873600 | 0.005912889 | 1.8562527 |
| 098 | AW241752 | 0.006011819 | 1.9170463 |
| 099 | AA086229 | 5.50514E-05 | 1.5048952 |
| 100 | AA602532 | 0.015398935 | 1.5939685 |
| 101 | NM_003825 | 0.003539713 | 1.8040004 |
| 102 | BE568134 | 0.002274355 | 2.2189345 |
| 103 | AJ276395 | 0.001182322 | 2.071262 |
| 104 | X74039 | 0.003173471 | 1.7340106 |
| 105 | AU135154 | 0.004170008 | 1.9890832 |
| 106 | AK022513 | 0.018290011 | 1.5388945 |
| 107 | AV721430 | 0.000657631 | 1.7091621 |
| 108 | AJ270770 | 0.004103699 | 1.5264177 |
| 109 | S69182 | 0.005493577 | 1.6935816 |
| 110 | Z54367 | 0.01826363 | 1.7186335 |
| 111 | AC007182 | 0.011925477 | 1.6185476 |
| 112 | AL117508 | 0.007782524 | 1.5433311 |
| 113 | AF023139 | 0.007220107 | 1.5624946 |
| 114 | NM_007350 | 0.016502094 | 1.6960312 |
| 115 | BE542551 | 0.01684034 | 1.5417765 |
| 116 | NM_016598 | 0.010970607 | 1.5836283 |
| 117 | NM_013238 | 0.019865552 | 1.7292447 |
| 118 | NM_016445 | 0.000675608 | 2.7071812 |
| 119 | NM_006544 | 0.012352341 | 1.7368068 |
| 120 | NM_018022 | 0.000753902 | 1.6477742 |
| 121 | NM_017515 | 0.009280122 | 1.6340361 |
| 122 | NM_013352 | 0.014419112 | 1.6285655 |
| 123 | NM_016629 | 0.01292243 | 1.617686 |
| 124 | NM_024642 | 0.014052196 | 1.6402073 |
| 125 | NM_018004 | 0.018847797 | 2.0938365 |
| 126 | NM_015919 | 0.005593323 | 1.5408667 |
| 127 | NM_022831 | 0.016323 | 1.5315142 |
| 128 | NM_018181 | 0.001976648 | 1.5441327 |
| 129 | NM_030791 | 0.008873873 | 1.9432548 |
| 130 | AI638420 | 0.004401053 | 1.7742935 |
| 131 | BG104571 | 0.00011337 | 1.5270268 |
| 132 | AL035541 | 0.005303006 | 2.2757804 |
| 133 | BG251467 | 0.014745607 | 1.738053 |
| 134 | BG286920 | 0.005694628 | 1.5068418 |
| 135 | BF444916 | 0.001075083 | 1.5835624 |
| 136 | BF444916 | 0.000622161 | 1.7766397 |
| 137 | AA554045 | 0.003090952 | 1.8790901 |
| 138 | AA827878 | 0.003659447 | 1.6790042 |
| 139 | AF132202 | 0.016841894 | 1.9524238 |
| 140 | AI446756 | 0.012874936 | 1.6367766 |
| 141 | AI934753 | 0.002428954 | 1.6452742 |
| 142 | AL574900 | 0.013543638 | 1.5199631 |
| 143 | AA019338 | 0.013437813 | 1.5261155 |
| 144 | AA861416 | 0.002285053 | 1.6213596 |
| 145 | BF438116 | 0.016804362 | 1.5368354 |
| 146 | T78406 | 0.006987929 | 1.5712297 |
| 147 | AB046780 | 0.000390623 | 1.7006425 |
| 148 | AL547782 | 0.005000754 | 1.770981 |
| 149 | BE207755 | 0.003047524 | 1.6990312 |
| 150 | AI888037 | 0.004693668 | 1.8490914 |
| 151 | AK026181 | 0.014052763 | 1.8735564 |
| 152 | AA554833 | 0.016480966 | 1.9064581 |
| 153 | BF447037 | 0.001219355 | 1.5196482 |
| 154 | W63676 | 0.005363467 | 1.8277074 |
| 155 | BF540829 | 0.001859941 | 1.5185972 |
| 156 | AW973842 | 0.000646104 | 1.6094143 |
| 157 | AL571557 | 0.006222301 | 2.0978951 |
| 158 | AI091398 | 0.01153802 | 1.7936606 |
| 159 | AI692645 | 0.005127667 | 1.6694399 |
| 160 | NM_014086 | 0.004784999 | 1.72546 |
| 161 | BG054798 | 0.002478401 | 1.5713933 |
| 162 | BG400596 | 0.018314553 | 1.5202585 |
| 163 | AI697540 | 0.002645486 | 2.0540323 |
| 164 | AI445833 | 0.004576562 | 1.805269 |
| 165 | AV762916 | 0.012934915 | 1.6069295 |
| 166 | BE176566 | 0.01719282 | 1.5133282. |

2. The method of claim 1, wherein the measuring of an expression level of a target nucleic acid is performed by measuring a level of mRNA or protein encoded by the target nucleic acid.

3. The method of claim 1, wherein expression levels in the lung cancer tissue sample correspond to expression levels of the recurrence group when the expression levels in the lung cancer tissue sample show a statistically meaningful difference from the expression levels in the nonrecurrence group or do not show a statistically meaningful difference from the expression levels in the recurrence group; and expression levels in the lung cancer tissue sample correspond to expression levels of the nonrecurrence group when the expression levels in the lung cancer tissue sample show a statistically meaningful difference from the expression levels in the recurrence group or do not show a statistically meaningful difference from the expression levels in the nonrecurrence group, wherein a statistically meaningful difference is expressed as a p value for the difference of less than 0.05.

4. The method of claim 3, wherein determining statistical significance of a difference between expression levels in the lung cancer tissue sample and the recurrence group or the nonrecurrence group is analyzed using a statistical model selected from the group consisting of Linear Discrimination Analysis (LDA) model, a Quadratic Discrimination Analysis (QDA) prediction model, a Neural Network model, a Decision Tree model, a Support Vector Machine model and a Naive Bayes model.

5. The method of claim 1, wherein the expression level is measured on a microarray.

6. The method of claim 5, wherein the microarray is a nucleic acid microarray.

7. The method of claim 1, wherein the expression level of the target nucleic acid is determined by measuring the amount of an amplification product obtained by nucleic acid amplification that is carried out by a reverse transcriptase-polymerase chain reaction (RT-PCR) using RNA as a template.

8. The method of claim 1, wherein the expression level is measured by detecting protein encoded by the target nucleic acid.

9. The method of claim 8, wherein the detecting of protein is performed by using an antibody specific to the protein.

10. A composition for diagnosing the risk of lung cancer recurrence in a lung cancer patient or after a patient has lung cancer treatment, comprising at least one probe or probe set specific to each target nucleic acid in a set of target nucleic acids consisting of target nucleic acids in Tables 1, wherein Table 1 is shown below

| No. | Probe Set ID | Gene Name | Gene Symbol | Genbank Accession # | T-test p-value | Fold change (abs) |
|---|---|---|---|---|---|---|
| 001 | 1552486_s_at | lactamase, beta | LACTB | NM_171846 | 0.005162234 | 1.522293 |
| 002 | 1553105_s_at | desmoglein 2 | DSG2 | NM_001943 | 0.019467462 | 2.3323212 |
| 003 | 1553530_a_at | integrin, beta 1 (fibronectin receptor, beta polypeptide, antigen CD29 includes MDF2, MSK12) | ITGB1 | NM_033669 | 0.01684671 | 1.7791877 |
| 004 | 1553678_a_at | integrin, beta 1 (fibronectin receptor, beta polypeptide, antigen CD29 includes MDF2, MSK12) | ITGB1 | NM_133376 | 0.012459265 | 1.7374601 |
| 005 | 1554067_at | hypothetical protein FLJ32549 | FLJ32549 | BC036246 | 0.002290308 | 1.5143739 |
| 006 | 1554761_a_at | hypothetical protein FLJ20397 | FLJ20397 | BC010850 | 0.001210456 | 1.6267678 |
| 007 | 1555326_a_at | ADAM metallopeptidase domain 9 (meltrin gamma) | ADAM9 | AF495383 | 0.012324799 | 2.1980886 |
| 008 | 1555564_a_at | I factor (complement) | IF | BC020718 | 0.007528743 | 2.5875902 |
| 009 | 1555705_a_at | chemokine-like factor superfamily 3 | CKLFSF3 | AY166714 | 0.004961676 | 1.8687251 |
| 010 | 1557987_at | PI-3-kinase-related kinase SMG-1 - like locus | LOC641298 | BC042832 | 0.010989661 | 1.7944587 |
| 011 | 1558678_s_at | metastasis associated lung adenocarcinoma transcript 1 (non-coding RNA) | MALAT1 | BE708432 | 0.00670648 | 1.6990829 |
| 012 | 160020_at | matrix metallopeptidase 14 (membrane-inserted) | MMP14 | Z48481 | 0.005463324 | 1.5193439 |
| 013 | 200604_s_at | protein kinase, cAMP-dependent, regulatory, type I, alpha (tissue specific extinguisher 1) | PRKAR1A | M18468 | 0.017312625 | 1.5803499 |
| 014 | 200615_s_at | adaptor-related protein complex 2, beta 1 subunit | AP2B1 | AL567295 | 0.007407852 | 1.6839108 |
| 015 | 200864_s_at | RAB11A, member RAS oncogene family | RAB11A | NM_004663 | 0.000163535 | 1.5653288 |
| 016 | 200922_at | KDEL (Lys-Asp-Glu-Leu) endoplasmic reticulum protein retention receptor 1 | KDELR1 | NM_006801 | 0.004791257 | 1.638207 |
| 017 | 201020_at | tyrosine 3-monooxygenase/tryptophan 5-monooxygenase activation protein, eta polypeptide | YWHAH | NM_003405 | 0.009279575 | 1.5148095 |
| 018 | 201179_s_at | guanine nucleotide binding protein (G protein), alpha inhibiting activity polypeptide 3 | GNAI3 | J03005 | 0.014834337 | 1.5069977 |
| 019 | 201309_x_at | chromosome 5 open reading frame 13 | C5orf13 | U36189 | 0.011555359 | 2.1326842 |
| 020 | 201363_s_at | influenza virus NS1A binding protein | IVNS1ABP | AB020657 | 0.00119686 | 1.5838884 |
| 021 | 201505_at | laminin, beta 1 | LAMB1 | NM_002291 | 0.000568398 | 1.8073287 |
| 022 | 201506_at | transforming growth factor, beta-induced, 68 kDa | TGFBI | NM_000358 | 0.008768089 | 1.9059453 |
| 023 | 201548_s_at | Jumonji, AT rich interactive domain 1B (RBP2-like) | JARID1B | W02593 | 0.010550437 | 1.5276276 |
| 024 | 201559_s_at | chloride intracellular channel 4 | CLIC4 | AF109196 | 0.002245945 | 2.1570368 |
| 025 | 201564_s_at | fascin homolog 1, actin-bundling protein (Strongylocentrotus purpuratus) | FSCN1 | NM_003088 | 0.007795681 | 2.1724482 |
| 026 | 201578_at | podocalyxin-like | PODXL | NM_005397 | 0.00303411 | 1.8943018 |
| 027 | 201617_x_at | caldesmon 1 | CALD1 | NM_004342 | 0.01926877 | 1.8294148 |
| 028 | 201646_at | scavenger receptor class B, member 2 | SCARB2 | AA885297 | 0.006063032 | 1.6768507 |
| 029 | 201647_s_at | scavenger receptor class B, member 2 | SCARB2 | NM_005506 | 0.015885489 | 1.6841809 |
| 030 | 201695_s_at | nucleoside phosphorylase | NP | NM_000270 | 0.018524641 | 1.6833633 |
| 031 | 201722_s_at | UDP-N-acetyl-alpha-D-galactosamine:polypeptide N-acetylgalactosaminyltransferase 1 (GalNAc-T1) | GALNT1 | AV692127 | 0.009770202 | 1.5369248 |

-continued

| No. | Probe Set ID | Gene Name | Gene Symbol | Genbank Accession # | T-test p-value | Fold change (abs) |
|---|---|---|---|---|---|---|
| 032 | 201918_at | Solute carrier family 25, member 36 | SLC25A36 | AI927944 | 0.00259865 | 1.6228764 |
| 033 | 201942_s_at | carboxypeptidase D | CPD | D85390 | 0.017363481 | 1.7431495 |
| 034 | 202267_at | laminin, gamma 2 | LAMC2 | NM_005562 | 0.004330024 | 2.8191426 |
| 035 | 202543_s_at | glia maturation factor, beta | GMFB | BC005359 | 0.008048828 | 1.5254242 |
| 036 | 202604_x_at | ADAM metallopeptidase domain 10 | ADAM10 | NM_001110 | 0.002003783 | 1.767903 |
| 037 | 202627_s_at | serpin peptidase inhibitor, clade E (nexin, plasminogen activator inhibitor type 1), member 1 | SERPINE1 | AL574210 | 0.00091248 | 3.0523725 |
| 038 | 202628_s_at | serpin peptidase inhibitor, clade E (nexin, plasminogen activator inhibitor type 1), member 1 | SERPINE1 | NM_000602 | 0.00504642 | 2.6835847 |
| 039 | 202817_s_at | synovial sarcoma translocation, chromosome 18 | SS18 | NM_005637 | 0.005462693 | 1.5148987 |
| 040 | 202859_x_at | interleukin 8 | IL8 | NM_000584 | 0.014948112 | 2.1844351 |
| 041 | 202936_s_at | SRY (sex determining region Y)-box 9 (campomelic dysplasia, autosomal sex-reversal) | SOX9 | NM_000346 | 0.019816045 | 2.2876046 |
| 042 | 202949_s_at | four and a half LIM domains 2 | FHL2 | NM_001450 | 0.006776552 | 2.2249734 |
| 043 | 202998_s_at | lysyl oxidase-like 2 | LOXL2 | NM_002318 | 0.006687925 | 2.0231075 |
| 044 | 203066_at | B cell RAG associated protein | GALNAC4S-6ST | NM_014863 | 0.00419499 | 1.5032523 |
| 045 | 203072_at | myosin IE | MYO1E | NM_004998 | 0.000449373 | 1.5877136 |
| 046 | 203293_s_at | lectin, mannose-binding, 1 | LMAN1 | NM_005570 | 0.002661762 | 1.9762497 |
| 047 | 203294_s_at | lectin, mannose-binding, 1 | LMAN1 | U09716 | 0.000473367 | 1.9764429 |
| 048 | 203414_at | monocyte to macrophage differentiation-associated | MMD | NM_012329 | 0.001585437 | 1.6128623 |
| 049 | 203553_s_at | mitogen-activated protein kinase kinase kinase kinase 5 | MAP4K5 | NM_006575 | 0.010453912 | 1.5251595 |
| 050 | 203924_at | glutathione S-transferase A1 | GSTA1 | NM_000846 | 0.004046575 | 4.2017674 |
| 051 | 203988_s_at | fucosyltransferase 8 (alpha (1,6) fucosyltransferase) | FUT8 | NM_004480 | 0.01139016 | 1.6090198 |
| 052 | 204426_at | transmembrane emp24 domain trafficking protein 2 | TMED2 | NM_006815 | 0.015985437 | 1.6165011 |
| 053 | 204470_at | chemokine (C-X-C motif) ligand 1 (melanoma growth stimulating activity, alpha) | CXCL1 | NM_001511 | 0.001788037 | 3.218731 |
| 054 | 204702_s_at | nuclear factor (erythroid-derived 2)-like 3 | NFE2L3 | NM_004289 | 0.015985157 | 1.7023398 |
| 055 | 204790_at | SMAD, mothers against DPP homolog 7 (*Drosophila*) | SMAD7 | NM_005904 | 0.013379821 | 1.7179344 |
| 056 | 204944_at | protein tyrosine phosphatase, receptor type, G | PTPRG | NM_002841 | 0.004963213 | 1.769544 |
| 057 | 204989_s_at | integrin, beta 4 | ITGB4 | BF305661 | 0.012746719 | 2.1320713 |
| 058 | 205120_s_at | sarcoglycan, beta (43 kDa dystrophin-associated glycoprotein) | SGCB | U29586 | 0.013908542 | 1.7317705 |
| 059 | 205180_s_at | ADAM metallopeptidase domain 8 | ADAM8 | NM_001109 | 0.000473816 | 2.054043 |
| 060 | 205479_s_at | plasminogen activator, urokinase | PLAU | NM_002658 | 0.003415823 | 2.4370956 |
| 061 | 206025_s_at | tumor necrosis factor, alpha-induced protein 6 | TNFAIP6 | AW188198 | 0.013965369 | 2.1515768 |
| 062 | 206113_s_at | RAB5A, member RAS oncogene family | RAB5A | NM_004162 | 0.010821017 | 1.571063 |
| 063 | 206116_s_at | tropomyosin 1 (alpha) | TPM1 | NM_000366 | 0.000283653 | 2.0841253 |
| 064 | 206245_s_at | influenza virus NS1A binding protein | IVNS1ABP | NM_006469 | 0.003607815 | 1.5105128 |
| 065 | 206323_x_at | oligophrenin 1 | OPHN1 | NM_002547 | 0.018292218 | 1.5056778 |
| 066 | 208510_s_at | peroxisome proliferative activated receptor, gamma | PPARG | NM_015869 | 0.002361554 | 1.882336 |
| 067 | 208613_s_at | filamin B, beta (actin binding protein 278) | FLNB | AV712733 | 0.001033398 | 1.7958127 |
| 068 | 208637_x_at | actinin, alpha 1 | ACTN1 | BC003576 | 0.000448714 | 1.631627 |
| 069 | 208653_s_at | CD164 antigen, sialomucin | CD164 | AF263279 | 0.017487219 | 1.5380286 |
| 070 | 208853_s_at | calnexin | CANX | L18887 | 0.011792572 | 1.5100785 |
| 071 | 209131_s_at | synaptosomal-associated protein, 23 kDa | SNAP23 | U55936 | 0.001730693 | 1.8878508 |
| 072 | 209209_s_at | pleckstrin homology domain containing, family C (with FERM domain) member 1 | PLEKHC1 | AW469573 | 0.009551367 | 1.9820172 |
| 073 | 209314_s_at | HBS1-like (*S. cerevisiae*) | HBS1L | AK024258 | 0.00507411 | 1.6641864 |
| 074 | 209316_s_at | HBS1-like (*S. cerevisiae*) | HBS1L | BC001465 | 0.006051209 | 1.6464524 |
| 075 | 209409_at | growth factor receptor-bound protein 10 | GRB10 | D86962 | 0.01098607 | 1.7481923 |
| 076 | 209410_s_at | growth factor receptor-bound protein 10 | GRB10 | AF000017 | 0.013879589 | 1.701537 |
| 077 | 209537_at | exostoses (multiple)-like 2 | EXTL2 | AF000416 | 0.003979554 | 1.5687809 |
| 078 | 210845_s_at | plasminogen activator, urokinase receptor | PLAUR | U08839 | 0.007479298 | 1.7924315 |
| 079 | 210892_s_at | general transcription factor II,i | GTF2I | BC004472 | 0.003141172 | 1.619537 |
| 080 | 210933_s_at | fascin homolog 1, actin-bundling protein (*Strongylocentrotus purpuratus*) | FSCN1 | BC004908 | 0.00342191 | 1.906748 |
| 081 | 210987_x_at | tropomyosin 1 (alpha) | TPM1 | M19267 | 0.004614187 | 1.6935222 |
| 082 | 211299_s_at | flotillin 2 | FLOT2 | BC003683 | 0.015057402 | 1.5387125 |
| 083 | 211506_s_at | interleukin 8 | IL8 | AF043337 | 0.005428782 | 2.867063 |
| 084 | 211559_s_at | cyclin G2 | CCNG2 | L49506 | 0.010491861 | 1.8367761 |
| 085 | 211599_x_at | met proto-oncogene (hepatocyte growth factor receptor) | MET | U19348 | 0.019789577 | 1.9247686 |
| 086 | 211651_s_at | laminin, beta 1 | LAMB1 | M20206 | 0.000418344 | 1.997547 |
| 087 | 211668_s_at | plasminogen activator, urokinase | PLAU | K03226 | 0.00240352 | 2.8568754 |

-continued

| No. | Probe Set ID | Gene Name | Gene Symbol | Genbank Accession # | T-test p-value | Fold change (abs) |
|---|---|---|---|---|---|---|
| 088 | 211864_s_at | fer-1-like 3, myoferlin (*C. elegans*) | FER1L3 | AF207990 | 0.011889962 | 1.7860718 |
| 089 | 211924_s_at | plasminogen activator, urokinase receptor | PLAUR | AY029180 | 0.011789334 | 1.8189595 |
| 090 | 211981_at | collagen, type IV, alpha 1 | COL4A1 | NM_001845 | 0.007531395 | 1.8490748 |
| 091 | 212012_at | peroxidasin homolog (*Drosophila*) | PXDN | BF342851 | 0.016265145 | 1.8463359 |
| 092 | 212660_at | PHD finger protein 15 | PHF15 | AI735639 | 0.007391165 | 1.5595657 |
| 093 | 212720_at | poly(A) polymerase alpha | PAPOLA | AI670847 | 0.016607396 | 1.5904158 |
| 094 | 212907_at | Solute carrier family 30 (zinc transporter), member 1 | SLC30A1 | AI972416 | 0.002460855 | 1.63999 |
| 095 | 213288_at | O-acyltransferase (membrane bound) domain containing 2 | OACT2 | AI761250 | 0.010427832 | 1.6232696 |
| 096 | 213457_at | malignant fibrous histiocytoma amplified sequence 1 | MFHAS1 | BF739959 | 0.003050241 | 1.8505166 |
| 097 | 213624_at | sphingomyelin phosphodiesterase, acid-like 3A | SMPDL3A | AA873600 | 0.005912889 | 1.8562527 |
| 098 | 213742_at | splicing factor, arginine/serine-rich 11 | SFRS11 | AW241752 | 0.006011819 | 1.9170463 |
| 099 | 214121_x_at | PDZ and LIM domain 7 (enigma) | PDLIM7 | AA086229 | 5.50514E−05 | 1.5048952 |
| 100 | 214196_s_at | tripeptidyl peptidase I | TPP1 | AA602532 | 0.015398935 | 1.5939685 |
| 101 | 214544_s_at | synaptosomal-associated protein, 23 kDa | SNAP23 | NM_003825 | 0.003539713 | 1.8040004 |
| 102 | 214581_x_at | tumor necrosis factor receptor superfamily, member 21 | TNFRSF21 | BE568134 | 0.002274355 | 2.2189345 |
| 103 | 214701_s_at | fibronectin 1 | FN1 | AJ276395 | 0.001182322 | 2.071262 |
| 104 | 214866_at | plasminogen activator, urokinase receptor | PLAUR | X74039 | 0.003173471 | 1.7340106 |
| 105 | 214895_s_at | ADAM metallopeptidase domain 10 | ADAM10 | AU135154 | 0.004170008 | 1.9890832 |
| 106 | 215501_s_at | dual specificity phosphatase 10 | DUSP10 | AK022513 | 0.018290011 | 1.5388945 |
| 107 | 216035_x_at | transcription factor 7-like 2 (T-cell specific, HMG-box) | TCF7L2 | AV721430 | 0.000657631 | 1.7091621 |
| 108 | 216511_s_at | transcription factor 7-like 2 (T-cell specific, HMG-box) | TCF7L2 | AJ270770 | 0.004103699 | 1.5264177 |
| 109 | 216915_s_at | protein tyrosine phosphatase, non-receptor type 12 | PTPN12 | S69182 | 0.005493577 | 1.6935816 |
| 110 | 216971_s_at | plectin 1, intermediate filament binding protein 500 kDa | PLEC1 | Z54367 | 0.01826363 | 1.7186335 |
| 111 | 217188_s_at | chromosome 14 open reading frame 1 | C14orf1 | AC007182 | 0.011925477 | 1.6185476 |
| 112 | 217448_s_at | chromosome 14 open reading frame 92 similar to Epidermal Langerhans cell protein LCP1 | C14orf92 LOC285412 | AL117508 | 0.007782524 | 1.5433311 |
| 113 | 217492_s_at | phosphatase and tensin homolog (mutated in multiple advanced cancers 1) | PTEN | AF023139 | 0.007220107 | 1.5624946 |
| 114 | 218000_s_at | pleckstrin homology-like domain, family A, member 1 | PHLDA1 | NM_007350 | 0.016502094 | 1.6960312 |
| 115 | 218077_s_at | zinc finger, DHHC-type containing 3 | ZDHHC3 | BE542551 | 0.01684034 | 1.5417765 |
| 116 | 218078_s_at | zinc finger, DHHC-type containing 3 | ZDHHC3 | NM_016598 | 0.010970607 | 1.5836283 |
| 117 | 218435_at | DnaJ (Hsp40) homolog, subfamily C, member 15 | DNAJC15 | NM_013238 | 0.019865552 | 1.7292447 |
| 118 | 218644_at | pleckstrin 2 | PLEK2 | NM_016445 | 0.000675608 | 2.7071812 |
| 119 | 218748_s_at | SEC10-like 1 (*S. cerevisiae*) | SEC10L1 | NM_006544 | 0.012352341 | 1.7368068 |
| 120 | 218815_s_at | transmembrane protein 51 | TMEM51 | NM_018022 | 0.000753902 | 1.6477742 |
| 121 | 218826_at | solute carrier family 35, member F2 | SLC35F2 | NM_017515 | 0.009280122 | 1.6340361 |
| 122 | 218854_at | squamous cell carcinoma antigen recognized by T cells 2 | SART2 | NM_013352 | 0.014419112 | 1.6285655 |
| 123 | 218856_at | tumor necrosis factor receptor superfamily, member 21 | TNFRSF21 | NM_016629 | 0.01292243 | 1.617686 |
| 124 | 218885_s_at | UDP-N-acetyl-alpha-D-galactosamine:polypeptide N-acetylgalactosaminyltransferase 12 (GalNAc-T12) | GALNT12 | NM_024642 | 0.014052196 | 1.6402073 |
| 125 | 219410_at | transmembrane protein 45A | TMEM45A | NM_018004 | 0.018847797 | 2.0938365 |
| 126 | 219603_s_at | zinc finger protein 226 | ZNF226 | NM_015919 | 0.005593323 | 1.5408667 |
| 127 | 220199_s_at | chromosome 1 open reading frame 80 | C1orf80 | NM_022831 | 0.016323 | 1.5315142 |
| 128 | 220617_s_at | zinc finger protein 532 | ZNF532 | NM_018181 | 0.001976648 | 1.5441327 |
| 129 | 221268_s_at | sphingosine-1-phosphate phosphatase 1 | SGPP1 | NM_030791 | 0.008873873 | 1.9432548 |
| 130 | 221881_s_at | chloride intracellular channel 4 | CLIC4 | AI638420 | 0.004401053 | 1.7742935 |
| 131 | 222399_s_at | SM-11044 binding protein | SMBP | BG104571 | 0.00011337 | 1.5270268 |
| 132 | 222449_at | transmembrane, prostate androgen induced RNA | TMEPAI | AL035541 | 0.005303006 | 2.2757804 |
| 133 | 222528_s_at | solute carrier family 25, member 37 | SLC25A37 | BG251467 | 0.014745607 | 1.738053 |
| 134 | 222540_s_at | hepatitis B virus x associated protein | HBXAP | BG286920 | 0.005694628 | 1.5068418 |
| 135 | 222692_s_at | fibronectin type III domain containing 3B | FNDC3B | BF444916 | 0.001075083 | 1.5835624 |
| 136 | 222693_at | fibronectin type III domain containing 3B | FNDC3B | BF444916 | 0.000622161 | 1.7766397 |
| 137 | 222773_s_at | UDP-N-acetyl-alpha-D-galactosamine:polypeptide N-acetylgalactosaminyltransferase 12 (GalNAc-T12) | GALNT12 | AA554045 | 0.003090952 | 1.8790901 |
| 138 | 223577_x_at | PRO1073 protein | PRO1073 | AA827878 | 0.003659447 | 1.6790042 |
| 139 | 223940_x_at | metastasis associated lung adenocarcinoma transcript 1 (non-coding RNA) | MALAT1 | AF132202 | 0.016841894 | 1.9524238 |

-continued

| No. | Probe Set ID | Gene Name | Gene Symbol | Genbank Accession # | T-test p-value | Fold change (abs) |
|---|---|---|---|---|---|---|
| 140 | 224558_s_at | metastasis associated lung adenocarcinoma transcript 1 (non-coding RNA) | MALAT1 | AI446756 | 0.012874936 | 1.6367766 |
| 141 | 224674_at | tweety homolog 3 (*Drosophila*) | TTYH3 | AI934753 | 0.002428954 | 1.6452742 |
| 142 | 224733_at | chemokine-like factor superfamily 3 | CKLFSF3 | AL574900 | 0.013543638 | 1.5199631 |
| 143 | 224802_at | Nedd4 family interacting protein 2 | NDFIP2 | AA019338 | 0.013437813 | 1.5261155 |
| 144 | 225021_at | zinc finger protein 532 | ZNF532 | AA861416 | 0.002285053 | 1.6213596 |
| 145 | 225140_at | Kruppel-like factor 3 (basic) | KLF3 | BF438116 | 0.016804362 | 1.5368354 |
| 146 | 225168_at | FERM domain containing 4A | FRMD4A | T78406 | 0.006987929 | 1.5712297 |
| 147 | 225424_at | glycerol-3-phosphate acyltransferase, mitochondrial | GPAM | AB046780 | 0.000390623 | 1.7006425 |
| 148 | 225503_at | dehydrogenase/reductase (SDR family) X-linked | DHRSX | AL547782 | 0.005000754 | 1.770981 |
| 149 | 225567_at | Hypothetical LOC388114 | LOC388114 | BE207755 | 0.003047524 | 1.6990312 |
| 150 | 225609_at | glutathione reductase | GSR | AI888037 | 0.004693668 | 1.8490914 |
| 151 | 225842_at | Pleckstrin homology-like domain, family A, member 1 | PHLDA1 | AK026181 | 0.014052763 | 1.8735564 |
| 152 | 226084_at | microtubule-associated protein 1B | MAP1B | AA554833 | 0.016480966 | 1.9064581 |
| 153 | 226352_at | Junction-mediating and regulatory protein | JMY | BF447037 | 0.001219355 | 1.5196482 |
| 154 | 226726_at | O-acyltransferase (membrane bound) domain containing 2 | OACT2 | W63676 | 0.005363467 | 1.8277074 |
| 155 | 226780_s_at | hypothetical protein HSPC268 | HSPC268 | BF540829 | 0.001859941 | 1.5185972 |
| 156 | 227257_s_at | chromosome 10 open reading frame 46 | C10orf46 | AW973842 | 0.000646104 | 1.6094143 |
| 157 | 227628_at | similar to RIKEN cDNA 2310016C16 | LOC493869 | AL571557 | 0.006222301 | 2.0978951 |
| 158 | 227808_at | DnaJ (Hsp40) homolog, subfamily C, member 15 | DNAJC15 | AI091398 | 0.01153802 | 1.7936606 |
| 159 | 230206_at | Dedicator of cytokinesis 5 | DOCK5 | AI692645 | 0.005127667 | 1.6694399 |
| 160 | 231735_s_at | PRO1073 protein | PRO1073 | NM_014086 | 0.004784999 | 1.72546 |
| 161 | 231823_s_at | KIAA1295 | KIAA1295 | BG054798 | 0.002478401 | 1.5713933 |
| 162 | 235587_at | hypothetical protein LOC202781 | LOC202781 | BG400596 | 0.018314553 | 1.5202585 |
| 163 | 235879_at | Muscleblind-like (*Drosophila*) | MBNL1 | AI697540 | 0.002645486 | 2.0540323 |
| 164 | 238558_at | Muscleblind-like (*Drosophila*) | MBNL1 | AI445833 | 0.004576562 | 1.805269 |
| 165 | 238563_at | Abl-interactor 1 | ABI1 | AV762916 | 0.012934915 | 1.6069295 |
| 166 | 238701_x_at | FLJ45803 protein | FLJ45803 | BE176566 | 0.01719282 | 1.5133282. |

11. A kit for diagnosing the risk of lung cancer recurrence in a lung cancer patient or after a patient has lung cancer treatment, the kit comprising at least one probe or probe set specific to each target nucleic acid in a set of target nucleic acids consisting of target nucleic acids in Tables 1, below

| No. | Probe Set ID | Gene Name | Gene Symbol | Genbank Accession # | T-test p-value | Fold change (abs) |
|---|---|---|---|---|---|---|
| 001 | 1552486_s_at | lactamase, beta | LACTB | NM_171846 | 0.005162234 | 1.522293 |
| 002 | 1553105_s_at | desmoglein 2 | DSG2 | NM_001943 | 0.019467462 | 2.3323212 |
| 003 | 1553530_a_at | integrin, beta 1 (fibronectin receptor, beta polypeptide, antigen CD29 includes MDF2, MSK12) | ITGB1 | NM_033669 | 0.01684671 | 1.7791877 |
| 004 | 1553678_a_at | integrin, beta 1 (fibronectin receptor, beta polypeptide, antigen CD29 includes MDF2, MSK12) | ITGB1 | NM_133376 | 0.012459265 | 1.7374601 |
| 005 | 1554067_at | hypothetical protein FLJ32549 | FLJ32549 | BC036246 | 0.002290308 | 1.5143739 |
| 006 | 1554761_a_at | hypothetical protein FLJ20397 | FLJ20397 | BC010850 | 0.001210456 | 1.6267678 |
| 007 | 1555326_a_at | ADAM metallopeptidase domain 9 (meltrin gamma) | ADAM9 | AF495383 | 0.012324799 | 2.1980886 |
| 008 | 1555564_a_at | I factor (complement) | IF | BC020718 | 0.007528743 | 2.5875902 |
| 009 | 1555705_a_at | chemokine-like factor superfamily 3 | CKLFSF3 | AY166714 | 0.004961676 | 1.8687251 |
| 010 | 1557987_at | PI-3-kinase-related kinase SMG-1 - like locus | LOC641298 | BC042832 | 0.010989661 | 1.7944587 |
| 011 | 1558678_s_at | metastasis associated lung adenocarcinoma transcript 1 (non-coding RNA) | MALAT1 | BE708432 | 0.00670648 | 1.6990829 |
| 012 | 160020_at | matrix metallopeptidase 14 (membrane-inserted) | MMP14 | Z48481 | 0.005463324 | 1.5193439 |
| 013 | 200604_s_at | protein kinase, cAMP-dependent, regulatory, type I, alpha (tissue specific extinguisher 1) | PRKAR1A | M18468 | 0.017312625 | 1.5803499 |
| 014 | 200615_s_at | adaptor-related protein complex 2, beta 1 subunit | AP2B1 | AL567295 | 0.007407852 | 1.6839108 |
| 015 | 200864_s_at | RAB11A, member RAS oncogene family | RAB11A | NM_004663 | 0.000163535 | 1.5653288 |

-continued

| No. | Probe Set ID | Gene Name | Gene Symbol | Genbank Accession # | T-test p-value | Fold change (abs) |
|---|---|---|---|---|---|---|
| 016 | 200922_at | KDEL (Lys-Asp-Glu-Leu) endoplasmic reticulum protein retention receptor 1 | KDELR1 | NM_006801 | 0.004791257 | 1.638207 |
| 017 | 201020_at | tyrosine 3-monooxygenase/tryptophan 5-monooxygenase activation protein, eta polypeptide | YWHAH | NM_003405 | 0.009279575 | 1.5148095 |
| 018 | 201179_s_at | guanine nucleotide binding protein (G protein), alpha inhibiting activity polypeptide 3 | GNAI3 | J03005 | 0.014834337 | 1.5069977 |
| 019 | 201309_x_at | chromosome 5 open reading frame 13 | C5orf13 | U36189 | 0.011555359 | 2.1326842 |
| 020 | 201363_s_at | influenza virus NS1A binding protein | IVNS1ABP | AB020657 | 0.00119686 | 1.5838884 |
| 021 | 201505_at | laminin, beta 1 | LAMB1 | NM_002291 | 0.000568398 | 1.8073287 |
| 022 | 201506_at | transforming growth factor, beta-induced, 68 kDa | TGFBI | NM_000358 | 0.008768089 | 1.9059453 |
| 023 | 201548_s_at | Jumonji, AT rich interactive domain 1B (RBP2-like) | JARID1B | W02593 | 0.010550437 | 1.5276276 |
| 024 | 201559_s_at | chloride intracellular channel 4 | CLIC4 | AF109196 | 0.002245945 | 2.1570368 |
| 025 | 201564_s_at | fascin homolog 1, actin-bundling protein (*Strongylocentrotus purpuratus*) | FSCN1 | NM_003088 | 0.007795681 | 2.1724482 |
| 026 | 201578_at | podocalyxin-like | PODXL | NM_005397 | 0.00303411 | 1.8943018 |
| 027 | 201617_x_at | caldesmon 1 | CALD1 | NM_004342 | 0.01926877 | 1.8294148 |
| 028 | 201646_at | scavenger receptor class B, member 2 | SCARB2 | AA885297 | 0.006063032 | 1.6768507 |
| 029 | 201647_s_at | scavenger receptor class B, member 2 | SCARB2 | NM_005506 | 0.015885489 | 1.6841809 |
| 030 | 201695_s_at | nucleoside phosphorylase | NP | NM_000270 | 0.018524641 | 1.6833633 |
| 031 | 201722_s_at | UDP-N-acetyl-alpha-D-galactosamine:polypeptide N-acetylgalactosaminyltransferase 1 (GalNAc-T1) | GALNT1 | AV692127 | 0.009770202 | 1.5369248 |
| 032 | 201918_at | Solute carrier family 25, member 36 | SLC25A36 | AI927944 | 0.00259865 | 1.6228764 |
| 033 | 201942_s_at | carboxypeptidase D | CPD | D85390 | 0.017363481 | 1.7431495 |
| 034 | 202267_at | laminin, gamma 2 | LAMC2 | NM_005562 | 0.004330024 | 2.8191426 |
| 035 | 202543_s_at | glia maturation factor, beta | GMFB | BC005359 | 0.008048828 | 1.5254242 |
| 036 | 202604_x_at | ADAM metallopeptidase domain 10 | ADAM10 | NM_001110 | 0.002003783 | 1.767903 |
| 037 | 202627_s_at | serpin peptidase inhibitor, clade E (nexin, plasminogen activator inhibitor type 1), member 1 | SERPINE1 | AL574210 | 0.00091248 | 3.0523725 |
| 038 | 202628_s_at | serpin peptidase inhibitor, clade E (nexin, plasminogen activator inhibitor type 1), member 1 | SERPINE1 | NM_000602 | 0.00504642 | 2.6835847 |
| 039 | 202817_s_at | synovial sarcoma translocation, chromosome 18 | SS18 | NM_005637 | 0.005462693 | 1.5148987 |
| 040 | 202859_x_at | interleukin 8 | IL8 | NM_000584 | 0.014948112 | 2.1844351 |
| 041 | 202936_s_at | SRY (sex determining region Y)-box 9 (campomelic dysplasia, autosomal sex-reversal | SOX9 | NM_000346 | 0.019816045 | 2.2876046 |
| 042 | 202949_s_at | four and a half LIM domains 2 | FHL2 | NM_001450 | 0.006776552 | 2.2249734 |
| 043 | 202998_s_at | lysyl oxidase-like 2 | LOXL2 | NM_002318 | 0.006687925 | 2.0231075 |
| 044 | 203066_at | B cell RAG associated protein | GALNAC4S-6ST | NM_014863 | 0.00419499 | 1.5032523 |
| 045 | 203072_at | myosin IE | MYO1E | NM_004998 | 0.000449373 | 1.5877136 |
| 046 | 203293_s_at | lectin, mannose-binding, 1 | LMAN1 | NM_005570 | 0.002661762 | 1.9762497 |
| 047 | 203294_s_at | lectin, mannose-binding, 1 | LMAN1 | U09716 | 0.000473367 | 1.9764429 |
| 048 | 203414_at | monocyte to macrophage differentiation-associated | MMD | NM_012329 | 0.001585437 | 1.6128623 |
| 049 | 203553_s_at | mitogen-activated protein kinase kinase kinase kinase 5 | MAP4K5 | NM_006575 | 0.010453912 | 1.5251595 |
| 050 | 203924_at | glutathione S-transferase A1 | GSTA1 | NM_000846 | 0.004046575 | 4.2017674 |
| 051 | 203988_s_at | fucosyltransferase 8 (alpha (1,6) fucosyltransferase) | FUT8 | NM_004480 | 0.01139016 | 1.6090198 |
| 052 | 204426_at | transmembrane emp24 domain trafficking protein 2 | TMED2 | NM_006815 | 0.015985437 | 1.6165011 |
| 053 | 204470_at | chemokine (C-X-C motif) ligand 1 (melanoma growth stimulating activity, alpha) | CXCL1 | NM_001511 | 0.001788037 | 3.218731 |
| 054 | 204702_s_at | nuclear factor (erythroid-derived 2)-like 3 | NFE2L3 | NM_004289 | 0.015985157 | 1.7023398 |
| 055 | 204790_at | SMAD, mothers against DPP homolog 7 (*Drosophila*) | SMAD7 | NM_005904 | 0.013379821 | 1.7179344 |
| 056 | 204944_at | protein tyrosine phosphatase, receptor type, G | PTPRG | NM_002841 | 0.004963213 | 1.769544 |
| 057 | 204989_s_at | integrin, beta 4 | ITGB4 | BF305661 | 0.012746719 | 2.1320713 |
| 058 | 205120_s_at | sarcoglycan, beta (43 kDa dystrophin-associated glycoprotein) | SGCB | U29586 | 0.013908542 | 1.7317705 |
| 059 | 205180_s_at | ADAM metallopeptidase domain 8 | ADAM8 | NM_001109 | 0.000473816 | 2.054043 |
| 060 | 205479_s_at | plasminogen activator, urokinase | PLAU | NM_002658 | 0.003415823 | 2.4370956 |
| 061 | 206025_s_at | tumor necrosis factor, alpha-induced protein 6 | TNFAIP6 | AW188198 | 0.013965369 | 2.1515768 |
| 062 | 206113_s_at | RAB5A, member RAS oncogene family | RAB5A | NM_004162 | 0.010821017 | 1.571063 |
| 063 | 206116_s_at | tropomyosin 1 (alpha) | TPM1 | NM_000366 | 0.000283653 | 2.0841253 |
| 064 | 206245_s_at | influenza virus NS1A binding protein | IVNS1ABP | NM_006469 | 0.003607815 | 1.5105128 |
| 065 | 206323_x_at | oligophrenin 1 | OPHN1 | NM_002547 | 0.018292218 | 1.5056778 |

-continued

| No. | Probe Set ID | Gene Name | Gene Symbol | Genbank Accession # | T-test p-value | Fold change (abs) |
|---|---|---|---|---|---|---|
| 066 | 208510_s_at | peroxisome proliferative activated receptor, gamma | PPARG | NM_015869 | 0.002361554 | 1.882336 |
| 067 | 208613_s_at | filamin B, beta (actin binding protein 278) | FLNB | AV712733 | 0.001033398 | 1.7958127 |
| 068 | 208637_x_at | actinin, alpha 1 | ACTN1 | BC003576 | 0.000448714 | 1.631627 |
| 069 | 208653_s_at | CD164 antigen, sialomucin | CD164 | AF263279 | 0.017487219 | 1.5380286 |
| 070 | 208853_s_at | calnexin | CANX | L18887 | 0.011792572 | 1.5100785 |
| 071 | 209131_s_at | synaptosomal-associated protein, 23 kDa | SNAP23 | U55936 | 0.001730693 | 1.8878508 |
| 072 | 209209_s_at | pleckstrin homology domain containing, family C (with FERM domain) member 1 | PLEKHC1 | AW469573 | 0.009551367 | 1.9820172 |
| 073 | 209314_s_at | HBS1-like (*S. cerevisiae*) | HBS1L | AK024258 | 0.00507411 | 1.6641864 |
| 074 | 209316_s_at | HBS1-like (*S. cerevisiae*) | HBS1L | BC001465 | 0.006051209 | 1.6464524 |
| 075 | 209409_at | growth factor receptor-bound protein 10 | GRB10 | D86962 | 0.01098607 | 1.7481923 |
| 076 | 209410_s_at | growth factor receptor-bound protein 10 | GRB10 | AF000017 | 0.013879589 | 1.701537 |
| 077 | 209537_at | exostoses (multiple)-like 2 | EXTL2 | AF000416 | 0.003979554 | 1.5687809 |
| 078 | 210845_s_at | plasminogen activator, urokinase receptor | PLAUR | U08839 | 0.007479298 | 1.7924315 |
| 079 | 210892_s_at | general transcription factor II,i | GTF2I | BC004472 | 0.003141172 | 1.619537 |
| 080 | 210933_s_at | fascin homolog 1, actin-bundling protein (*Strongylocentrotus purpuratus*) | FSCN1 | BC004908 | 0.00342191 | 1.906748 |
| 081 | 210987_x_at | tropomyosin 1 (alpha) | TPM1 | M19267 | 0.004614187 | 1.6935222 |
| 082 | 211299_s_at | flotillin 2 | FLOT2 | BC003683 | 0.015057402 | 1.5387125 |
| 083 | 211506_s_at | interleukin 8 | IL8 | AF043337 | 0.005428782 | 2.867063 |
| 084 | 211559_s_at | cyclin G2 | CCNG2 | L49506 | 0.010491861 | 1.8367761 |
| 085 | 211599_x_at | met proto-oncogene (hepatocyte growth factor receptor) | MET | U19348 | 0.019789577 | 1.9247686 |
| 086 | 211651_s_at | laminin, beta 1 | LAMB1 | M20206 | 0.000418344 | 1.997547 |
| 087 | 211668_s_at | plasminogen activator, urokinase | PLAU | K03226 | 0.00240352 | 2.8568754 |
| 088 | 211864_s_at | fer-1-like 3, myoferlin (*C. elegans*) | FER1L3 | AF207990 | 0.011889962 | 1.7860718 |
| 089 | 211924_s_at | plasminogen activator, urokinase receptor | PLAUR | AY029180 | 0.011789334 | 1.8189595 |
| 090 | 211981_at | collagen, type IV, alpha 1 | COL4A1 | NM_001845 | 0.007531395 | 1.8490748 |
| 091 | 212012_at | peroxidasin homolog (*Drosophila*) | PXDN | BF342851 | 0.016265145 | 1.8463359 |
| 092 | 212660_at | PHD finger protein 15 | PHF15 | AI735639 | 0.007391165 | 1.5595657 |
| 093 | 212720_at | poly(A) polymerase alpha | PAPOLA | AI670847 | 0.016607396 | 1.5904158 |
| 094 | 212907_at | Solute carrier family 30 (zinc transporter), member 1 | SLC30A1 | AI972416 | 0.002460855 | 1.63999 |
| 095 | 213288_at | O-acyltransferase (membrane bound) domain containing 2 | OACT2 | AI761250 | 0.010427832 | 1.6232696 |
| 096 | 213457_at | malignant fibrous histiocytoma amplified sequence 1 | MFHAS1 | BF739959 | 0.003050241 | 1.8505166 |
| 097 | 213624_at | sphingomyelin phosphodiesterase, acid-like 3A | SMPDL3A | AA873600 | 0.005912889 | 1.8562527 |
| 098 | 213742_at | splicing factor, arginine/serine-rich 11 | SFRS11 | AW241752 | 0.006011819 | 1.9170463 |
| 099 | 214121_x_at | PDZ and LIM domain 7 (enigma) | PDLIM7 | AA086229 | 5.50514E−05 | 1.5048952 |
| 100 | 214196_s_at | tripeptidyl peptidase I | TPP1 | AA602532 | 0.015398935 | 1.5939685 |
| 101 | 214544_s_at | synaptosomal-associated protein, 23 kDa | SNAP23 | NM_003825 | 0.003539713 | 1.8040004 |
| 102 | 214581_x_at | tumor necrosis factor receptor superfamily, member 21 | TNFRSF21 | BE568134 | 0.002274355 | 2.2189345 |
| 103 | 214701_s_at | fibronectin 1 | FN1 | AJ276395 | 0.001182322 | 2.071262 |
| 104 | 214866_at | plasminogen activator, urokinase receptor | PLAUR | X74039 | 0.003173471 | 1.7340106 |
| 105 | 214895_s_at | ADAM metallopeptidase domain 10 | ADAM10 | AU135154 | 0.004170008 | 1.9890832 |
| 106 | 215501_s_at | dual specificity phosphatase 10 | DUSP10 | AK022513 | 0.018290011 | 1.5388945 |
| 107 | 216035_x_at | transcription factor 7-like 2 (T-cell specific, HMG-box) | TCF7L2 | AV721430 | 0.000657631 | 1.7091621 |
| 108 | 216511_s_at | transcription factor 7-like 2 (T-cell specific, HMG-box) | TCF7L2 | AJ270770 | 0.004103699 | 1.5264177 |
| 109 | 216915_s_at | protein tyrosine phosphatase, non-receptor type 12 | PTPN12 | S69182 | 0.005493577 | 1.6935816 |
| 110 | 216971_s_at | plectin 1, intermediate filament binding protein 500 kDa | PLEC1 | Z54367 | 0.01826363 | 1.7186335 |
| 111 | 217188_s_at | chromosome 14 open reading frame 1 | C14orf1 | AC007182 | 0.011925477 | 1.6185476 |
| 112 | 217448_s_at | chromosome 14 open reading frame 92 similar to Epidermal Langerhans cell protein LCP1 | C14orf92 LOC285412 | AL117508 | 0.007782524 | 1.5433311 |
| 113 | 217492_s_at | phosphatase and tensin homolog (mutated in multiple advanced cancers 1) | PTEN | AF023139 | 0.007220107 | 1.5624946 |
| 114 | 218000_s_at | pleckstrin homology-like domain, family A, member 1 | PHLDA1 | NM_007350 | 0.016502094 | 1.6960312 |
| 115 | 218077_s_at | zinc finger, DHHC-type containing 3 | ZDHHC3 | BE542551 | 0.01684034 | 1.5417765 |
| 116 | 218078_s_at | zinc finger, DHHC-type containing 3 | ZDHHC3 | NM_016598 | 0.010970607 | 1.5836283 |
| 117 | 218435_at | DnaJ (Hsp40) homolog, subfamily C, member 15 | DNAJC15 | NM_013238 | 0.019865552 | 1.7292447 |
| 118 | 218644_at | pleckstrin 2 | PLEK2 | NM_016445 | 0.000675608 | 2.7071812 |
| 119 | 218748_s_at | SEC10-like 1 (*S. cerevisiae*) | SEC10L1 | NM_006544 | 0.012352341 | 1.7368068 |

| No. | Probe Set ID | Gene Name | Gene Symbol | Genbank Accession # | T-test p-value | Fold change (abs) |
|---|---|---|---|---|---|---|
| 120 | 218815_s_at | transmembrane protein 51 | TMEM51 | NM_018022 | 0.000753902 | 1.6477742 |
| 121 | 218826_at | solute carrier family 35, member F2 | SLC35F2 | NM_017515 | 0.009280122 | 1.6340361 |
| 122 | 218854_at | squamous cell carcinoma antigen recognized by T cells 2 | SART2 | NM_013352 | 0.014419112 | 1.6285655 |
| 123 | 218856_at | tumor necrosis factor receptor superfamily, member 21 | TNFRSF21 | NM_016629 | 0.01292243 | 1.617686 |
| 124 | 218885_s_at | UDP-N-acetyl-alpha-D-galactosamine:polypeptide N-acetylgalactosaminyltransferase 12 (GalNAc-T12) | GALNT12 | NM_024642 | 0.014052196 | 1.6402073 |
| 125 | 219410_at | transmembrane protein 45A | TMEM45A | NM_018004 | 0.018847797 | 2.0938365 |
| 126 | 219603_s_at | zinc finger protein 226 | ZNF226 | NM_015919 | 0.005593323 | 1.5408667 |
| 127 | 220199_s_at | chromosome 1 open reading frame 80 | C1orf80 | NM_022831 | 0.016323 | 1.5315142 |
| 128 | 220617_s_at | zinc finger protein 532 | ZNF532 | NM_018181 | 0.001976648 | 1.5441327 |
| 129 | 221268_s_at | sphingosine-1-phosphate phosphatase 1 | SGPP1 | NM_030791 | 0.008873873 | 1.9432548 |
| 130 | 221881_s_at | chloride intracellular channel 4 | CLIC4 | AI638420 | 0.004401053 | 1.7742935 |
| 131 | 222399_s_at | SM-11044 binding protein | SMBP | BG104571 | 0.00011337 | 1.5270268 |
| 132 | 222449_at | transmembrane, prostate androgen induced RNA | TMEPAI | AL035541 | 0.005303006 | 2.2757804 |
| 133 | 222528_s_at | solute carrier family 25, member 37 | SLC25A37 | BG251467 | 0.014745607 | 1.738053 |
| 134 | 222540_s_at | hepatitis B virus x associated protein | HBXAP | BG286920 | 0.005694628 | 1.5068418 |
| 135 | 222692_s_at | fibronectin type III domain containing 3B | FNDC3B | BF444916 | 0.001075083 | 1.5835624 |
| 136 | 222693_at | fibronectin type III domain containing 3B | FNDC3B | BF444916 | 0.000622161 | 1.7766397 |
| 137 | 222773_s_at | UDP-N-acetyl-alpha-D-galactosamine:polypeptide N-acetylgalactosaminyltransferase 12 (GalNAc-T12) | GALNT12 | AA554045 | 0.003090952 | 1.8790901 |
| 138 | 223577_x_at | PRO1073 protein | PRO1073 | AA827878 | 0.003659447 | 1.6790042 |
| 139 | 223940_x_at | metastasis associated lung adenocarcinoma transcript 1 (non-coding RNA) | MALAT1 | AF132202 | 0.016841894 | 1.9524238 |
| 140 | 224558_s_at | metastasis associated lung adenocarcinoma transcript 1 (non-coding RNA) | MALAT1 | AI446756 | 0.012874936 | 1.6367766 |
| 141 | 224674_at | tweety homolog 3 (*Drosophila*) | TTYH3 | AI934753 | 0.002428954 | 1.6452742 |
| 142 | 224733_at | chemokine-like factor superfamily 3 | CKLFSF3 | AL574900 | 0.013543638 | 1.5199631 |
| 143 | 224802_at | Nedd4 family interacting protein 2 | NDFIP2 | AA019338 | 0.013437813 | 1.5261155 |
| 144 | 225021_at | zinc finger protein 532 | ZNF532 | AA861416 | 0.002285053 | 1.6213596 |
| 145 | 225140_at | Kruppel-like factor 3 (basic) | KLF3 | BF438116 | 0.016804362 | 1.5368354 |
| 146 | 225168_at | FERM domain containing 4A | FRMD4A | T78406 | 0.006987929 | 1.5712297 |
| 147 | 225424_at | glycerol-3-phosphate acyltransferase, mitochondrial | GPAM | AB046780 | 0.000390623 | 1.7006425 |
| 148 | 225503_at | dehydrogenase/reductase (SDR family) X-linked | DHRSX | AL547782 | 0.005000754 | 1.770981 |
| 149 | 225567_at | Hypothetical LOC388114 | LOC388114 | BE207755 | 0.003047524 | 1.6990312 |
| 150 | 225609_at | glutathione reductase | GSR | AI888037 | 0.004693668 | 1.8490914 |
| 151 | 225842_at | Pleckstrin homology-like domain, family A, member 1 | PHLDA1 | AK026181 | 0.014052763 | 1.8735564 |
| 152 | 226084_at | microtubule-associated protein 1B | MAP1B | AA554833 | 0.016480966 | 1.9064581 |
| 153 | 226352_at | Junction-mediating and regulatory protein | JMY | BF447037 | 0.001219355 | 1.5196482 |
| 154 | 226726_at | O-acyltransferase (membrane bound) domain containing 2 | OACT2 | W63676 | 0.005363467 | 1.8277074 |
| 155 | 226780_s_at | hypothetical protein HSPC268 | HSPC268 | BF540829 | 0.001859941 | 1.5185972 |
| 156 | 227257_s_at | chromosome 10 open reading frame 46 | C10orf46 | AW973842 | 0.000646104 | 1.6094143 |
| 157 | 227628_at | similar to RIKEN cDNA 2310016C16 | LOC493869 | AL571557 | 0.006222301 | 2.0978951 |
| 158 | 227808_at | DnaJ (Hsp40) homolog, subfamily C, member 15 | DNAJC15 | AI091398 | 0.01153802 | 1.7936606 |
| 159 | 230206_at | Dedicator of cytokinesis 5 | DOCK5 | AI692645 | 0.005127667 | 1.6694399 |
| 160 | 231735_s_at | PRO1073 protein | PRO1073 | NM_014086 | 0.004784999 | 1.72546 |
| 161 | 231823_s_at | KIAA1295 | KIAA1295 | BG054798 | 0.002478401 | 1.5713933 |
| 162 | 235587_at | hypothetical protein LOC202781 | LOC202781 | BG400596 | 0.018314553 | 1.5202585 |
| 163 | 235879_at | Muscleblind-like (*Drosophila*) | MBNL1 | AI697540 | 0.002645486 | 2.0540323 |
| 164 | 238558_at | Muscleblind-like (*Drosophila*) | MBNL1 | AI445833 | 0.004576562 | 1.805269 |
| 165 | 238563_at | Abl-interactor 1 | ABI1 | AV762916 | 0.012934915 | 1.6069295 |
| 166 | 238701_x_at | FLJ45803 protein | FLJ45803 | BE176566 | 0.01719282 | 1.5133282. |

12. The kit of claim 11, wherein the probe or probe set is immobilized on a microarray.

13. A kit for diagnosing the risk of lung cancer recurrence in a lung cancer patient or after a patient has lung cancer treatment, comprising a sense and anti-sense primer pair for each target nucleic acid in a set of target nucleic acids consisting of target nucleic acids in Tables 1, below

| No. | Probe Set ID | Gene Name | Gene Symbol | Genbank Accession # | T-test p-value | Fold change (abs) |
|---|---|---|---|---|---|---|
| 001 | 1552486_s_at | lactamase, beta | LACTB | NM_171846 | 0.005162234 | 1.522293 |
| 002 | 1553105_s_at | desmoglein 2 | DSG2 | NM_001943 | 0.019467462 | 2.3323212 |
| 003 | 1553530_a_at | integrin, beta 1 (fibronectin receptor, beta polypeptide, antigen CD29 includes MDF2, MSK12) | ITGB1 | NM_033669 | 0.01684671 | 1.7791877 |
| 004 | 1553678_a_at | integrin, beta 1 (fibronectin receptor, beta polypeptide, antigen CD29 includes MDF2, MSK12) | ITGB1 | NM_133376 | 0.012459265 | 1.7374601 |
| 005 | 1554067_at | hypothetical protein FLJ32549 | FLJ32549 | BC036246 | 0.002290308 | 1.5143739 |
| 006 | 1554761_a_at | hypothetical protein FLJ20397 | FLJ20397 | BC010850 | 0.001210456 | 1.6267678 |
| 007 | 1555326_a_at | ADAM metallopeptidase domain 9 (meltrin gamma) | ADAM9 | AF495383 | 0.012324799 | 2.1980886 |
| 008 | 1555564_a_at | I factor (complement) | IF | BC020718 | 0.007528743 | 2.5875902 |
| 009 | 1555705_a_at | chemokine-like factor superfamily 3 | CKLFSF3 | AY166714 | 0.004961676 | 1.8687251 |
| 010 | 1557987_at | PI-3-kinase-related kinase SMG-1 - like locus | LOC641298 | BC042832 | 0.010989661 | 1.7944587 |
| 011 | 1558678_s_at | metastasis associated lung adenocarcinoma transcript 1 (non-coding RNA) | MALAT1 | BE708432 | 0.00670648 | 1.6990829 |
| 012 | 160020_at | matrix metallopeptidase 14 (membrane-inserted) | MMP14 | Z48481 | 0.005463324 | 1.5193439 |
| 013 | 200604_s_at | protein kinase, cAMP-dependent, regulatory, type I, alpha (tissue specific extinguisher 1) | PRKAR1A | M18468 | 0.017312625 | 1.5803499 |
| 014 | 200615_s_at | adaptor-related protein complex 2, beta 1 subunit | AP2B1 | AL567295 | 0.007407852 | 1.6839108 |
| 015 | 200864_s_at | RAB11A, member RAS oncogene family | RAB11A | NM_004663 | 0.000163535 | 1.5653288 |
| 016 | 200922_at | KDEL (Lys-Asp-Glu-Leu) endoplasmic reticulum protein retention receptor 1 | KDELR1 | NM_006801 | 0.004791257 | 1.638207 |
| 017 | 201020_at | tyrosine 3-monooxygenase/tryptophan 5-monooxygenase activation protein, eta polypeptide | YWHAH | NM_003405 | 0.009279575 | 1.5148095 |
| 018 | 201179_s_at | guanine nucleotide binding protein (G protein), alpha inhibiting activity polypeptide 3 | GNAI3 | J03005 | 0.014834337 | 1.5069977 |
| 019 | 201309_x_at | chromosome 5 open reading frame 13 | C5orf13 | U36189 | 0.011555359 | 2.1326842 |
| 020 | 201363_s_at | influenza virus NS1A binding protein | IVNS1ABP | AB020657 | 0.00119686 | 1.5838884 |
| 021 | 201505_at | laminin, beta 1 | LAMB1 | NM_002291 | 0.000568398 | 1.8073287 |
| 022 | 201506_at | transforming growth factor, beta-induced, 68 kDa | TGFBI | NM_000358 | 0.008768089 | 1.9059453 |
| 023 | 201548_s_at | Jumonji, AT rich interactive domain 1B (RBP2-like) | JARID1B | W02593 | 0.010550437 | 1.5276276 |
| 024 | 201559_s_at | chloride intracellular channel 4 | CLIC4 | AF109196 | 0.002245945 | 2.1570368 |
| 025 | 201564_s_at | fascin homolog 1, actin-bundling protein (*Strongylocentrotus purpuratus*) | FSCN1 | NM_003088 | 0.007795681 | 2.1724482 |
| 026 | 201578_at | podocalyxin-like | PODXL | NM_005397 | 0.00303411 | 1.8943018 |
| 027 | 201617_x_at | caldesmon 1 | CALD1 | NM_004342 | 0.01926877 | 1.8294148 |
| 028 | 201646_at | scavenger receptor class B, member 2 | SCARB2 | AA885297 | 0.006063032 | 1.6768507 |
| 029 | 201647_s_at | scavenger receptor class B, member 2 | SCARB2 | NM_005506 | 0.015885489 | 1.6841809 |
| 030 | 201695_s_at | nucleoside phosphorylase | NP | NM_000270 | 0.018524641 | 1.6833633 |
| 031 | 201722_s_at | UDP-N-acetyl-alpha-D-galactosamine:polypeptide N-acetylgalactosaminyltransferase 1 (GalNAc-T1) | GALNT1 | AV692127 | 0.009770202 | 1.5369248 |
| 032 | 201918_at | Solute carrier family 25, member 36 | SLC25A36 | AI927944 | 0.00259865 | 1.6228764 |
| 033 | 201942_s_at | carboxypeptidase D | CPD | D85390 | 0.017363481 | 1.7431495 |
| 034 | 202267_at | laminin, gamma 2 | LAMC2 | NM_005562 | 0.004330024 | 2.8191426 |
| 035 | 202543_s_at | glia maturation factor, beta | GMFB | BC005359 | 0.008048828 | 1.5254242 |
| 036 | 202604_x_at | ADAM metallopeptidase domain 10 | ADAM10 | NM_001110 | 0.002003783 | 1.767903 |
| 037 | 202627_s_at | serpin peptidase inhibitor, clade E (nexin, plasminogen activator inhibitor type 1), member 1 | SERPINE1 | AL574210 | 0.00091248 | 3.0523725 |
| 038 | 202628_s_at | serpin peptidase inhibitor, clade E (nexin, plasminogen activator inhibitor type 1), member 1 | SERPINE1 | NM_000602 | 0.00504642 | 2.6835847 |
| 039 | 202817_s_at | synovial sarcoma translocation, chromosome 18 | SS18 | NM_005637 | 0.005462693 | 1.5148987 |
| 040 | 202859_x_at | interleukin 8 | IL8 | NM_000584 | 0.014948112 | 2.1844351 |
| 041 | 202936_s_at | SRY (sex determining region Y)-box 9 (campomelic dysplasia, autosomal sex-reversal | SOX9 | NM_000346 | 0.019816045 | 2.2876046 |
| 042 | 202949_s_at | four and a half LIM domains 2 | FHL2 | NM_001450 | 0.006776552 | 2.2249734 |

-continued

| No. | Probe Set ID | Gene Name | Gene Symbol | Genbank Accession # | T-test p-value | Fold change (abs) |
|---|---|---|---|---|---|---|
| 043 | 202998_s_at | lysyl oxidase-like 2 | LOXL2 | NM_002318 | 0.006687925 | 2.0231075 |
| 044 | 203066_at | B cell RAG associated protein | GALNAC4S-6ST | NM_014863 | 0.00419499 | 1.5032523 |
| 045 | 203072_at | myosin IE | MYO1E | NM_004998 | 0.000449373 | 1.5877136 |
| 046 | 203293_s_at | lectin, mannose-binding, 1 | LMAN1 | NM_005570 | 0.002661762 | 1.9762497 |
| 047 | 203294_s_at | lectin, mannose-binding, 1 | LMAN1 | U09716 | 0.000473367 | 1.9764429 |
| 048 | 203414_at | monocyte to macrophage differentiation-associated | MMD | NM_012329 | 0.001585437 | 1.6128623 |
| 049 | 203553_s_at | mitogen-activated protein kinase kinase kinase kinase 5 | MAP4K5 | NM_006575 | 0.010453912 | 1.5251595 |
| 050 | 203924_at | glutathione S-transferase A1 | GSTA1 | NM_000846 | 0.004046575 | 4.2017674 |
| 051 | 203988_s_at | fucosyltransferase 8 (alpha (1,6) fucosyltransferase) | FUT8 | NM_004480 | 0.01139016 | 1.6090198 |
| 052 | 204426_at | transmembrane emp24 domain trafficking protein 2 | TMED2 | NM_006815 | 0.015985437 | 1.6165011 |
| 053 | 204470_at | chemokine (C-X-C motif) ligand 1 (melanoma growth stimulating activity, alpha) | CXCL1 | NM_001511 | 0.001788037 | 3.218731 |
| 054 | 204702_s_at | nuclear factor (erythroid-derived 2)-like 3 | NFE2L3 | NM_004289 | 0.015985157 | 1.7023398 |
| 055 | 204790_at | SMAD, mothers against DPP homolog 7 (*Drosophila*) | SMAD7 | NM_005904 | 0.013379821 | 1.7179344 |
| 056 | 204944_at | protein tyrosine phosphatase, receptor type, G | PTPRG | NM_002841 | 0.004963213 | 1.769544 |
| 057 | 204989_s_at | integrin, beta 4 | ITGB4 | BF305661 | 0.012746719 | 2.1320713 |
| 058 | 205120_s_at | sarcoglycan, beta (43 kDa dystrophin-associated glycoprotein) | SGCB | U29586 | 0.013908542 | 1.7317705 |
| 059 | 205180_s_at | ADAM metallopeptidase domain 8 | ADAM8 | NM_001109 | 0.000473816 | 2.054043 |
| 060 | 205479_s_at | plasminogen activator, urokinase | PLAU | NM_002658 | 0.003415823 | 2.4370956 |
| 061 | 206025_s_at | tumor necrosis factor, alpha-induced protein 6 | TNFAIP6 | AW188198 | 0.013965369 | 2.1515768 |
| 062 | 206113_s_at | RAB5A, member RAS oncogene family | RAB5A | NM_004162 | 0.010821017 | 1.571063 |
| 063 | 206116_s_at | tropomyosin 1 (alpha) | TPM1 | NM_000366 | 0.000283653 | 2.0841253 |
| 064 | 206245_s_at | influenza virus NS1A binding protein | IVNS1ABP | NM_006469 | 0.003607815 | 1.5105128 |
| 065 | 206323_x_at | oligophrenin 1 | OPHN1 | NM_002547 | 0.018292218 | 1.5056778 |
| 066 | 208510_s_at | peroxisome proliferative activated receptor, gamma | PPARG | NM_015869 | 0.002361554 | 1.882336 |
| 067 | 208613_s_at | filamin B, beta (actin binding protein 278) | FLNB | AV712733 | 0.001033398 | 1.7958127 |
| 068 | 208637_x_at | actinin, alpha 1 | ACTN1 | BC003576 | 0.000448714 | 1.631627 |
| 069 | 208653_s_at | CD164 antigen, sialomucin | CD164 | AF263279 | 0.017487219 | 1.5380286 |
| 070 | 208853_s_at | calnexin | CANX | L18887 | 0.011792572 | 1.5100785 |
| 071 | 209131_s_at | synaptosomal-associated protein, 23 kDa | SNAP23 | U55936 | 0.001730693 | 1.8878508 |
| 072 | 209209_s_at | pleckstrin homology domain containing, family C (with FERM domain) member 1 | PLEKHC1 | AW469573 | 0.009551367 | 1.9820172 |
| 073 | 209314_s_at | HBS1-like (*S. cerevisiae*) | HBS1L | AK024258 | 0.00507411 | 1.6641864 |
| 074 | 209316_s_at | HBS1-like (*S. cerevisiae*) | HBS1L | BC001465 | 0.006051209 | 1.6464524 |
| 075 | 209409_at | growth factor receptor-bound protein 10 | GRB10 | D86962 | 0.01098607 | 1.7481923 |
| 076 | 209410_s_at | growth factor receptor-bound protein 10 | GRB10 | AF000017 | 0.013879589 | 1.701537 |
| 077 | 209537_at | exostoses (multiple)-like 2 | EXTL2 | AF000416 | 0.003979554 | 1.5687809 |
| 078 | 210845_s_at | plasminogen activator, urokinase receptor | PLAUR | U08839 | 0.007479298 | 1.7924315 |
| 079 | 210892_s_at | general transcription factor II,i | GTF2I | BC004472 | 0.003141172 | 1.619537 |
| 080 | 210933_s_at | fascin homolog 1, actin-bundling protein (*Strongylocentrotus purpuratus*) | FSCN1 | BC004908 | 0.00342191 | 1.906748 |
| 081 | 210987_x_at | tropomyosin 1 (alpha) | TPM1 | M19267 | 0.004614187 | 1.6935222 |
| 082 | 211299_s_at | flotillin 2 | FLOT2 | BC003683 | 0.015057402 | 1.5387125 |
| 083 | 211506_s_at | interleukin 8 | IL8 | AF043337 | 0.005428782 | 2.867063 |
| 084 | 211559_s_at | cyclin G2 | CCNG2 | L49506 | 0.010491861 | 1.8367761 |
| 085 | 211599_x_at | met proto-oncogene (hepatocyte growth factor receptor) | MET | U19348 | 0.019789577 | 1.9247686 |
| 086 | 211651_s_at | laminin, beta 1 | LAMB1 | M20206 | 0.000418344 | 1.997547 |
| 087 | 211668_s_at | plasminogen activator, urokinase | PLAU | K03226 | 0.00240352 | 2.8568754 |
| 088 | 211864_s_at | fer-1-like 3, myoferlin (*C. elegans*) | FER1L3 | AF207990 | 0.011889962 | 1.7860718 |
| 089 | 211924_s_at | plasminogen activator, urokinase receptor | PLAUR | AY029180 | 0.011789334 | 1.8189595 |
| 090 | 211981_at | collagen, type IV, alpha 1 | COL4A1 | NM_001845 | 0.007531395 | 1.8490748 |
| 091 | 212012_at | peroxidasin homolog (*Drosophila*) | PXDN | BF342851 | 0.016265145 | 1.8463359 |
| 092 | 212660_at | PHD finger protein 15 | PHF15 | AI735639 | 0.007391165 | 1.5595675 |
| 093 | 212720_at | poly(A) polymerase alpha | PAPOLA | AI670847 | 0.016607396 | 1.5904158 |
| 094 | 212907_at | Solute carrier family 30 (zinc transporter), member 1 | SLC30A1 | AI972416 | 0.002460855 | 1.63999 |
| 095 | 213288_at | O-acyltransferase (membrane bound) domain containing 2 | OACT2 | AI761250 | 0.010427832 | 1.6232696 |
| 096 | 213457_at | malignant fibrous histiocytoma amplified sequence 1 | MFHAS1 | BF739959 | 0.003050241 | 1.8505166 |
| 097 | 213624_at | sphingomyelin phosphodiesterase, acid-like 3A | SMPDL3A | AA873600 | 0.005912889 | 1.8562527 |
| 098 | 213742_at | splicing factor, arginine/serine-rich 11 | SFRS11 | AW241752 | 0.006011819 | 1.9170463 |
| 099 | 214121_x_at | PDZ and LIM domain 7 (enigma) | PDLIM7 | AA086229 | 5.50514E−05 | 1.5048952 |
| 100 | 214196_s_at | tripeptidyl peptidase I | TPP1 | AA602532 | 0.015398935 | 1.5939685 |

-continued

| No. | Probe Set ID | Gene Name | Gene Symbol | Genbank Accession # | T-test p-value | Fold change (abs) |
|---|---|---|---|---|---|---|
| 101 | 214544_s_at | synaptosomal-associated protein, 23 kDa | SNAP23 | NM_003825 | 0.003539713 | 1.8040004 |
| 102 | 214581_x_at | tumor necrosis factor receptor superfamily, member 21 | TNFRSF21 | BE568134 | 0.002274355 | 2.2189345 |
| 103 | 214701_s_at | fibronectin 1 | FN1 | AJ276395 | 0.001182322 | 2.071262 |
| 104 | 214866_at | plasminogen activator, urokinase receptor | PLAUR | X74039 | 0.003173471 | 1.7340106 |
| 105 | 214895_s_at | ADAM metallopeptidase domain 10 | ADAM10 | AU135154 | 0.004170008 | 1.9890832 |
| 106 | 215501_s_at | dual specificity phosphatase 10 | DUSP10 | AK022513 | 0.018290011 | 1.5388945 |
| 107 | 216035_x_at | transcription factor 7-like 2 (T-cell specific, HMG-box) | TCF7L2 | AV721430 | 0.000657631 | 1.7091621 |
| 108 | 216511_s_at | transcription factor 7-like 2 (T-cell specific, HMG-box) | TCF7L2 | AJ270770 | 0.004103699 | 1.5264177 |
| 109 | 216915_s_at | protein tyrosine phosphatase, non-receptor type 12 | PTPN12 | S69182 | 0.005493577 | 1.6935816 |
| 110 | 216971_s_at | plectin 1, intermediate filament binding protein 500 kDa | PLEC1 | Z54367 | 0.01826363 | 1.7186335 |
| 111 | 217188_s_at | chromosome 14 open reading frame 1 | C14orf1 | AC007182 | 0.011925477 | 1.6185476 |
| 112 | 217448_s_at | chromosome 14 open reading frame 92 similar to Epidermal Langerhans cell protein LCP1 | C14orf92 LOC285412 | AL117508 | 0.007782524 | 1.5433311 |
| 113 | 217492_s_at | phosphatase and tensin homolog (mutated in multiple advanced cancers 1) | PTEN | AF023139 | 0.007220107 | 1.5624946 |
| 114 | 218000_s_at | pleckstrin homology-like domain, family A, member 1 | PHLDA1 | NM_007350 | 0.016502094 | 1.6960312 |
| 115 | 218077_s_at | zinc finger, DHHC-type containing 3 | ZDHHC3 | BE542551 | 0.01684034 | 1.5417765 |
| 116 | 218078_s_at | zinc finger, DHHC-type containing 3 | ZDHHC3 | NM_016598 | 0.010970607 | 1.5836283 |
| 117 | 218435_at | DnaJ (Hsp40) homolog, subfamily C, member 15 | DNAJC15 | NM_013238 | 0.019865552 | 1.7292447 |
| 118 | 218644_at | pleckstrin 2 | PLEK2 | NM_016445 | 0.000675608 | 2.7071812 |
| 119 | 218748_s_at | SEC10-like 1 (S. cerevisiae) | SEC10L1 | NM_006544 | 0.012352341 | 1.7368068 |
| 120 | 218815_s_at | transmembrane protein 51 | TMEM51 | NM_018022 | 0.000753902 | 1.6477742 |
| 121 | 218826_at | solute carrier family 35, member F2 | SLC35F2 | NM_017515 | 0.009280122 | 1.6340361 |
| 122 | 218854_at | squamous cell carcinoma antigen recognized by T cells 2 | SART2 | NM_013352 | 0.014419112 | 1.6285655 |
| 123 | 218856_at | tumor necrosis factor receptor superfamily, member 21 | TNFRSF21 | NM_016629 | 0.01292243 | 1.617686 |
| 124 | 218885_s_at | UDP-N-acetyl-alpha-D-galactosamine:polypeptide N-acetylgalactosaminyltransferase 12 (GalNAc-T12) | GALNT12 | NM_024642 | 0.014052196 | 1.6402073 |
| 125 | 219410_at | transmembrane protein 45A | TMEM45A | NM_018004 | 0.018847797 | 2.0938365 |
| 126 | 219603_s_at | zinc finger protein 226 | ZNF226 | NM_015919 | 0.005593323 | 1.5408667 |
| 127 | 220199_s_at | chromosome 1 open reading frame 80 | C1orf80 | NM_022831 | 0.016323 | 1.5315142 |
| 128 | 220617_at | zinc finger protein 532 | ZNF532 | NM_018181 | 0.001976648 | 1.5441327 |
| 129 | 221268_s_at | sphingosine-1-phosphate phosphatase 1 | SGPP1 | NM_030791 | 0.008873873 | 1.9432548 |
| 130 | 221881_s_at | chloride intracellular channel 4 | CLIC4 | AI638420 | 0.004401053 | 1.7742935 |
| 131 | 222399_s_at | SM-11044 binding protein | SMBP | BG104571 | 0.00011337 | 1.5270268 |
| 132 | 222449_at | transmembrane, prostate androgen induced RNA | TMEPAI | AL035541 | 0.005303006 | 2.2757804 |
| 133 | 222528_s_at | solute carrier family 25, member 37 | SLC25A37 | BG251467 | 0.014745607 | 1.738053 |
| 134 | 222540_s_at | hepatitis B virus x associated protein | HBXAP | BG286920 | 0.005694628 | 1.5068418 |
| 135 | 222692_s_at | fibronectin type III domain containing 3B | FNDC3B | BF444916 | 0.001075083 | 1.5835624 |
| 136 | 222693_at | fibronectin type III domain containing 3B | FNDC3B | BF444916 | 0.000622161 | 1.7766397 |
| 137 | 222773_s_at | UDP-N-acetyl-alpha-D-galactosamine:polypeptide N-acetylgalactosaminyltransferase 12 (GalNAc-T12) | GALNT12 | AA554045 | 0.003090952 | 1.8790901 |
| 138 | 223577_x_at | PRO1073 protein | PRO1073 | AA827878 | 0.003659447 | 1.6790042 |
| 139 | 223940_x_at | metastasis associated lung adenocarcinoma transcript 1 (non-coding RNA) | MALAT1 | AF132202 | 0.016841894 | 1.9524238 |
| 140 | 224558_s_at | metastasis associated lung adenocarcinoma transcript 1 (non-coding RNA) | MALAT1 | AI446756 | 0.012874936 | 1.6367766 |
| 141 | 224674_at | tweety homolog 3 (Drosophila) | TTYH3 | AI934753 | 0.002428954 | 1.6452742 |
| 142 | 224733_s_at | chemokine-like factor superfamily 3 | CKLFSF3 | AL574900 | 0.013543638 | 1.5199631 |
| 143 | 224802_at | Nedd4 family interacting protein 2 | NDFIP2 | AA019338 | 0.013437813 | 1.5261155 |
| 144 | 225021_at | zinc finger protein 532 | ZNF532 | AA861416 | 0.002285053 | 1.6213596 |
| 145 | 225140_at | Kruppel-like factor 3 (basic) | KLF3 | BF438116 | 0.016804362 | 1.5368354 |
| 146 | 225168_at | FERM domain containing 4A | FRMD4A | T78406 | 0.006987929 | 1.5712297 |
| 147 | 225424_at | glycerol-3-phosphate acyltransferase, mitochondrial | GPAM | AB046780 | 0.000390623 | 1.7006425 |
| 148 | 225503_at | dehydrogenase/reductase (SDR family) X-linked | DHRSX | AL547782 | 0.005000754 | 1.770981 |
| 149 | 225567_at | Hypothetical LOC388114 | LOC388114 | BE207755 | 0.003047524 | 1.6990312 |
| 150 | 225609_at | glutathione reductase | GSR | AI888037 | 0.004693668 | 1.8490914 |
| 151 | 225842_at | Pleckstrin homology-like domain, family A, member 1 | PHLDA1 | AK026181 | 0.014052763 | 1.8735564 |
| 152 | 226084_at | microtubule-associated protein 1B | MAP1B | AA554833 | 0.016480966 | 1.9064581 |

-continued

| No. | Probe Set ID | Gene Name | Gene Symbol | Genbank Accession # | T-test p-value | Fold change (abs) |
|---|---|---|---|---|---|---|
| 153 | 226352_at | Junction-mediating and regulatory protein | JMY | BF447037 | 0.001219355 | 1.5196482 |
| 154 | 226726_at | O-acyltransferase (membrane bound) domain containing 2 | OACT2 | W63676 | 0.005363467 | 1.8277074 |
| 155 | 226780_s_at | hypothetical protein HSPC268 | HSPC268 | BF540829 | 0.001859941 | 1.5185972 |
| 156 | 227257_s_at | chromosome 10 open reading frame 46 | C10orf46 | AW973842 | 0.000646104 | 1.6094143 |
| 157 | 227628_at | similar to RIKEN cDNA 2310016C16 | LOC493869 | AL571557 | 0.006222301 | 2.0978951 |
| 158 | 227808_at | DnaJ (Hsp40) homolog, subfamily C, member 15 | DNAJC15 | AI091398 | 0.01153802 | 1.7936606 |
| 159 | 230206_at | Dedicator of cytokinesis 5 | DOCK5 | AI692645 | 0.005127667 | 1.6694399 |
| 160 | 231735_s_at | PRO1073 protein | PRO1073 | NM_014086 | 0.004784999 | 1.72546 |
| 161 | 231823_s_at | KIAA1295 | KIAA1295 | BG054798 | 0.002478401 | 1.5713933 |
| 162 | 235587_at | hypothetical protein LOC202781 | LOC202781 | BG400596 | 0.018314553 | 1.5202585 |
| 163 | 235879_at | Muscleblind-like (*Drosophila*) | MBNL1 | AI697540 | 0.002645486 | 2.0540323 |
| 164 | 238558_at | Muscleblind-like (*Drosophila*) | MBNL1 | AI445833 | 0.004576562 | 1.805269 |
| 165 | 238563_at | Ab1-interactor 1 | ABI1 | AV762916 | 0.012934915 | 1.6069295 |
| 166 | 238701_x_at | FLJ45803 protein | FLJ45803 | BE176566 | 0.01719282 | 1.5133282. |

20

14. A microarray for diagnosing a risk of lung cancer recurrence in a lung cancer patient or after a patient has lung cancer treatment, in which at least one probe or probe set specific to each target nucleic acid in a set of target nucleic acids consisting of target nucleic acids in Tables 1 is immobilized on a substrate, wherein Table 1 is shown below

| No. | Probe Set ID | Gene Name | Gene Symbol | Genbank Accession # | T-test p-value | Fold change (abs) |
|---|---|---|---|---|---|---|
| 001 | 1552486_s_at | lactamase, beta | LACTB | NM_171846 | 0.005162234 | 1.522293 |
| 002 | 1553105_s_at | desmoglein 2 | DSG2 | NM_001943 | 0.019467462 | 2.3323212 |
| 003 | 1553530_a_at | integrin, beta 1 (fibronectin receptor, beta polypeptide, antigen CD29 includes MDF2, MSK12) | ITGB1 | NM_033669 | 0.01684671 | 1.7791877 |
| 004 | 1553678_a_at | integrin, beta 1 (fibronectin receptor, beta polypeptide, antigen CD29 includes MDF2, MSK12) | ITGB1 | NM_133376 | 0.012459265 | 1.7374601 |
| 005 | 1554067_at | hypothetical protein FLJ32549 | FLJ32549 | BC036246 | 0.002290308 | 1.5143739 |
| 006 | 1554761_a_at | hypothetical protein FLJ20397 | FLJ20397 | BC010850 | 0.001210456 | 1.6267678 |
| 007 | 1555326_a_at | ADAM metallopeptidase domain 9 (meltrin gamma) | ADAM9 | AF495383 | 0.012324799 | 2.1980886 |
| 008 | 1555564_a_at | I factor (complement) | IF | BC020718 | 0.007528743 | 2.5875902 |
| 009 | 1555705_a_at | chemokine-like factor superfamily 3 | CKLFSF3 | AY166714 | 0.004961676 | 1.8687251 |
| 010 | 1557987_at | PI-3-kinase-related kinase SMG-1 - like locus | LOC641298 | BC042832 | 0.010989661 | 1.7944587 |
| 011 | 1558678_s_at | metastasis associated lung adenocarcinoma transcript 1 (non-coding RNA) | MALAT1 | BE708432 | 0.00670648 | 1.6990829 |
| 012 | 160020_at | matrix metallopeptidase 14 (membrane-inserted) | MMP14 | Z48481 | 0.005463324 | 1.5193439 |
| 013 | 200604_s_at | protein kinase, cAMP-dependent, regulatory, type I, alpha (tissue specific extinguisher 1) | PRKAR1A | M18468 | 0.017312625 | 1.5803499 |
| 014 | 200615_s_at | adaptor-related protein complex 2, beta 1 subunit | AP2B1 | AL567295 | 0.007407852 | 1.6839108 |
| 015 | 200864_s_at | RAB11A, member RAS oncogene family | RAB11A | NM_004663 | 0.000163535 | 1.5653288 |
| 016 | 200922_at | KDEL (Lys-Asp-Glu-Leu) endoplasmic reticulum protein retention receptor 1 | KDELR1 | NM_006801 | 0.004791257 | 1.638207 |
| 017 | 201020_at | tyrosine 3-monooxygenase/tryptophan 5-monooxygenase activation protein, eta polypeptide | YWHAH | NM_003405 | 0.009279575 | 1.5148095 |
| 018 | 201179_s_at | guanine nucleotide binding protein (G protein), alpha inhibiting activity polypeptide 3 | GNAI3 | J03005 | 0.014834337 | 1.5069977 |
| 019 | 201309_x_at | chromosome 5 open reading frame 13 | C5orf13 | U36189 | 0.011555359 | 2.1326842 |
| 020 | 201363_s_at | influenza virus NS1A binding protein | IVNS1ABP | AB020657 | 0.00119686 | 1.5838884 |
| 021 | 201505_at | laminin, beta 1 | LAMB1 | NM_002291 | 0.000568398 | 1.8073287 |
| 022 | 201506_at | transforming growth factor, beta-induced, 68 kDa | TGFBI | NM_000358 | 0.008768089 | 1.9059453 |
| 023 | 201548_s_at | Jumonji, AT rich interactive domain 1B (RBP2-like) | JARID1B | W02593 | 0.010550437 | 1.5276276 |
| 024 | 201559_s_at | chloride intracellular channel 4 | CLIC4 | AF109196 | 0.002245945 | 2.1570368 |
| 025 | 201564_s_at | fascin homolog 1, actin-bundling protein (*Strongylocentrotus purpuratus*) | FSCN1 | NM_003088 | 0.007795681 | 2.1724482 |
| 026 | 201578_at | podocalyxin-like | PODXL | NM_005397 | 0.00303411 | 1.8943018 |
| 027 | 201617_x_at | caldesmon 1 | CALD1 | NM_004342 | 0.01926877 | 1.8294148 |

-continued

| No. | Probe Set ID | Gene Name | Gene Symbol | Genbank Accession # | T-test p-value | Fold change (abs) |
|---|---|---|---|---|---|---|
| 028 | 201646_at | scavenger receptor class B, member 2 | SCARB2 | AA885297 | 0.006063032 | 1.6768507 |
| 029 | 201647_s_at | scavenger receptor class B, member 2 | SCARB2 | NM_005506 | 0.015885489 | 1.6841809 |
| 030 | 201695_s_at | nucleoside phosphorylase | NP | NM_000270 | 0.018524641 | 1.6833633 |
| 031 | 201722_s_at | UDP-N-acetyl-alpha-D-galactosamine:polypeptide N-acetylgalactosaminyltransferase 1 (GalNAc-T1) | GALNT1 | AV692127 | 0.009770202 | 1.5369248 |
| 032 | 201918_at | Solute carrier family 25, member 36 | SLC25A36 | AI927944 | 0.00259865 | 1.6228764 |
| 033 | 201942_s_at | carboxypeptidase D | CPD | D85390 | 0.017363481 | 1.7431495 |
| 034 | 202267_at | laminin, gamma 2 | LAMC2 | NM_005562 | 0.004330024 | 2.8191426 |
| 035 | 202543_s_at | glia maturation factor, beta | GMFB | BC005359 | 0.008048828 | 1.5254242 |
| 036 | 202604_x_at | ADAM metallopeptidase domain 10 | ADAM10 | NM_001110 | 0.002003783 | 1.767903 |
| 037 | 202627_s_at | serpin peptidase inhibitor, clade E (nexin, plasminogen activator inhibitor type 1), member 1 | SERPINE1 | AL574210 | 0.00091248 | 3.0523725 |
| 038 | 202628_s_at | serpin peptidase inhibitor, clade E (nexin, plasminogen activator inhibitor type 1), member 1 | SERPINE1 | NM_000602 | 0.00504642 | 2.6835847 |
| 039 | 202817_s_at | synovial sarcoma translocation, chromosome 18 | SS18 | NM_005637 | 0.005462693 | 1.5148987 |
| 040 | 202859_x_at | interleukin 8 | IL8 | NM_000584 | 0.014948112 | 2.1844351 |
| 041 | 202936_s_at | SRY (sex determining region Y)-box 9 (campomelic dysplasia, autosomal sex-reversal | SOX9 | NM_000346 | 0.019816045 | 2.2876046 |
| 042 | 202949_s_at | four and a half LIM domains 2 | FHL2 | NM_001450 | 0.006776552 | 2.2249734 |
| 043 | 202998_s_at | lysyl oxidase-like 2 | LOXL2 | NM_002318 | 0.006687925 | 2.0231075 |
| 044 | 203066_at | B cell RAG associated protein | GALNAC4S-6ST | NM_014863 | 0.00419499 | 1.5032523 |
| 045 | 203072_at | myosin IE | MYO1E | NM_004998 | 0.000449373 | 1.5877136 |
| 046 | 203293_s_at | lectin, mannose-binding, 1 | LMAN1 | NM_005570 | 0.002661762 | 1.9762497 |
| 047 | 203294_s_at | lectin, mannose-binding, 1 | LMAN1 | U09716 | 0.000473367 | 1.9764429 |
| 048 | 203414_at | monocyte to macrophage differentiation-associated | MMD | NM_012329 | 0.001585437 | 1.6128623 |
| 049 | 203553_s_at | mitogen-activated protein kinase kinase kinase kinase 5 | MAP4K5 | NM_006575 | 0.010453912 | 1.5251595 |
| 050 | 203924_at | glutathione S-transferase A1 | GSTA1 | NM_000846 | 0.004046575 | 4.2017674 |
| 051 | 203988_s_at | fucosyltransferase 8 (alpha (1,6) fucosyltransferase) | FUT8 | NM_004480 | 0.01139016 | 1.6090198 |
| 052 | 204426_at | transmembrane emp24 domain trafficking protein 2 | TMED2 | NM_006815 | 0.015985437 | 1.6165011 |
| 053 | 204470_at | chemokine (C-X-C motif) ligand 1 (melanoma growth stimulating activity, alpha) | CXCL1 | NM_001511 | 0.001788037 | 3.218731 |
| 054 | 204702_s_at | nuclear factor (erythroid-derived 2)-like 3 | NFE2L3 | NM_004289 | 0.015985157 | 1.7023398 |
| 055 | 204790_at | SMAD, mothers against DPP homolog 7 (*Drosophila*) | SMAD7 | NM_005904 | 0.013379821 | 1.7179344 |
| 056 | 204944_at | protein tyrosine phosphatase, receptor type, G | PTPRG | NM_002841 | 0.004963213 | 1.769544 |
| 057 | 204989_s_at | integrin, beta 4 | ITGB4 | BF305661 | 0.012746719 | 2.1320713 |
| 058 | 205120_s_at | sarcoglycan, beta (43 kDa dystrophin-associated glycoprotein) | SGCB | U29586 | 0.013908542 | 1.7317705 |
| 059 | 205180_s_at | ADAM metallopeptidase domain 8 | ADAM8 | NM_001109 | 0.000473816 | 2.054043 |
| 060 | 205479_s_at | plasminogen activator, urokinase | PLAU | NM_002658 | 0.003415823 | 2.4370956 |
| 061 | 206025_s_at | tumor necrosis factor, alpha-induced protein 6 | TNFAIP6 | AW188198 | 0.013965369 | 2.1515768 |
| 062 | 206113_s_at | RAB5A, member RAS oncogene family | RAB5A | NM_004162 | 0.010821017 | 1.571063 |
| 063 | 206116_s_at | tropomyosin 1 (alpha) | TPM1 | NM_000366 | 0.000283653 | 2.0841253 |
| 064 | 206245_s_at | influenza virus NS1A binding protein | IVNS1ABP | NM_006469 | 0.003607815 | 1.5105128 |
| 065 | 206323_x_at | oligophrenin 1 | OPHN1 | NM_002547 | 0.018292218 | 1.5056778 |
| 066 | 208510_s_at | peroxisome proliferative activated receptor, gamma | PPARG | NM_015869 | 0.002361554 | 1.882336 |
| 067 | 208613_s_at | filamin B, beta (actin binding protein 278) | FLNB | AV712733 | 0.001033398 | 1.7958127 |
| 068 | 208637_x_at | actinin, alpha 1 | ACTN1 | BC003576 | 0.000448714 | 1.631627 |
| 069 | 208653_s_at | CD164 antigen, sialomucin | CD164 | AF263279 | 0.017487219 | 1.5380286 |
| 070 | 208853_s_at | calnexin | CANX | L18887 | 0.011792572 | 1.5100785 |
| 071 | 209131_s_at | synaptosomal-associated protein, 23 kDa | SNAP23 | U55936 | 0.001730693 | 1.8878508 |
| 072 | 209209_s_at | pleckstrin homology domain containing, family C (with FERM domain) member 1 | PLEKHC1 | AW469573 | 0.009551367 | 1.9820172 |
| 073 | 209314_s_at | HBS1-like (*S. cerevisiae*) | HBS1L | AK024258 | 0.00507411 | 1.6641864 |
| 074 | 209316_s_at | HBS1-like (*S. cerevisiae*) | HBS1L | BC001465 | 0.006051209 | 1.6464524 |
| 075 | 209409_at | growth factor receptor-bound protein 10 | GRB10 | D86962 | 0.01098607 | 1.7481923 |
| 076 | 209410_s_at | growth factor receptor-bound protein 10 | GRB10 | AF000017 | 0.013879589 | 1.701537 |
| 077 | 209537_at | exostoses (multiple)-like 2 | EXTL2 | AF000416 | 0.003979554 | 1.5687809 |
| 078 | 210845_s_at | plasminogen activator, urokinase receptor | PLAUR | U08839 | 0.007479298 | 1.7924315 |
| 079 | 210892_s_at | general transcription factor II,i | GTF2I | BC004472 | 0.003141172 | 1.619537 |
| 080 | 210933_s_at | fascin homolog 1, actin-bundling protein (*Strongylocentrotus purpuratus*) | FSCN1 | BC004908 | 0.00342191 | 1.906748 |

-continued

| No. | Probe Set ID | Gene Name | Gene Symbol | Genbank Accession # | T-test p-value | Fold change (abs) |
|---|---|---|---|---|---|---|
| 081 | 210987_x_at | tropomyosin 1 (alpha) | TPM1 | M19267 | 0.004614187 | 1.6935222 |
| 082 | 211299_s_at | flotillin 2 | FLOT2 | BC003683 | 0.015057402 | 1.5387125 |
| 083 | 211506_s_at | interleukin 8 | IL8 | AF043337 | 0.005428782 | 2.867063 |
| 084 | 211559_s_at | cyclin G2 | CCNG2 | L49506 | 0.010491861 | 1.8367761 |
| 085 | 211599_x_at | met proto-oncogene (hepatocyte growth factor receptor) | MET | U19348 | 0.019789577 | 1.9247686 |
| 086 | 211651_s_at | laminin, beta 1 | LAMB1 | M20206 | 0.000418344 | 1.997547 |
| 087 | 211668_s_at | plasminogen activator, urokinase | PLAU | K03226 | 0.00240352 | 2.8568754 |
| 088 | 211864_s_at | fer-1-like 3, myoferlin (C. elegans) | FER1L3 | AF207990 | 0.011889962 | 1.7860718 |
| 089 | 211924_s_at | plasminogen activator, urokinase receptor | PLAUR | AY029180 | 0.011789334 | 1.8189595 |
| 090 | 211981_at | collagen, type IV, alpha 1 | COL4A1 | NM_001845 | 0.007531395 | 1.8490748 |
| 091 | 212012_at | peroxidasin homolog (Drosophila) | PXDN | BF342851 | 0.016265145 | 1.8463359 |
| 092 | 212660_at | PHD finger protein 15 | PHF15 | AI735639 | 0.007391165 | 1.5595657 |
| 093 | 212720_at | poly(A) polymerase alpha | PAPOLA | AI670847 | 0.016607396 | 1.5904158 |
| 094 | 212907_at | Solute carrier family 30 (zinc transporter), member 1 | SLC30A1 | AI972416 | 0.002460855 | 1.63999 |
| 095 | 213288_at | O-acyltransferase (membrane bound) domain containing 2 | OACT2 | AI761250 | 0.010427832 | 1.6232696 |
| 096 | 213457_at | malignant fibrous histiocytoma amplified sequence 1 | MFHAS1 | BF739959 | 0.003050241 | 1.8505166 |
| 097 | 213624_at | sphingomyelin phosphodiesterase, acid-like 3A | SMPDL3A | AA873600 | 0.005912889 | 1.8562527 |
| 098 | 213742_at | splicing factor, arginine/serine-rich 11 | SFRS11 | AW241752 | 0.006011819 | 1.9170463 |
| 099 | 214121_x_at | PDZ and LIM domain 7 (enigma) | PDLIM7 | AA086229 | 5.50514E−05 | 1.5048952 |
| 100 | 214196_s_at | tripeptidyl peptidase I | TPP1 | AA602532 | 0.015398935 | 1.5939685 |
| 101 | 214544_s_at | synaptosomal-associated protein, 23 kDa | SNAP23 | NM_003825 | 0.003539713 | 1.8040004 |
| 102 | 214581_x_at | tumor necrosis factor receptor superfamily, member 21 | TNFRSF21 | BE568134 | 0.002274355 | 2.2189345 |
| 103 | 214701_s_at | fibronectin 1 | FN1 | AJ276395 | 0.001182322 | 2.071262 |
| 104 | 214866_at | plasminogen activator, urokinase receptor | PLAUR | X74039 | 0.003173471 | 1.7340106 |
| 105 | 214895_s_at | ADAM metallopeptidase domain 10 | ADAM10 | AU135154 | 0.004170008 | 1.9890832 |
| 106 | 215501_s_at | dual specificity phosphatase 10 | DUSP10 | AK022513 | 0.018290011 | 1.5388945 |
| 107 | 216035_x_at | transcription factor 7-like 2 (T-cell specific, HMG-box) | TCF7L2 | AV721430 | 0.000657631 | 1.7091621 |
| 108 | 216511_s_at | transcription factor 7-like 2 (T-cell specific, HMG-box) | TCF7L2 | AJ270770 | 0.004103699 | 1.5264177 |
| 109 | 216915_s_at | protein tyrosine phosphatase, non-receptor type 12 | PTPN12 | S69182 | 0.005493577 | 1.6935816 |
| 110 | 216971_s_at | plectin 1, intermediate filament binding protein 500 kDa | PLEC1 | Z54367 | 0.01826363 | 1.7186335 |
| 111 | 217188_s_at | chromosome 14 open reading frame 1 | C14orf1 | AC007182 | 0.011925477 | 1.6185476 |
| 112 | 217448_s_at | chromosome 14 open reading frame 92 similar to Epidermal Langerhans cell protein LCP1 | C14orf92 LOC285412 | AL117508 | 0.007782524 | 1.5433311 |
| 113 | 217492_s_at | phosphatase and tensin homolog (mutated in multiple advanced cancers 1) | PTEN | AF023139 | 0.007220107 | 1.5624946 |
| 114 | 218000_s_at | pleckstrin homology-like domain, family A, member 1 | PHLDA1 | NM_007350 | 0.016502094 | 1.6960312 |
| 115 | 218077_s_at | zinc finger, DHHC-type containing 3 | ZDHHC3 | BE542551 | 0.01684034 | 1.5417765 |
| 116 | 218078_s_at | zinc finger, DHHC-type containing 3 | ZDHHC3 | NM_016598 | 0.010970607 | 1.5836283 |
| 117 | 218435_at | DnaJ (Hsp40) homolog, subfamily C, member 15 | DNAJC15 | NM_013238 | 0.019865552 | 1.7292447 |
| 118 | 218644_at | pleckstrin 2 | PLEK2 | NM_016445 | 0.000675608 | 2.7071812 |
| 119 | 218748_s_at | SEC10-like 1 (S. cerevisiae) | SEC10L1 | NM_006544 | 0.012352341 | 1.7368068 |
| 120 | 218815_s_at | transmembrane protein 51 | TMEM51 | NM_018022 | 0.000753902 | 1.6477742 |
| 121 | 218826_at | solute carrier family 35, member F2 | SLC35F2 | NM_017515 | 0.009280122 | 1.6340361 |
| 122 | 218854_at | squamous cell carcinoma antigen recognized by T cells 2 | SART2 | NM_013352 | 0.014419112 | 1.6285655 |
| 123 | 218856_at | tumor necrosis factor receptor superfamily, member 21 | TNFRSF21 | NM_016629 | 0.01292243 | 1.617686 |
| 124 | 218885_s_at | UDP-N-acetyl-alpha-D-galactosamine:polypeptide N-acetylgalactosaminyltransferase 12 (GalNAc-T12) | GALNT12 | NM_024642 | 0.014052196 | 1.6402073 |
| 125 | 219410_at | transmembrane protein 45A | TMEM45A | NM_018004 | 0.018847797 | 2.0938365 |
| 126 | 219603_s_at | zinc finger protein 226 | ZNF226 | NM_015919 | 0.005593323 | 1.5408667 |
| 127 | 220199_s_at | chromosome 1 open reading frame 80 | C1orf80 | NM_022831 | 0.016323 | 1.5315142 |
| 128 | 220617_s_at | zinc finger protein 532 | ZNF532 | NM_018181 | 0.001976648 | 1.5441327 |
| 129 | 221268_s_at | sphingosine-1-phosphate phosphatase 1 | SGPP1 | NM_030791 | 0.008873873 | 1.9432548 |
| 130 | 221881_s_at | chloride intracellular channel 4 | CLIC4 | AI638420 | 0.004401053 | 1.7742935 |
| 131 | 222399_s_at | SM-11044 binding protein | SMBP | BG104571 | 0.00011337 | 1.5270268 |
| 132 | 222449_at | transmembrane, prostate androgen induced RNA | TMEPAI | AL035541 | 0.005303006 | 2.2757804 |
| 133 | 222528_s_at | solute carrier family 25, member 37 | SLC25A37 | BG251467 | 0.014745607 | 1.738053 |
| 134 | 222540_s_at | hepatitis B virus x associated protein | HBXAP | BG286920 | 0.005694628 | 1.5068418 |
| 135 | 222692_s_at | fibronectin type III domain containing 3B | FNDC3B | BF444916 | 0.001075083 | 1.5835624 |
| 136 | 222693_at | fibronectin type III domain containing 3B | FNDC3B | BF444916 | 0.000622161 | 1.7766397 |

-continued

| No. | Probe Set ID | Gene Name | Gene Symbol | Genbank Accession # | T-test p-value | Fold change (abs) |
|---|---|---|---|---|---|---|
| 137 | 222773_s_at | UDP-N-acetyl-alpha-D-galactosamine:polypeptide N-acetylgalactosaminyltransferase 12 (GalNAc-T12) | GALNT12 | AA554045 | 0.003090952 | 1.8790901 |
| 138 | 223577_x_at | PRO1073 protein | PRO1073 | AA827878 | 0.003659447 | 1.6790042 |
| 139 | 223940_x_at | metastasis associated lung adenocarcinoma transcript 1 (non-coding RNA) | MALAT1 | AF132202 | 0.016841894 | 1.9524238 |
| 140 | 224558_s_at | metastasis associated lung adenocarcinoma transcript 1 (non-coding RNA) | MALAT1 | AI446756 | 0.012874936 | 1.6367766 |
| 141 | 224674_at | tweety homolog 3 (*Drosophila*) | TTYH3 | AI934753 | 0.002428954 | 1.6452742 |
| 142 | 224733_at | chemokine-like factor superfamily 3 | CKLFSF3 | AL574900 | 0.013543638 | 1.5199631 |
| 143 | 224802_at | Nedd4 family interacting protein 2 | NDFIP2 | AA019338 | 0.013437813 | 1.5261155 |
| 144 | 225021_at | zinc finger protein 532 | ZNF532 | AA861416 | 0.002285053 | 1.6213596 |
| 145 | 225140_at | Kruppel-like factor 3 (basic) | KLF3 | BF438116 | 0.016804362 | 1.5368354 |
| 146 | 225168_at | FERM domain containing 4A | FRMD4A | T78406 | 0.006987929 | 1.5712297 |
| 147 | 225424_at | glycerol-3-phosphate acyltransferase, mitochondrial | GPAM | AB046780 | 0.000390623 | 1.7006425 |
| 148 | 225503_at | dehydrogenase/reductase (SDR family) X-linked | DHRSX | AL547782 | 0.005000754 | 1.770981 |
| 149 | 225567_at | Hypothetical LOC388114 | LOC388114 | BE207755 | 0.003047524 | 1.6990312 |
| 150 | 225609_at | glutathione reductase | GSR | AI888037 | 0.004693668 | 1.8490914 |
| 151 | 225842_at | Pleckstrin homology-like domain, family A, member 1 | PHLDA1 | AK026181 | 0.014052763 | 1.8735564 |
| 152 | 226084_at | microtubule-associated protein 1B | MAP1B | AA554833 | 0.016480966 | 1.9064581 |
| 153 | 226352_at | Junction-mediating and regulatory protein | JMY | BF447037 | 0.001219355 | 1.5196482 |
| 154 | 226726_at | O-acyltransferase (membrane bound) domain containing 2 | OACT2 | W63676 | 0.005363467 | 1.8277074 |
| 155 | 226780_s_at | hypothetical protein HSPC268 | HSPC268 | BF540829 | 0.001859941 | 1.5185972 |
| 156 | 227257_s_at | chromosome 10 open reading frame 46 | C10orf46 | AW973842 | 0.000646104 | 1.6094143 |
| 157 | 227628_at | similar to RIKEN cDNA 2310016C16 | LOC493869 | AL571557 | 0.006222301 | 2.0978951 |
| 158 | 227808_at | DnaJ (Hsp40) homolog, subfamily C, member 15 | DNAJC15 | AI091398 | 0.01153802 | 1.7936606 |
| 159 | 230206_at | Dedicator of cytokinesis 5 | DOCK5 | AI692645 | 0.005127667 | 1.6694399 |
| 160 | 231735_s_at | PRO1073 protein | PRO1073 | NM_014086 | 0.004784999 | 1.72546 |
| 161 | 231823_s_at | KIAA1295 | KIAA1295 | BG054798 | 0.002478401 | 1.5713933 |
| 162 | 235587_at | hypothetical protein LOC202781 | LOC202781 | BG400596 | 0.018314553 | 1.5202585 |
| 163 | 235879_at | Muscleblind-like (*Drosophila*) | MBNL1 | AI697540 | 0.002645486 | 2.0540323 |
| 164 | 238558_at | Muscleblind-like (*Drosophila*) | MBNL1 | AI445833 | 0.004576562 | 1.805269 |
| 165 | 238563_at | Ab1-interactor 1 | ABI1 | AV762916 | 0.012934915 | 1.6069295 |
| 166 | 238701_x_at | FLJ45803 protein | FLJ45803 | BE176566 | 0.01719282 | 1.5133282. |

\* \* \* \* \*